(12) United States Patent
Green et al.

(10) Patent No.: US 9,701,959 B2
(45) Date of Patent: Jul. 11, 2017

(54) HIGH THROUGHPUT SCREEN FOR BIOLOGICALLY ACTIVE POLYPEPTIDES

(71) Applicant: Invenra Inc., Madison, WI (US)

(72) Inventors: Roland Green, Madison, WI (US); Bryan Glaser, Fitchburg, WI (US); Ivar Meyvantsson, Madison, WI (US); Kimberly Kaufman, Madison, WI (US); Madison Green, Madison, WI (US)

(73) Assignee: INVENRA INC., Madison, WI (US)

( * ) Notice: Subject to any disclaimer, the term of this patent is extended or adjusted under 35 U.S.C. 154(b) by 0 days.

(21) Appl. No.: 14/375,943

(22) PCT Filed: Feb. 1, 2013

(86) PCT No.: PCT/US2013/024406
§ 371 (c)(1),
(2) Date: Jul. 31, 2014

(87) PCT Pub. No.: WO2013/116698
PCT Pub. Date: Aug. 8, 2013

(65) Prior Publication Data
US 2015/0018236 A1    Jan. 15, 2015

Related U.S. Application Data

(60) Provisional application No. 61/594,149, filed on Feb. 2, 2012.

(51) Int. Cl.
*C12N 15/10*    (2006.01)

(52) U.S. Cl.
CPC ..... *C12N 15/1075* (2013.01); *C12N 15/1086* (2013.01)

(58) Field of Classification Search
CPC .................... C12N 15/1075; C12N 15/1086
USPC ........................................................ 506/9
See application file for complete search history.

(56) References Cited

U.S. PATENT DOCUMENTS

| | | | |
|---|---|---|---|
| 6,377,721 B1 | 4/2002 | Walt et al. | 385/12 |
| 6,489,103 B1 | 12/2002 | Griffiths et al. | 435/6.16 |
| 6,808,882 B2 | 10/2004 | Griffiths et al. | 506/1 |
| 7,138,233 B2 | 11/2006 | Griffiths et al. | 435/6.16 |

(Continued)

FOREIGN PATENT DOCUMENTS

| | | |
|---|---|---|
| WO | WO 98/58085 | 12/1998 |
| WO | WO 99/02671 | 1/1999 |

(Continued)

OTHER PUBLICATIONS

He, Mingyue (New Biotechnology, vol. 25, Nos. 2/3, Oct./Dec. 2008, pp. 127-132).*

(Continued)

*Primary Examiner* — Karla Dines
(74) *Attorney, Agent, or Firm* — Parker Highlander PLLC

(57) ABSTRACT

Methods for screening libraries of polypeptides for biologically activity on cells. For example, polypeptides can be synthesized and encapsulated along with their coding sequences in microcapsules of an emulsion. Emulsion microcapsules can then be fused with microcapsules comprising test cells and biological activity on the cells is assessed to identify biologically active polypeptides and nucleic acid molecules encoding the same.

21 Claims, 40 Drawing Sheets

(56) References Cited

U.S. PATENT DOCUMENTS

| | | | |
|---|---|---|---|
| 7,527,954 | B2 | 5/2009 | Bertschinger et al. ........ 435/193 |
| 7,585,815 | B2 | 9/2009 | Beernink et al. ................. 506/3 |
| 7,638,276 | B2 | 12/2009 | Griffiths et al. ............. 435/6.16 |
| 7,674,752 | B2 | 3/2010 | He et al. ......................... 506/26 |
| 7,842,457 | B2 | 11/2010 | Berka et al. ................. 435/6.16 |
| 7,897,341 | B2 | 3/2011 | Griffiths et al. ............. 435/6.16 |
| 8,298,995 | B2 | 10/2012 | Taussig et al. ................. 506/26 |
| 8,309,035 | B2 | 11/2012 | Chen et al. .................... 422/407 |
| 2006/0003347 | A1 | 1/2006 | Griffiths et al. ............. 435/6.12 |
| 2006/0210982 | A1* | 9/2006 | Yanagawa .............. C07K 14/00 435/6.12 |
| 2007/0077572 | A1 | 4/2007 | Tawfik et al. ................ 435/6.16 |
| 2009/0197248 | A1 | 8/2009 | Griffiths et al. ............. 435/6.11 |
| 2010/0009872 | A1* | 1/2010 | Eid .................. G01N 33/54313 506/26 |

FOREIGN PATENT DOCUMENTS

| | | |
|---|---|---|
| WO | WO 00/40712 | 7/2000 |
| WO | WO 02/14860 | 2/2002 |
| WO | WO 02/22869 | 3/2002 |
| WO | WO 03/044187 | 5/2003 |
| WO | WO 2004/069849 | 8/2004 |
| WO | WO 2004/087308 | 10/2004 |
| WO | WO 2004/088314 | 10/2004 |
| WO | WO 2005/007796 | 1/2005 |
| WO | WO 2005/030957 | 4/2005 |
| WO | WO 2005/045072 | 5/2005 |
| WO | WO 2005/052117 | 6/2005 |
| WO | WO 2006/038035 | 4/2006 |
| WO | WO 2006/040551 | 4/2006 |
| WO | WO 2006/040554 | 4/2006 |
| WO | WO 2011/005221 | 1/2011 |

OTHER PUBLICATIONS

Gan et al. (Biotechnology Progress, 2008, 24, pp. 1107-1114).*

Aharoni, et al., "High-throughput screening of enzyme libraries: thiolactonases evolved by fluorescence-activated sorting of single cells in emulsion compartments," *Chem. Biol.*, 12:1281-9, 2005.

Brouzes, et al., "Droplet microfluidic technology for single-cell high-throughput screening," *Proc. Natl. Acad. Sci. USA*, 106:14195-200, 2009.

Ghadessy and Holliger, "A novel emulsion mixture for in vitro compartmentalization of transcription and translation in the rabbit reticulocyte system," *Protein Eng. Des. Sel.*, 17:201-4, 2004.

Griffiths and Tawfik "Directed evolution of an extremely fast phosphotriesterase by in vitro compartmentalization," *EMBO J.*, 22:24-35, 2003.

Hillberg and Tabrizian, "Biorecognition through layer-by-layer polyelectrolyte assembly: in-situ hybridization on living cells," *Biomacromolecules*, 7:2742-50, 2006.

International Search Report and Written Opinion issued in Application No. PCT/US2013/024406, dated Sep. 16, 2013.

Invitation to Pay Additional Fees and Partial Search Report issued in Application No. PCT/US2013/024406, dated Jun. 28, 2013.

Maeda, et al., "Transmembrane segment peptides with double D-amino acid replacements: helicity, hydrophobicity, and antimicrobial activity," *Biopolymers*, 71:77-84, 2003.

Sumida, et al., "Bicistronic DNA display for in vitro selection of Fab fragments," *Nucleic Acids Res.*, 37:e147, 2009.

Takulapalli, et al., "High density diffusion-free nanowell arrays," *J. Proteome Res.*, 11:4382-91, 2012.

Williams, et al., "Amplification of complex gene libraries by emulsion PCR," *Nat. Methods*, 3:545-50, 2006.

English translation of Office Communication issued in Japanese Patent Application No. 2014-555774, dated Nov. 4, 2016.

* cited by examiner

Fig. 1A Synthetic DNA library
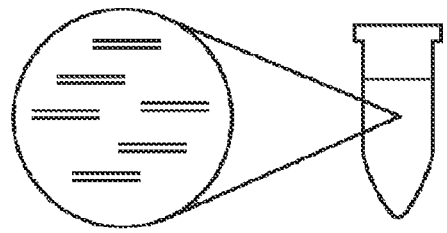
Fig. 1B Emulsion Polymerase Chain Reaction
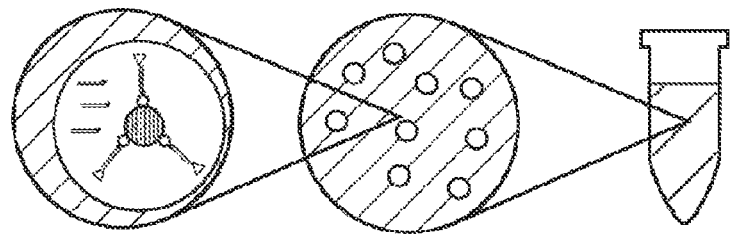
Fig. 1C Emulsion Expression
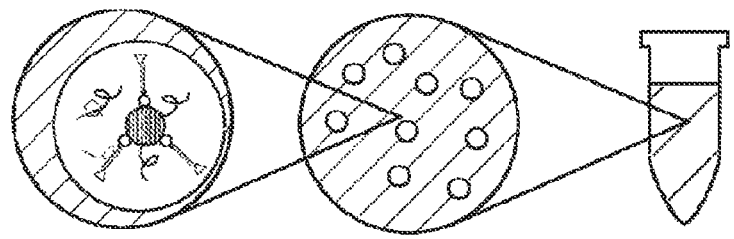

Fig. 1D Bead Washing
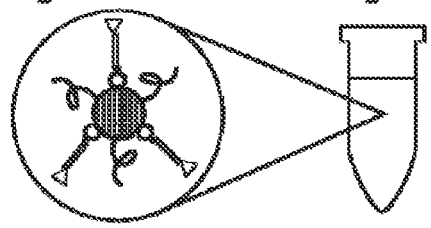
Fig. 1E Emulsion Assay
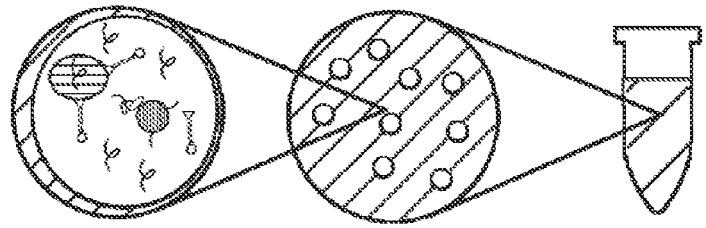
Fig. 1F Hit Collection
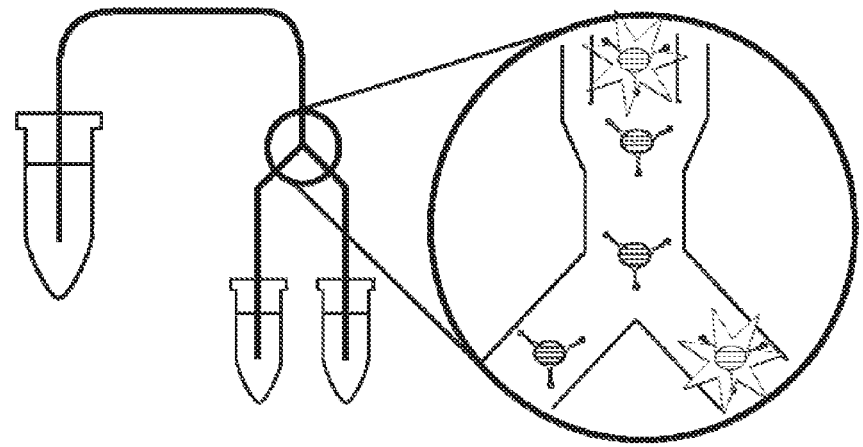

Fig. 2A Synthetic DNA library
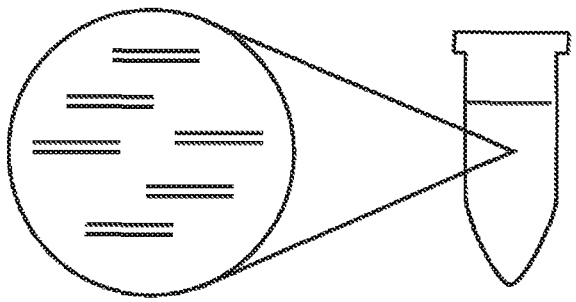
Fig. 2B Emulsion Polymerase Chain Reaction
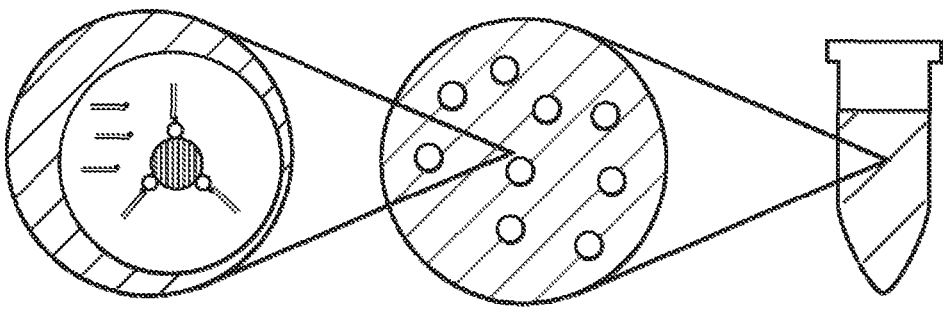
Fig. 2C Emulsion Expression
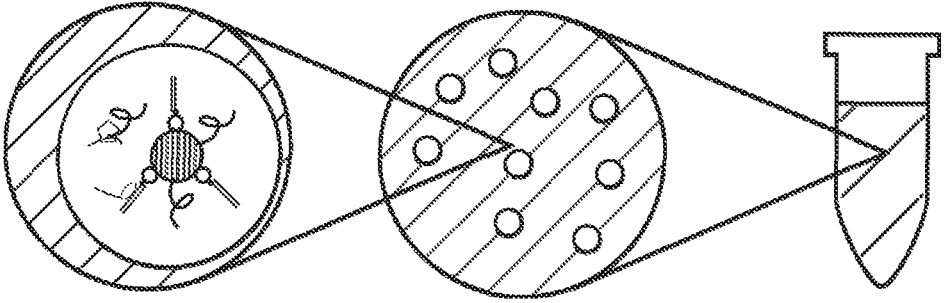

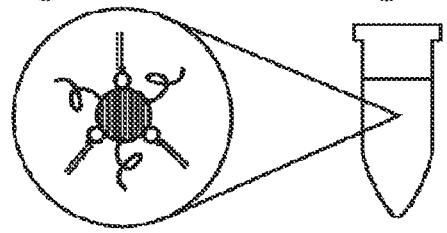
Fig. 2D Bead Washing
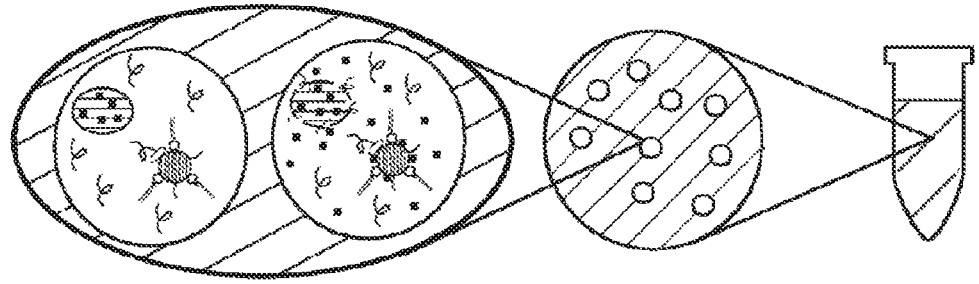
Fig. 2E Emulsion Assay
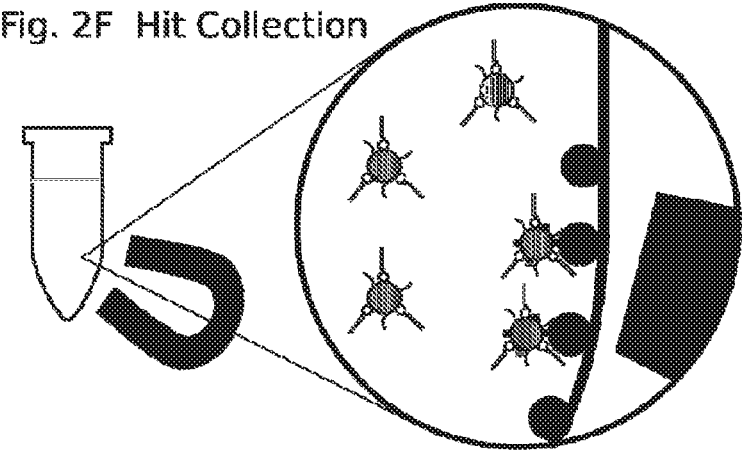
Fig. 2F Hit Collection Fig. 3A Synthetic DNA library
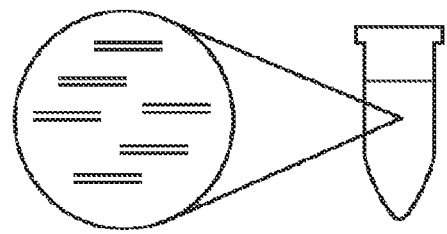
Fig. 3B Emulsion Polymerase Chain Reaction
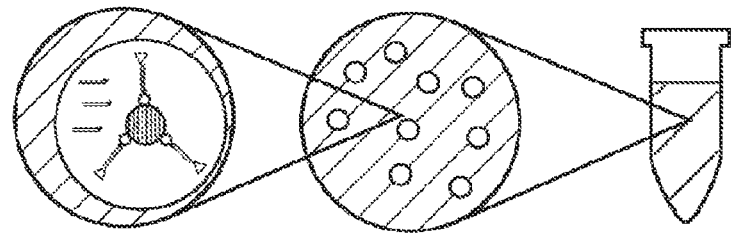
Fig. 3C Emulsion Expression
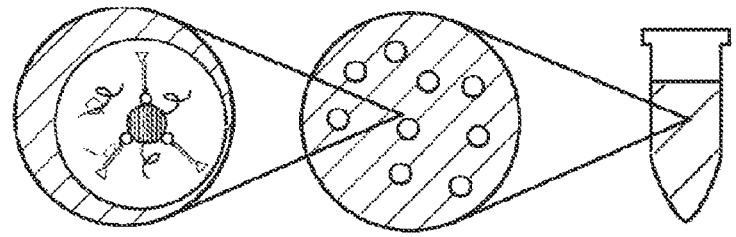

Fig. 3D Bead Washing
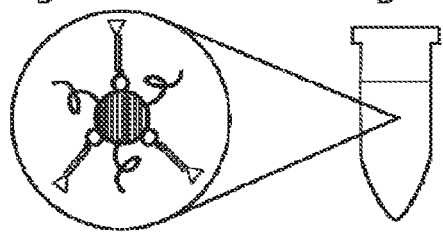
Fig. 3E Emulsion Assay
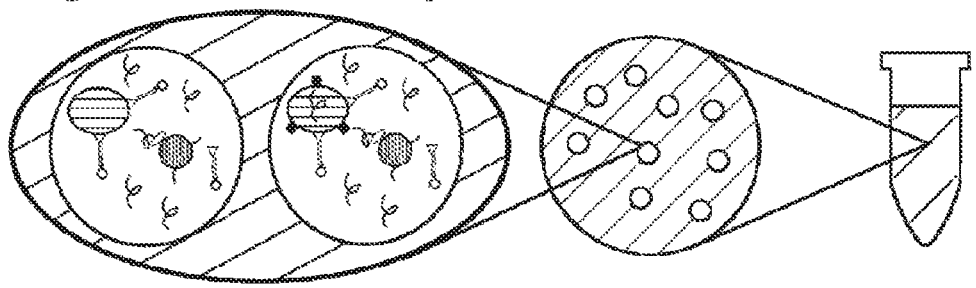
Fig. 3F Hit Collection
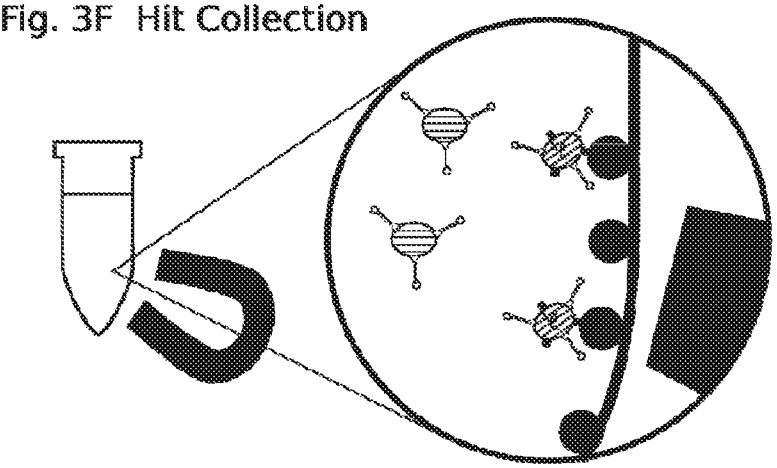

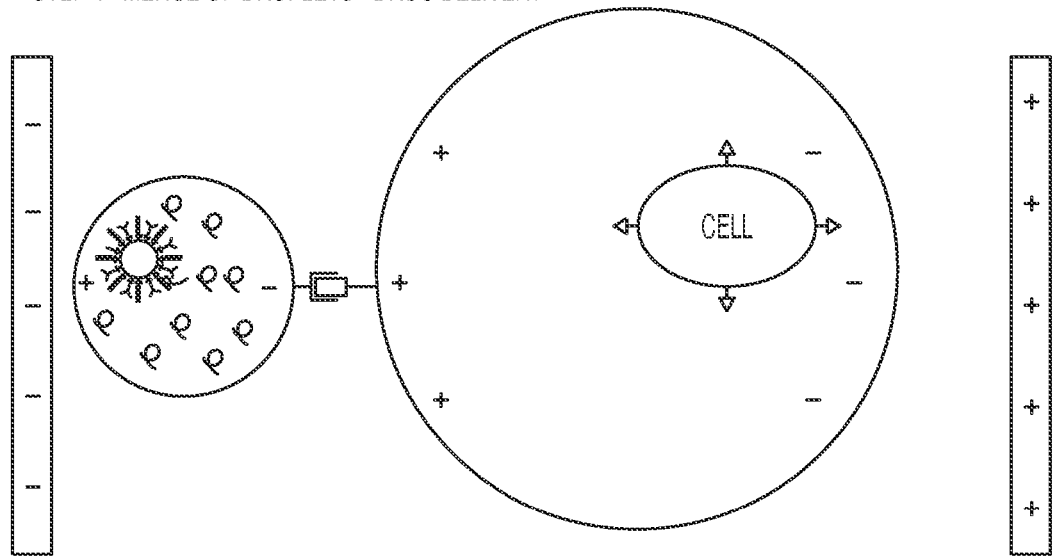
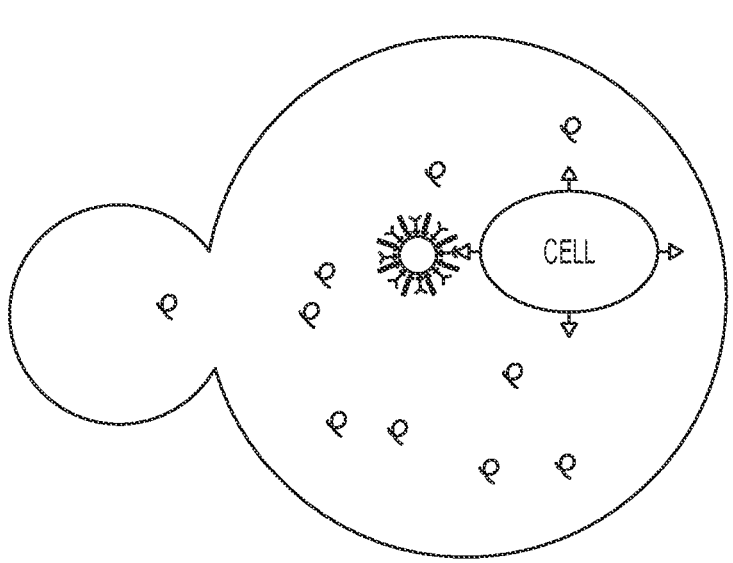
FIG. 4B

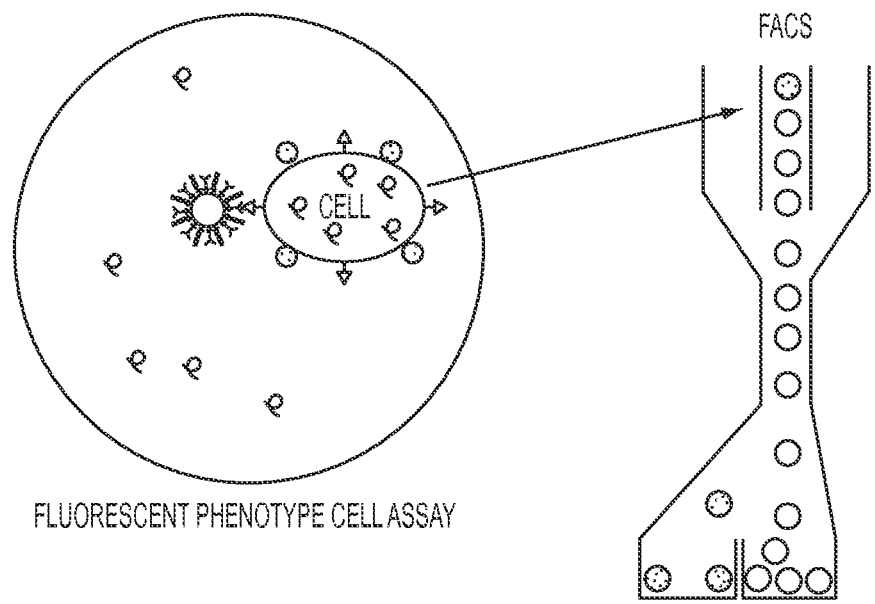
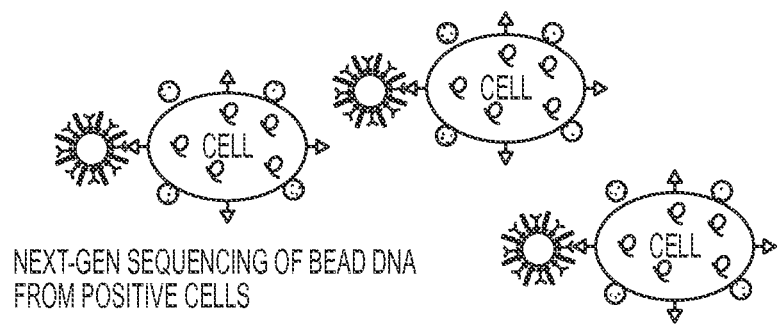
FIG. 4C

MELITTIN LIBRARY DESIGN

| -4 | -3 | -2 | -1 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|---|
| E | V | K | H | M | H | H | H | H | H | H | E | N | L | Y | F | Q | G | G | I |
| GAG | GTA | AAA | CAT | ATG | CAT | CAC | CAC | CAC | CAT | CAC | GAG | AAT | CTG | TAC | TTT | CAA | GGC | GGT | ATC |

| 17 | 18 | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|
| G | A | V | L | K | V | L | T | T | G | L | P | A | L | I | S | W | I | K | R |
| GGC | GCA | GTT | CTG | AAA | GTG | CTG | ACC | ACG | GGT | TTG | CCG | GCT | CTG | ATT | AGC | TGG | ATC | AAA | CGT |

| 37 | 38 | 39 | 40 | 41 | 42 | 43 | 44 |
|---|---|---|---|---|---|---|---|
| K | R | Q | Q | - | - | L | E |
| AAG | CGC | CAG | CAG | TGA | TAA | CTC | GAG |

(circle) = DIVERSITY SITES

DIVERSITIES

| | 19 | 20 | 24 | 28 | 29 | 36 | 39 | 40 |
|---|---|---|---|---|---|---|---|---|
| Melittin_base_B6221 | V<br>GTT | L<br>CTG | I<br>ACC | P<br>CCG | A<br>GCT | R<br>CGT | Q<br>CAG | Q<br>CAG |
| B_position | All | All | All | P<br>CCG<br>R<br>CGT | All | All | All | All |

LIBRARY MUTATIONS IN MELITTIN

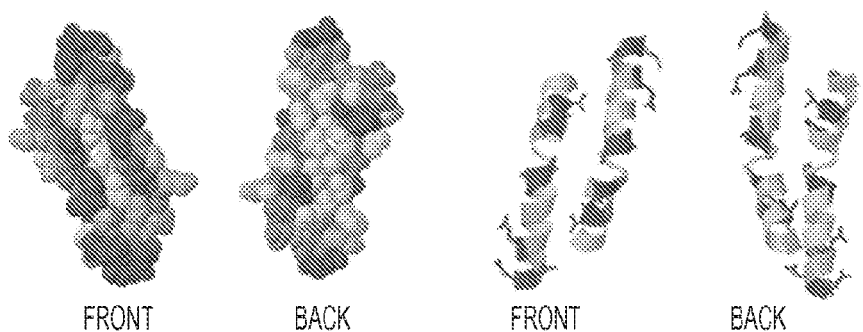

FRONT BACK FRONT BACK

GIGAVLKVLTTGLPALISWIKRKRQQ

LIBRARY SIZE ~ 6.9e10[10]

DARK GREY = SITES OF DIVERSITY

HIGH THROUGHPUT SCREEN FOR BIOLOGICALLY ACTIVE POLYPEPTIDES

This is a national phase application under 35 U.S.C. §371 of International Application No. PCT/US2013/024406, filed Feb. 1, 2013, which claims the benefit of priority to U.S. Provisional Patent Application No. 61/594,149, filed Feb. 2, 2012. The entire contents of each of the above referenced disclosures are specifically incorporated herein by reference.

The sequence listing that is contained in the file named "INVRP0002US_ST25.txt", which is 18.9 KB (as measured in Microsoft Windows®) and was created on Jul. 30, 2014, is filed herewith by electronic submission and is incorporated by reference herein.

BACKGROUND OF THE INVENTION

1. Field of the Invention

The present invention relates generally to the field of biochemistry and molecular biology. More particularly, it concerns methods to isolate and identify biologically active polypeptides.

2. Description of Related Art

Many of the most effective modern therapeutics are polypeptide molecules such as monoclonal antibodies. In the case of antibodies, the mammalian immune system provides a highly adapted system for development of antibody molecules that are specific for a given therapeutic target. Modern molecular biology techniques allow the sequences for these antibodies to be isolated, such that therapeutics based on the antibody sequences can be mass produced in fermentation systems. Unfortunately, the development of antibody therapeutics is limited in that the therapeutic target must be known, be antigenic and be accessible on the surface of a target cell.

Accordingly, methods for identifying candidate biologically active polypeptides by using molecular libraries are being explored. However, any such system requires that the library have sufficient diversity to interrogate a vast range of candidate molecules. Moreover, any assay using such a library must provide a system for determining the coding sequence for polypeptides that are identified in a binding or biological activity screen. In some cases, the polypeptide sequence can be directly determined, such as by mass spectroscopy, but such a method requires a large amount of each given polypeptide. Alternatively, the polypeptide can be tethered to its nucleic acid coding sequence by some method. Such methods based on tethering are generally referred to as biological display (e.g., phage display).

Phage display technology has been successful as providing a vehicle that allows for the selection of a displayed protein by providing an essential link between nucleic acid and the activity of the encoded polypeptide (for a review see, e.g., Clackson and Wells, 1994). In this case, filamentous phage particles act as genetic display and packages proteins on the outside of the particle and the genetic elements that encode them on the inside. However, phage display relies upon the creation of nucleic acid libraries in vivo in bacteria and this places a limitation on library size that can be used. Additionally, all potentially useful candidate polypeptides are fused to phage sequences for display and such fusion may interfere with the ability of the polypeptide function. Thus, there remains no efficient system for screening and identification of biologically active polypeptide molecules.

SUMMARY OF THE INVENTION

The methods detailed herein address a significant deficiency in polypeptide screening systems by providing a highly efficient system for identifying polypeptides that are able to provide a biological response in a living cell. The system allows effective separation of individual members of a polypeptide library, both during synthesis of the library and testing of cells by providing the components in individual microcapsules (e.g., through use of an emulsion system). Following exposure of the cells to the library, the nucleic acid sequences encoding the library polypeptides can remain bound to the test cells (or a component of the test cells), thereby associating a biological response in a cell with a molecule that provides the sequence of a biologically active polypeptide.

Thus, in a first embodiment, a method is provided of isolating a nucleic acid molecule encoding a biologically active polypeptide having a desired biological activity, the method comprising the steps of (a) obtaining a library of polypeptide molecules comprising at least 50,000 different molecules; (b) individually testing the different polypeptide molecules on live test cells for a biological response to the polypeptide molecules; and (c) identifying the sequences of nucleic acid molecules encoding the subset polypeptide molecules that are biologically active. For example, in some aspects, the library comprises at least 50,000, 100,000, 200,000, 500,000, 1 million, 10 million, 100 million or 1 billion different molecules (e.g., between about 50,000 and 2 million; 500,000 and 1.5 million; 1 million and 2 million; 5 million and 20 million; 50 million and 200 million; or 200 million and 1 billion different molecules). In certain aspects, a library of the embodiments encodes polypeptides having a wide range of net charge, such as from about −30 to +30, −20 to +20, −10 to +20 or −5 to +10 (e.g., between about −5 and +14). In still further aspects, a library of the embodiments encodes polypeptides having a diversity of hydrophobicity such as polypeptides comprising from about 1% to about 80% hydrophobic amino acid positions (e.g., between about 5% and 70%, 5% and 60% or 10% and 50% hydrophobic residues).

In some aspects, individually testing the different polypeptide molecules comprises individually testing the different polypeptide molecules on single cells or on about 5-500, 500-1,000, 1,000-5,000, 5,000-30,000, 30,000-50,000, 5-100, or 10-50 live cells. In further aspects, individually testing the different polypeptides can comprise testing the molecules on cells (or populations of cells) isolated in a gel, a well (e.g., of a microtiter plate), a tube or in a microcapsule of an emulsion. In some aspects, to achieve individual testing the different polypeptides, each isolated cell or cell population is contacted with, on average, one of the different polypeptide molecules (e.g., in a emulsion of microcapsules comprising on average one different polypeptide per microcapsule). In still further aspects, the testing of the embodiments is performed at concentration of at least 10,000 (e.g., at least about 15,000, 150,000, 1,500,000, 15 million or 150 million) distinct polypeptide library members per 1 mL of test volume and wherein the distinct polypeptides are comprised in separate microcapsules of an emulsion.

In a related embodiment a method is provided for isolating a nucleic acid molecule encoding a biologically active polypeptide having a desired biological activity, the method comprising the steps of (a) obtaining a population of nucleic acid molecules comprising sequences that encode polypeptides, wherein individual members of the population encode different polypeptides; (b) incubating the nucleic acid molecules under conditions that permit expression of polypeptides, wherein a population of polypeptide molecules is expressed from the nucleic acid molecules of the nucleic acid population, and each polypeptide molecule is associated with at least one copy of the nucleic acid molecule that encodes it; (c) testing cells for a biological response to individual member polypeptides of the population; and (d) isolating nucleic acid molecules associated with polypeptides that exhibit a biological response in the cells, to provide the nucleic acid molecule encoding the biologically active polypeptide.

Thus, in a further embodiment a polypeptide library is provided comprising a plurality of carrier particles wherein each particle comprises (a) one or more copies of a distinct nucleic acid molecule associated with the particle by a first binding moiety; and (b) a plurality of polypeptide molecules encoded by the distinct nucleic acid molecule, wherein each of said plurality of polypeptides is associated with the particle by a second binding moiety. For example, in some aspects, a library comprises at least about 0.1, 1, 10, 100, 1,000 million or 5 billion carrier particles. In certain aspects, each of the carrier particles comprises 10, 100, 1,000, 10,000 100,000, 500,000, 1,000,000, 5,000,000, 10,000,000, 20 million, 50 million or more copies of the distinct nucleic acid molecule (e.g., between about 0.5-50 million, 0.5-10 million or 0.5-5 million copies of the molecule). Thus, in some aspects, each of the carrier particles comprises a plurality of polypeptide molecules, such as between about 1-10 million, 20-500 million, 0.01-1 billion, 0.05-0.5 billion, 10-50 billion, 1-20 billion or 1-10 billion polypeptide molecules (e.g., more than about 10 million copies of the polypeptide molecule). In still further aspects, a library of the embodiments can be further defined by its diversity, for instance, a library can comprise between about 50,000 and 500,000, 5,000,000 or 5,000,000,000 distinct nucleic acid molecules. In still further aspects, the carrier particles of the library are comprised in microcapsules, such as the microcapsules of an emulsion (e.g., an emulsion comprising on average one carrier particle and distinct nucleic acid molecule per microcapsule).

In a further embodiment, there is provided a method for isolating a nucleic acid molecule encoding a biologically active polypeptide having a desired biological activity. In general such a method can comprise the following steps:

(a) obtaining a population of nucleic acid molecules comprising sequences that encode polypeptides, wherein individual members of the population encode different polypeptides;

(b) preparing a first population of microcapsules comprising (i) nucleic acid molecules of the nucleic acid population from (a); (ii) components for expression of the polypeptides; and (iii) a binding moiety associated with the nucleic acid, wherein individual members of the microcapsule population incorporate distinct members of the nucleic acid population;

(c) incubating the first population of microcapsules to permit expression of polypeptides;

(d) obtaining a second population of microcapsules that comprise test cells;

(e) fusing the first and second population of microcapsules to provide a third population of microcapsules, wherein individual members of the third population comprise an expressed polypeptide, nucleic acid molecules encoding the expressed polypeptide and the test cells and wherein the nucleic acid molecules encoding the polypeptides are bound to the test cells or a component of the test cells by virtue of the binding moiety (of step b-iii);

(f) testing the test cells for a biological response to the polypeptide; and (g) isolating nucleic acid molecules bound to the test cells or the component of the test cells exhibiting the biological response, to provide the nucleic acid molecule encoding the biologically active polypeptide.

In still a further embodiment there is provided a method for isolating a nucleic acid molecule encoding a biologically active polypeptide having a desired biological activity. In general such a method can comprise the following steps:

(a) obtaining a population of nucleic acid molecules comprising sequences that encode polypeptides, wherein individual members of the population encode different polypeptides;

(b) preparing a first population of microcapsules comprising (i) nucleic acid molecules of the nucleic acid population; (ii) components for expression of the polypeptides; (iii) a first binding moiety associated with the nucleic acid molecules and a carrier (e.g., a bead); and (iv) a second binding moiety associated with the nucleic acid molecules, wherein individual members of the microcapsule population incorporate distinct members of the nucleic acid population;

(c) incubating the first population of microcapsules to permit expression of polypeptides wherein expressed polypeptides are bound by said second binding moiety to form polypeptide-nucleic acid complexes;

(d) obtaining a second population of microcapsules that comprise (i) test cells; and (ii) the polypeptide-nucleic acid complexes;

(e) testing the test cells for a biological response to the polypeptide; and (g) isolating nucleic acid molecules bound to the component of the test cells exhibiting said response, to provide the nucleic acid molecule encoding the biologically active polypeptide.

In a further aspect, a method of the embodiments comprises:

(a) obtaining a population of nucleic acid molecules comprising sequences that encode polypeptides, wherein individual members of the population encode different polypeptides;

(b) preparing a first population of microcapsules comprising (i) nucleic acid molecules of the nucleic acid population; (ii) components for expression of the polypeptides; (iii) a first binding moiety associated with the nucleic acid molecules and a carrier (e.g., a bead); and (iv) a second binding moiety associated with the nucleic acid molecules, wherein individual members of the microcapsule population incorporate distinct members of the nucleic acid population;

(c) incubating the first population of microcapsules to permit expression of polypeptides wherein expressed polypeptides are bound by said second binding moiety to form polypeptide-nucleic acid complexes;

(d) breaking the microcapsules (and, optionally performing one or more wash) and isolating the polypeptide-nucleic acid complexes associated with a carrier (e.g., the isolation/wash can be performed such that components for expression are removed but the nucleic acid molecules and polypeptide molecules expressed from those same nucleic acid molecules remain linked via the carrier);

(e) preparing a second population of microcapsules that comprise (i) test cells; and (ii) the polypeptide-nucleic acid complexes;

(f) testing the test cells for a biological response to the polypeptide; and (g) isolating nucleic acid molecules bound to the test cells or the component of the test cells exhibiting the biological response, to provide the nucleic acid molecule encoding the biologically active polypeptide.

In still further aspects of the embodiments the second or further population of microcapsules comprises (i) test cells;

(ii) the polypeptide-nucleic acid complexes; and (iii) at least a first dissociating agent, which can dissociate the polypeptide from the carrier (e.g., such that the polypeptide diffuses freely in solution). The type of dissociating agent used can depend, for example, on the binding moiety that binds to the polypeptide to the nucleic acid and/or carrier. For example, in some aspects, the binding moiety is a peptide binding moiety (e.g., a peptide that formed part of the expressed polypeptides in the library) in such aspects the dissociating agent can be a proteinase that cleaves the peptide binding moiety. In still further aspects, the second population of microcapsules further comprises a second dissociation agent, which can dissociate the nucleic acid molecules from the carrier.

Thus, a first step in a method of the embodiments can comprise (a) obtaining a nucleic acid population of nucleic acid molecules comprising sequences that encode polypeptides, wherein individual members of the population encode different polypeptides. While the nucleic acid molecules can be RNA, in preferred aspects, they are DNA molecules. The nucleic acid molecules can comprise sequence segments encoding, for example, an open reading frame (ORF) for a polypeptide; one or more primer binding site(s); a polymerase promoter sequence; and/or a polymerase terminator sequence. The ORF itself, which encodes the polypeptides of the library, can comprise sequences that are randomized, cDNA (or genomic DNA) sequences or portions thereof (e.g., from an organism, such as a human) or a mixture of such sequences. In some cases, the ORF further comprises a sequence encoding a membrane translocation domain and/or a nuclear translocation domain. In further aspects, these nucleic acid molecules comprise a label, such as a detectable tag (e.g., a fluorescent tag) or an affinity tag (e.g., biotin). In preferred aspects, the nucleic acid molecules are immobilized on beads, such as magnetic beads, polymer microspheres (e.g., via a biotin-streptavidin interaction or an amine linkage). Furthermore, the nucleic acid molecules, beads or both can be bound to a cell-binding moiety, such as Annexin V, an antibody, or a lectin.

A second step of a method of the embodiments can then comprise (b) preparing a first population of microcapsules, wherein the microcapsules comprise (i) nucleic acid molecules of the nucleic acid population described above; (ii) components for expression of polypeptides encoded by the nucleic acids; and (iii) a first binding moiety associated with the nucleic acid molecules and a carrier (e.g., a bead); and (iv) a second binding moiety associated with said nucleic acid molecules (e.g., a second binding moiety associated with the nucleic acid molecules via the carrier). Accordingly, in some aspects, a microcapsule in the first population comprises distinct nucleic acid molecules of the nucleic acid population associated (by a first binding moiety) to a carrier, wherein the carrier comprises or is associated with a second binding moiety. In certain preferred aspects, each carrier comprises a plurality of the nucleic acid molecules, such as about or at least about 10,000 100,000, 500,000, 1,000,000, 5,000,000, 10,000,000, 50,000,000 or more copies of the molecules. Thus, individual members of the microcapsule population can incorporate distinct members of the nucleic acid population. As used herein a "microcapsule" can be, for example, a reverse micelle in an emulsion or a bilayered or multilayered lipid vesicle. In certain preferred aspects, the "microcapsule" can be an aqueous droplet suspended in oil and stabilized with one or more surfactants. These microcapsules comprise components for expression of the polypeptides such as components for transcription and translation. For example, the components can comprise an RNA polymerase (e.g., a T7 or SP6 RNA polymerase) and factors required for RNA polymerase activity. Furthermore, the microcapsules can comprise ribosomes (e.g., eukaryotic or prokaryotic ribosomes) and translation factors required for protein synthesis. For example, the microcapsules can comprise an extract from a translation competent cell lysate, such as bacteria (e.g., a E. coli bacterial lysate), yeast or mammalian cell lysate (e.g., a rabbit reticulocyte lysate or wheat germ extract), buffer (e.g. HEPES), reducing agent, such as dithiothreitol (e.g. to stabilize the T7 RNA polymerase), nucleotides, folinic acid, tRNAs (such as E. coli tRNAs), salts (e.g. magnesium, potassium, ammonium), glucose, cyclic AMP, creatine phosphate, creatine kinase, protease inhibitors, RNase inhibitors, amino acids, and inhibitors of RNA polymerase (e.g., rifampicin).

As discussed above, in certain aspects, the nucleic acid molecules are associated with a carrier. As used herein, a "carrier" can be, for example, a microsphere, a bead, a nanoparticle, a macromolecule, a molecule, a microfabricated structure, or a nanostructure. The first and/or second binding moiety can be, without limitation, an antibody, an aptamer, a lectin, a polypeptide, a receptor protein, a ligand, a carbohydrate, or a metal-charged chelating group capable of binding a tagged protein (e.g. nickel-nitrilotriacetic acid capable of binding histidine-tagged proteins). In some cases, a binding moiety as used here refers to one half of a binding pair (e.g., the streptavidin or biotin of a streptavidin-biotin binding pair). The linkage between a binding moiety and the carrier can be, without limitation, thiol, amino, carboxylate, hydroxylate, histidine-tagging (e.g., hexahistidine tagging), or biotin-streptavidin. For example the carrier can be a cross-linked agarose bead functionalized with a nickel-charged chelating group capable of binding histidine-tagged proteins. Alternatively, the carrier can be a silica bead functionalized with nickel-nitrilotriacetic acid, or a streptavidin-coated polystyrene or silica bead pre-loaded with nickel-charged biotin-nitrilotriacetic acid. Such a bead (agarose, polystyrene, or silica) can, for instance, be incubated with histidine-tagged streptavidin molecules at a concentration where a fraction of the histidine-tag binding sites will be occupied by streptavidin molecules (e.g., in this case the nucleic acid molecules can have a biotin-tag, which can bind the streptavidin molecules on the agarose bead to provide a linkage between the nucleic acid and the carrier). Likewise, in some aspects, an expressed polypeptide can comprise a histidine-tag, such that the expressed polypeptide molecules can bind to a fraction of the remaining histidine-tag binding sites on the bead to provide a linkage between the polypeptide and the carrier (and the nucleic acid molecule(s)).

As indicated supra, in some cases, a further binding moiety (e.g., a third binding moiety) is associated with the nucleic acid molecules of a library. Such a binding moiety can be, without limitation, an antibody, an aptamer, a lectin, a polypeptide, a receptor protein, a ligand or a carbohydrate. For example, the binding moiety can bind to a component, such as a protein, on the surface of a cell, or with-in a cell, or secreted by a cell, or released by a cell. In some aspects, the binding moiety can bind to test cells (or a component of the test cells) only when the test cells exhibit a biological response to a polypeptide encoded by the library. For example, the binding moiety can be an annexin polypeptide that binds to test cells only when the test cells are undergoing apoptosis. In a further example, the further binding moiety can bind to an intracellular component and thereby only bind its target when cell lysis has occurred. For example, the intracellular component can be a protein (e.g., a protein expressed by the cell as a transgene). For instance, in the case of an assay to screen for an anti-microbial polypeptide (e.g., a polypeptide that causes cell lysis of *E. coli*) an active peptide can be detected by (i) expressing maltose binding protein with a histidine-tag in test cells, and (ii) using a nickel-charged chelating group as a binding moiety to capture the histidine tag of the maltose binding protein that is released from test cells that are lysed. Thus, in some aspects, cells can be tested for a biological response to a polypeptide by determining whether the nucleic acid molecules (attached to the binding moiety) are bound to the test cells. In certain preferred aspects, the further binding moiety can be bound to nucleic acid molecules directly (not via the carrier).

In a third step a method of the embodiments can comprise (c) incubating the first population of microcapsules to permit expression of polypeptides. As indicated above, the microcapsules can comprise the components required for translation and/or transcription. Thus, incubating the microcapsules may comprise applying conditions to the microcapsules that favor expression, such as heating or cooling the microcapsules to a temperature where the enzymes that mediate transcription and/or translation are most active.

In still further aspects of the embodiments, a carrier or bead of the embodiments comprises a second population of nucleic acid molecules that encodes a second population of polypeptides. Accordingly, in certain aspects, when both a first nucleic acid population and a second nucleic acid population are provided, both populations can be expressed simultaneously to produce a first and second population of polypeptides associated with the carriers. In some aspects, all of the members of the second population of nucleic acids (and encoded polypeptides) are essentially identical, for example encoding a cofactor for use in testing cells. One example of such a system is a method of screening a first population of the nucleic acid molecules encoding a library of candidate antagonist polypeptides. In this case, the second population of nucleic acid molecules can each encode an agonist polypeptide and cells can be tested to identify nucleic acid molecules (from the first population) that encode polypeptides, which effectively block the agonist activity of the polypeptide encoded by the second population of nucleic acids.

In some aspects, a fourth, optional, step of the instant methods can comprise (d) breaking the microcapsules and performing a wash such that components for expression are removed but where the nucleic acid-polypeptide complexes (comprising expressed polypeptide molecules and the nucleic acids encoding the polypeptides) remain linked via the carrier. Preferably, the carrier can be isolated from a washing buffer, such that the carrier can be reformulated at a desired volume density or concentration after the wash. Isolation can be, without limitation, achieved using magnetic force, centrifugal force, dialysis, or column purification. For example, a carrier/nucleic acid-polypeptide complex (e.g., a cross-linked agarose bead, a silica bead or a polystyrene bead) can be washed by: (i) dispensing the carrier suspension into a tube, (ii) subjecting the tube and its contents to centrifugation, (iii) replacing the supernatant with a washing buffer, and repeating steps (ii) and (iii), until the desired level of purity has been reached.

In a fifth step, a method of the embodiments can comprise obtaining or formulating a second population of microcapsules that comprise test cells. Preferably, the test cells are living cells or comprise a significant proportion of living cells. These cells can be prokaryotic cells or eukaryotic cells, such as fungal cells (e.g., yeast cells), plant cells, insect cells, mammalian cells or archaeal cells. For example, cells for use herein can comprise human cells, such immune cells, neuronal cells, hepatocytes, cardiomyocytes, embryonic stem cells, induced pluripotent stem (iPS) cells or cancer cells. Such cells can be, without limitation, primary cells or immortalized cells (e.g., from an established cell line), cells normally grown adherent to a surface or in suspension and, in some cases, the cells are transgenic cells. In some preferred aspects, the second population of microcapsules comprise, on average 1, 1-100, 100-500, 500-5000, 5,000-30,000, 30,000-50,000 or 5-50 cells per microcapsule (or per micro-well).

Thus, in some aspects, a method of the embodiments can comprise preparing a second population of microcapsules, wherein individual members of the second population comprise an expressed polypeptide, nucleic acid molecules encoding the expressed polypeptide and the test cells, e.g., where the polypeptide and nucleic acid molecules are both linked to the same carrier. In some preferred aspects, the second population of microcapsules comprise, on average one carrier per microcapsule. In certain aspects, the nucleic acid molecules encoding the polypeptides in this second population of microcapsules are associated with the test cell or a component of the test cells by virtue of a further binding moiety. In certain preferred aspects, when the binding moiety is linked directly to the nucleic acid molecules, a second dissociation agent can be provided that will dissociate the nucleic acid molecules from the carrier, such that the nucleic acid molecule will bind the test cell or a component of the test cells by virtue of the further binding moiety, where the carrier is no longer associated with the nucleic acid molecules.

In still further aspects, a second microcapsule population of the embodiments can be produced by fusing the first population of microcapsules with a population of microcapsules comprising the test cells. Fusions of microcapsules to form the second population can be accomplished in a variety of ways. For example, the one or both of the microcapsule populations for fusion can comprise an affinity tag on their outer surface. For example, the first population of microcapsules can comprise an affinity tag (e.g., biotin) that specifically interacts with an affinity tag on microcapsules comprising the test cells (e.g., avidin). In this case, fusion can be assisted by the interaction of the affinity tags (affinity assisted coalescence). Fusion of the microcapsules can further comprise applying an electrical field to the microcapsules. For example, the populations of microcapsules can be fused by use of electrocoalescence. In some aspects, both of these methods may be applied and fusion can be mediated by affinity-assisted electrocoalescence. In some cases, populations of microcapsules are fused at a ratio of about 10:1, about 5:1 or about 2:1. For example, in some aspects, fusion is performed such that, on average one member (and only one member) of the first population of microcapsules is fused with one microcapsule (and only one microcapsule) comprising test cells.

In still further embodiments, a library of polypeptides in accordance with the embodiments can be tested for an activity or response against a target molecule (i.e., other than a living cell). Thus, in some aspects, a method of isolating a nucleic acid molecule encoding an active polypeptide having a desired activity comprises: (a) obtaining a population of nucleic acid molecules comprising sequences that encode polypeptides, wherein individual members of the population encode different polypeptides; (b) incubating the nucleic acid molecules under conditions that permit expression of polypeptides, wherein a population of polypeptide molecules is expressed from the nucleic acid molecules of the nucleic acid population, and each polypeptide molecule is associated with at least one copy of the nucleic acid molecule that encodes it; (c) testing a target molecule for a response to individual member polypeptides of the population; and (d) isolating nucleic acid molecules associated with polypeptides that provide a response to the target molecules, to provide the nucleic acid molecule encoding the active polypeptide. For example, the target molecule can be a polypeptide or polypeptide complex, such as an enzyme, a receptor or an antigen. Accordingly, testing a polypeptide for a response can comprise testing for binding of the target molecule to a member polypeptide; inhibition of binding of the target molecule to a ligand (e.g., an agonist or antagonist); inhibition of an enzymatic activity of the target molecule; or activation of an enzymatic activity of the target molecule. In further aspects, testing a target molecule for a response to individual member polypeptides comprises testing the individual member polypeptides in a gel, a well of micro titer plate or a microcapsule of an emulsion. For example, the target molecules can be bound to or otherwise immobilized in a gel compartment or a well of the micro titer plate.

As indicated supra, in some cases, at least a first dissociation agent is provided in the second population of microcapsules, which allows a significant portion of the polypeptides to be dissociated from the carrier and nucleic acid molecules. Such a dissociation agent can be, without limitation, an enzyme, a protease, an endonuclease, a catalyst or an elution agent (e.g., imidazole). For example, the dissociation agent can be the Tobacco Etch Virus (TEV) protease and the expressed polypeptide can have, in addition to test sequence and the histidine-tag described above, the recognition site for the TEV protease (i.e., Glu-Asn-Leu-Tyr-Phe-Gln-[Gly/Ser]). In this aspect, the TEV protease can then cleave the polypeptide sequence and thus dissociate the polypeptide from the carrier such that the polypeptide diffuses freely in solution.

In a sixth step, a method of the embodiments can further comprise, (f) testing the test cells for a biological response to the polypeptide. Testing the cells can involve, for instance, detecting a change in the optical or fluorescent properties of the test cells, such as by detecting uptake or exclusion of a fluorescent dye by the cells or by detecting the binding of a labeled reagent, or by expression of a reporter protein (e.g., a fluorescent protein). Alternatively, in some aspects, binding of a labeled reagent can be detected by magnetic or affinity separation. Furthermore, the testing of the test cells may, in some cases, involve the detection of a soluble factor secreted or released by the cells. For example, testing cells can comprise detecting the binding of an antibody, an aptamer, a lectin, a polypeptide, a receptor protein, a ligand or a carbohydrate to the test cells or a component thereof. Thus, in some cases, detection of such binding can comprise detecting binding of the further binding moiety associated with the nucleic acid molecules of the library. Alternatively, testing the cells can comprise detecting the product of an enzymatic reaction. Thus, in some cases, the biological activity may result in release or cell surface-presentation of an enzyme that can convert a substrate to a product, where the product is detectable by some method (e.g., fluorescence or luminescence). For example, a reporter cell line may, as a result of the biological activity, express a luciferase enzyme that has a secretion tag. In the case of a bead tethered to a luciferin substrate, the secreted enzyme can turn the substrate into a luminescent product, which can be detected. Testing the cells can be completed while the cells are in a microcapsule (e.g., within an emulsion) or micro-well or after the cells are removed from the micro-well or microcapsule (e.g., by breaking an emulsion).

A huge array of biological responses can be tested according the methods of the embodiments. In some aspects, the biological response can be a change in cell proliferation; a change in the expression in the cell; a change in the compartmentalization of a marker inside the cell; a change in cell phenotype; a change in cell function; permeability of a polypeptide through an epithelial layer; a change in the markers expressed on the cell surface; a change in a response to a drug; differentiation; de-differentiation (i.e., enhanced pluripotency); or cell death (e.g., via necrosis or apoptosis). In the case of apoptosis, for instance, detecting a response can comprise detecting Annexin V binding to the test cell. Likewise, in the case of cell differentiation detecting a response can comprise detecting the expression of a differentiation marker. In some cases, a test cell can comprise a transgene such as a transgene for the expression of a reporter (e.g., a fluorescent protein) and detecting a biological response can comprise detecting expression of the reporter.

In a seventh step, a method of the embodiments can comprise (g) isolating nucleic acid molecules associated with (e.g., bound to) test cells exhibiting the response, to provide the nucleic acid molecule encoding the biologically active polypeptide. For example, isolating nucleic acid molecules bound to test cells can be by affinity purification and/or magnetic purification of test cells or by fluorescence activated cell sorting (FACS) of the cells (or the microcapsules comprising test cells). In some aspects, isolating the nucleic acids can involve a step for affinity purification of the carrier bound to the nucleic acids (e.g., purification using a magnetic column). Once, the nucleic acid molecules have been isolated these sequences can be subjected to further analysis. For example, the nucleic acids can be amplified, sequenced, cloned and/or expressed. In certain aspects, isolating a nucleic acid associated with test cells comprises isolating nucleic acids that are bound non-specifically to test cell. In other aspects, nucleic acid molecules are bound to test cells specifically (e.g., by a binding moiety attached the nucleic acid molecules).

In yet a further embodiment a library in accordance with the embodiments is provided. In some aspects, a library comprises a plurality of individual cell complexes, each complex of the library comprising a cell associated with one or more beads, the cell comprising a recombinant polypeptide (or a plurality of copies of the same recombinant polypeptide) and the bead or beads bound to nucleic acid molecules that encode the recombinant polypeptide, wherein individual cell complexes of the library comprise a different recombinant polypeptide. For example, in some aspects, the recombinant polypeptide of the complex is comprised in the cell (e.g., in the cell membrane, cytosol or nucleus of the cell). In some aspects, the recombinant polypeptide and/or the bead(s) are bound to the surface of the cell. A cell for use in a library of the embodiments may be any of the cells contemplated herein, such as a mammalian or bacterial cell and preferably is a viable cell. In some aspects, the bead or beads of the complexes comprise a first binding moiety for binding the nucleic acid molecules and/or a second binding moiety for binding the recombinant polypeptide molecules.

In still further aspects, cell complexes of a library of the embodiments comprising different recombinant polypeptides are isolated from one another, such as by compartmentalization in a gel, a well of a micro titer plate or a microcapsule of an emulsion. Thus, in some aspects, each compartment of the library comprises 30,000-50,000, 1,000-

5,000, 5-500, 5-100, or 10-50 cells. In certain aspects, a library of the embodiments comprises at least 10,000 distinct complexes comprising a different recombinant polypeptide (e.g., between about 50,000 and 500,000, 5,000,000 or 5,000,000,000 distinct complexes). In still further aspects, each complex of a library (or each compartment comprising a complex) comprises at least about 100 million copies of the recombinant polypeptide (e.g., between about 1-10 million, 20-500 million, 0.01-1 billion, 0.05-0.5 billion, 10-50 billion, 1-20 billion, or 1-10 billion copies of the recombinant).

In yet a further embodiment, a carrier bead is provided comprising a functionalized surface bound to 1-10 million nucleic acid molecules and 1-20 billion polypeptide molecules. Beads for use according to the embodiments include, for instance, magnetic beads, cross-linked agarose beads, polystyrene beads, silica beads, microparticles and microspheres. Beads can have, with limitation, an average diameter of about 1-100 or 5-80 nm. In some cases, a bead can comprise at least 5, 10 or 15 billion polypeptide molecules and/or at least 5, 10, or 15 million nucleic acid molecules. In certain aspects, the nucleic acid molecules are bound to the bead by a biotin-avidin interaction. In still further aspects, the polypeptide molecules are bound to the bead by the binding of charged Ni groups on the bead by His tag sequences of the polypeptide molecules. In some cases, the nucleic acid molecules and/or the polypeptide molecules on the bead all comprise essentially identical sequences. In still further aspects, the polypeptide molecules bound to the bead(s) are encoded by the nucleic acid molecules bound to the bead. Thus, in still a further embodiment, library is provided comprising a plurality of beads in accordance with the embodiments wherein each bead is bound to nucleic acid molecules (and polypeptide molecules) comprising a unique sequence relative to the other beads of the library. For example, the library can comprise about 50,000 to 15 million beads bound to different nucleic acid sequences (e.g., at least or at most about 15,000, 150,000, 1,500,000, 15,000,000, million or 150,000,000 million beads bound to different nucleic acid sequences). In further aspects, the library has a concentration of at least 10,000, 20,000, 30,000 40,000 or 50,000 distinct polypeptide library members per 1 mL of volume.

In still a further embodiment there is provided an emulsion microcapsule comprising an expressed polypeptide, recombinant nucleic acid molecules encoding the expressed polypeptide and cells, wherein the recombinant nucleic acid molecules encoding the polypeptides are bound to the test cell by virtue of a binding moiety that is associated with the recombinant nucleic acid molecules. In certain aspects, the emulsion microcapsule may further comprise one or more beads (e.g., bound to the nucleic acid molecules and/or the binding moiety), a label (such as fluorescently labeled molecule) and/or a cell growth medium. In further aspects, the polypeptide comprises a segment of sequence encoding a membrane translocation domain. Thus, in some aspects, the polypeptide is comprised in the test cell.

In still a further embodiments there is provided an isolated cell wherein the cell comprises recombinant nucleic acid molecules bound to the surface of the cell by virtue of a binding moiety that is associated with the recombinant nucleic acid molecules. For example, in some aspects, the recombinant nucleic acid molecules encode a polypeptide and the cell comprises the encoded polypeptide. In still further aspects, the recombinant nucleic acid molecules and binding moiety are further bound to a bead (e.g., a bead comprising a label).

In certain aspects, a cell of the embodiments is a living cell. In some aspects, the cell is a prokaryotic cell or eukaryotic cell, such as a fungal cell, plant cell, insect cell or mammalian cell. In still further aspects, the cell is a human cell, such an immune cell, a neuronal cell, an embryonic stem cell, an induced pluripotent stem cell or a cancer cell. In yet further aspects, the cell is a primary cell or an immortalized cell (e.g., from an established cell line).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-F: A schematic showing the steps of an example protocol in accordance with the embodiments. In this example, "hits" are collected by FACS.

FIG. 2A-F: A schematic showing the steps of an example protocol in accordance with the embodiments. In this example, "hits" resulting in test cell lysis are collect by affinity purification based on binding of a protein released from the lysed cells to the bead.

FIG. 3A-F: A schematic showing the steps of an example protocol in accordance with the embodiments. In this example, "hits" resulting surface expression of a marker on test cells are collect by affinity purification based on surface expression of the marker. In this example, nucleic acid molecules of the library are dissociated from beads and bound to test cells.

FIG. 4A-C: A schematic showing the steps of an example protocol in accordance with the embodiments. In this example, nucleic acid molecules of the library remain associated with their encoded polypeptides by isolation in separate microcapsules. Cells are tested with library polypeptides/nucleic acids by contacting isolated cells (of cell populations) with individual microcapsules comprising the library members.

FIG. 18A-B: (A) upper panel shows the amino acid sequence and corresponding nucleic acid sequence of Melittin from *Apis mellifera* (SEQ ID NOs: 16, 18, and 22). Positions that were diversified in the library based on the sequence are indicated. Lower panel shows three-dimensions diagrams of the Melittin polypeptides, with diversified positions indicated in dark gray (SEQ ID NOs: 17, 19, 21 and 23). (B) A schematic of the vector used for constructions of the diversified Melittin library (SEQ ID NO: 24).

DESCRIPTION OF ILLUSTRATIVE EMBODIMENTS

Detailed herein is a new system that allows for the efficient screening of highly diverse libraries of polypeptide molecules. The molecules can be screened not only for a binding affinity, but also for a biological activity on a living cell. Polypeptides that are identified to provide a desired biologically activity are conveniently associated with their nucleic acid coding sequence, which allows for a rapid determination of their structure. In accordance with one embodiment, a solution phase DNA library encoding the candidate polypeptides can be used. The library DNA molecule associated with the beads may be clonally amplified on the beads, which can also comprise a binding moiety, such as a polypeptide-binding moiety (e.g., using bead-based emulsion PCR). In some aspects, the library comprises a further binding moiety, e.g., on the solution-end of the DNA molecules. For example, the further binding moiety can be added during amplification using a tagged primer (e.g., a biotin-tagged primer). The emulsion can then be broken and the beads containing the DNA library purified.

Clonal expression of the bead-library can be achieved by creating emulsions containing a DNA coated bead with cell free transcription and translation systems. In this emulsion, expressed polypeptides can bind to a binding moiety on the bead, to generate polypeptide-nucleic acid complexes, such that expressed polypeptide remain associated with their coding nucleic acid molecules (and the beads). The emulsion can then be broken and the beads containing the DNA library along with expressed polypeptides purified. Testing of bioactivity can be accomplished by separately contacting the beads/polypeptide-nucleic acid complexes with cells, such that on average one bead/polypeptide-nucleic acid complex is placed in isolation with one or more test cells (e.g., in well, gel matrix or microcapsule). For instance, the testing can comprise creating an emulsion comprising the beads combined with the desired assay reagents such as test cells, assay reporting molecules, and a dissociation agent, such as a protease that can dissociate the polypeptide molecules from the bead. The microcapsules can then be directly screened for an effect on the encapsulated test cell, such as by using FACS, a colony picking system, magnetic bead collection or binding column or a combination thereof. Alternatively, the emulsion can be broken prior to assessing an effect on the test cell. In some cases, the DNA can be dissociated from the bead and bound to the test cells via the further binding moiety. Once cells demonstrating a given biological effect are identified the coding sequence for the candidate polypeptide can be easily determined by virtue of the coding DNA's binding to the test cell.

Figure 4A:
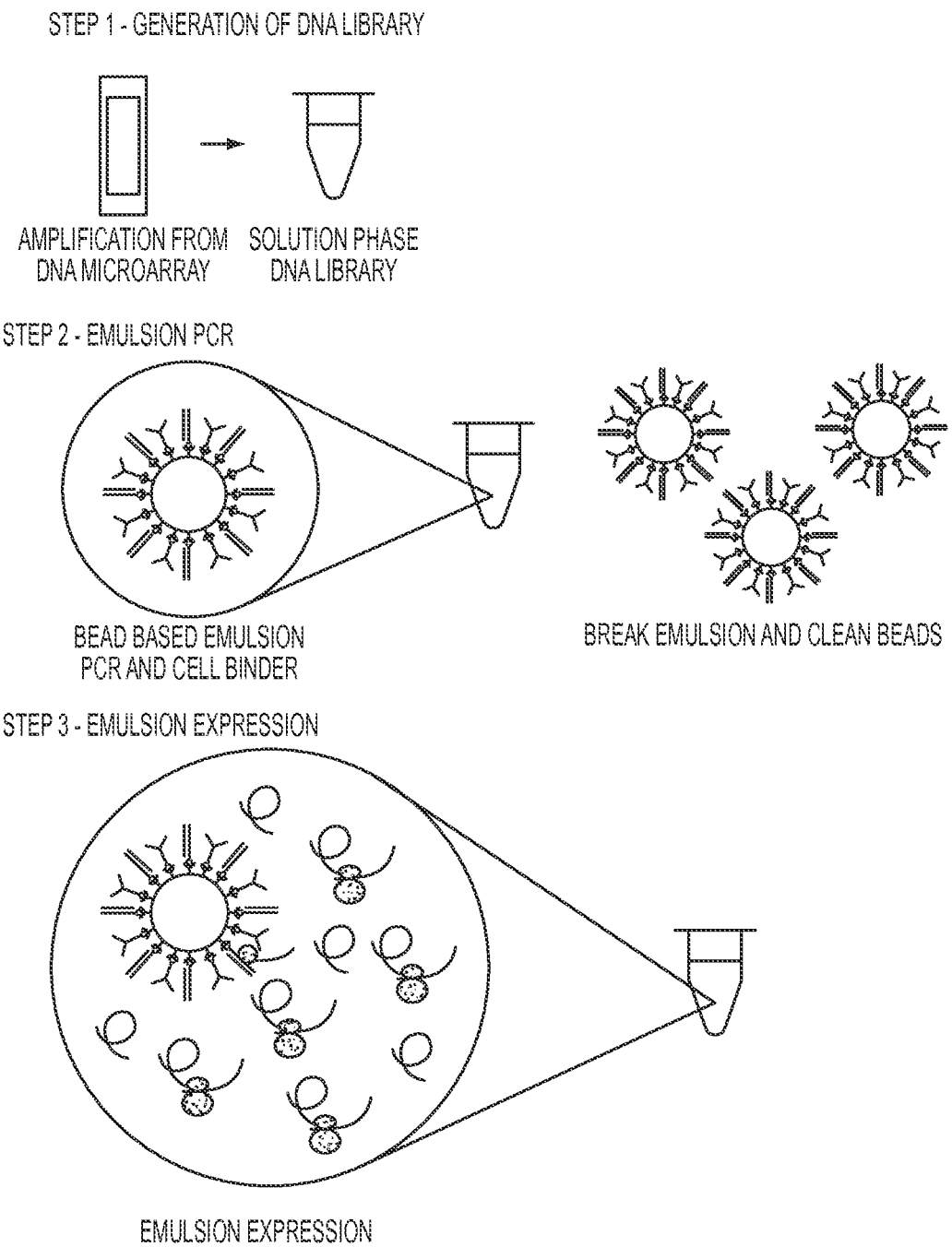

An overview of a polypeptide screening method of three alternative embodiments is graphically depicted in FIG. 1A-F, FIG. 2A-F, and FIG. 3A-F, respectively. In this example, step 1 involves generating a solution phase library of DNA molecules. For this step double stranded DNA (dsDNA) molecules are produced, which include a library of polypeptide coding sequences that will be screened, in addition to segments of sequence that allow expression of the polypeptide and amplification of the polypeptide coding sequence. Example of sequences used for library construction are shown in FIGS. 4B and 4C. In some cases, the sequences can be completely synthetic and the molecules can be chemically synthesized. In other cases, the dsDNA library is constructed using multiple segments of sequence (such as those depicted in FIG. 5B) that are individually synthesized or amplified. For example, the segments used in construction can include (i) a forward primer ("Basic Forward Primer") that includes primer binding sites and a polymerase promoter sequence, such as T7 promoter; (ii) a reverse primer ("Reverse Primer") that includes primer binding sites and a polymerase terminator sequence; and (iii) the library template ("DNA Library Template") that can include primer binding sites and the open reading frame (ORF) that encodes polypeptide sequences that constitute the library.

The library sequences themselves can be generated by a variety of methods that are well known to those of skill in the art. To touch on few such methods, the ORF for the library can be completely or partially composed of a randomized set of sequences (either by chemically synthesizing random sequence or by using error-prone amplification of a known sequence). In other cases, the library ORF sequences can be segments of genomic or cDNA sequences from an organism. For example, the ORF can be composed of segments of human cDNA. Regardless, of how the ORF sequences are produced, the library template will preferably include an ATG translation initiation codon that is optimized for prokaryotic or eukaryotic translation initiation and stop codon.

Figure 5A:
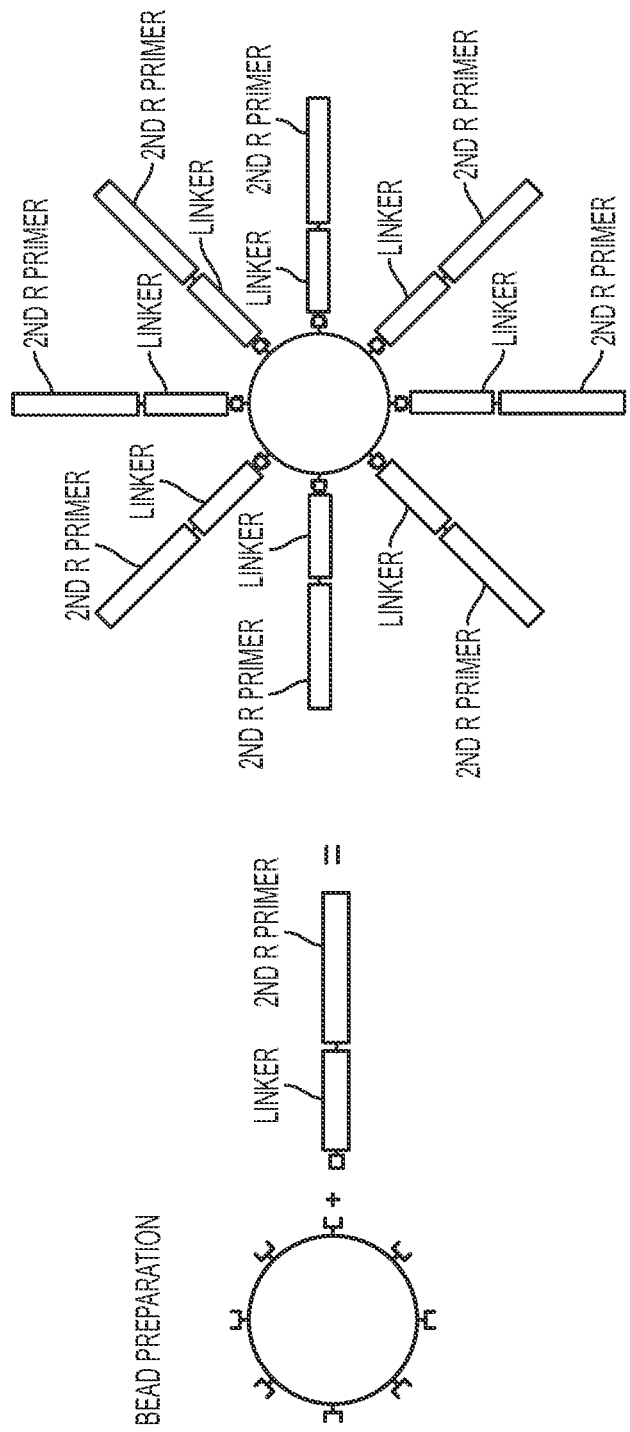
FIG. 5A-D: (A) An example of an initial bead preparation step in accordance with the embodiments. In this example, beads are coated with streptavidin and nucleic acid molecules including a biotin tag and segments of sequence including a linker and primer binding site. (B) A schematic of nucleic acid molecules that can be used in the construction a library according to the embodiments. (C) A schematic of nucleic acid molecules in an example library according to the embodiments. (D) A schematic showing an example emulsion PCR step in accordance with the embodiments.
Figure 5B:
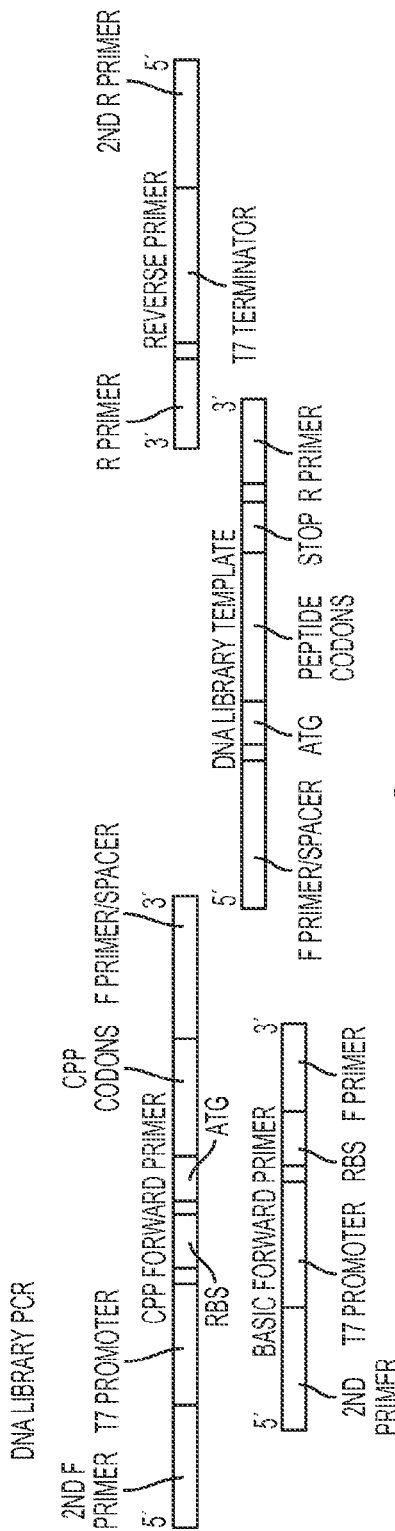

Other sequences can be included adjacent to the library ORF to optimize expression, such as an internal ribosome entry site (IRES) or a templated poly-A tail. Furthermore, as depicted in FIG. 5B, in certain aspects, a cell penetrating peptide is encoded by the assembled dsDNA library. In some cases the CPP coding sequence can be included on the forward primer segment ("CPP Forward Primer"), in other cases it can be included the reverse primer or on the library template itself. It will be recognized by a skilled worker that, in certain aspects, the library is engineered such that the CPP, when expressed, forms an amino- or carboxy-terminal fusion protein with the library ORF. In this case, it may be preferred to include a spacer coding sequence, such a sequence encoding a stretch of polyglycine residues between the CPP and the library ORF. In other aspects, the library ORF and CPP can be expressed as separate polypeptides, so long as the CPP is able to mediate membrane transit without being covalently linked to the ORF.

Figure 5C:
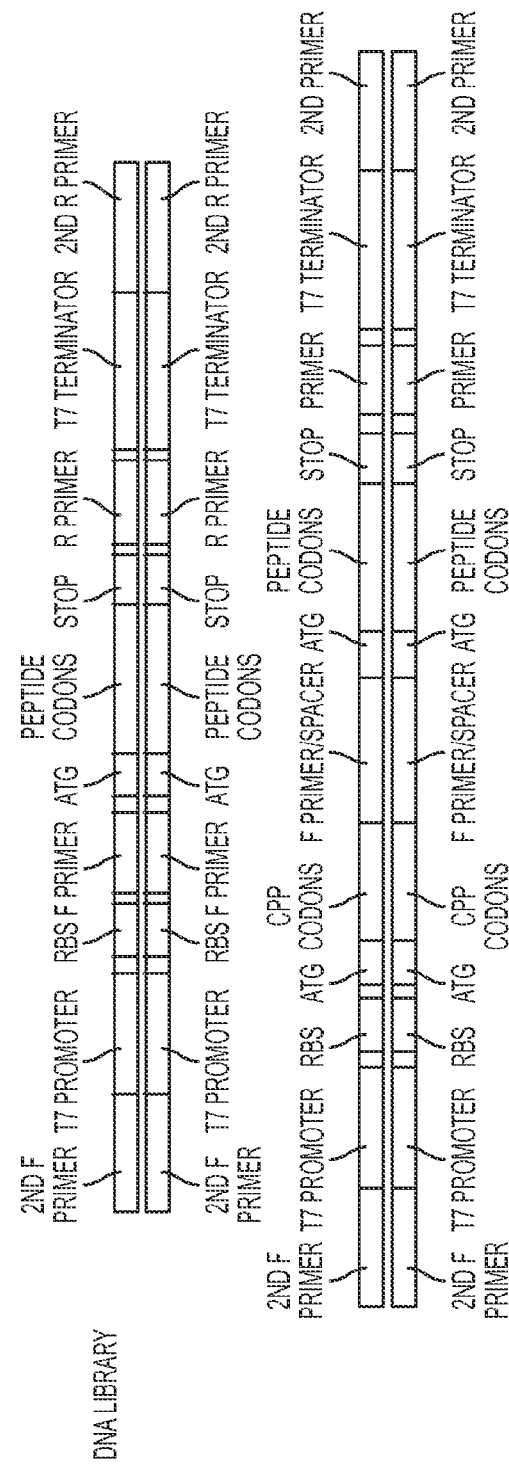
Figure 5D:
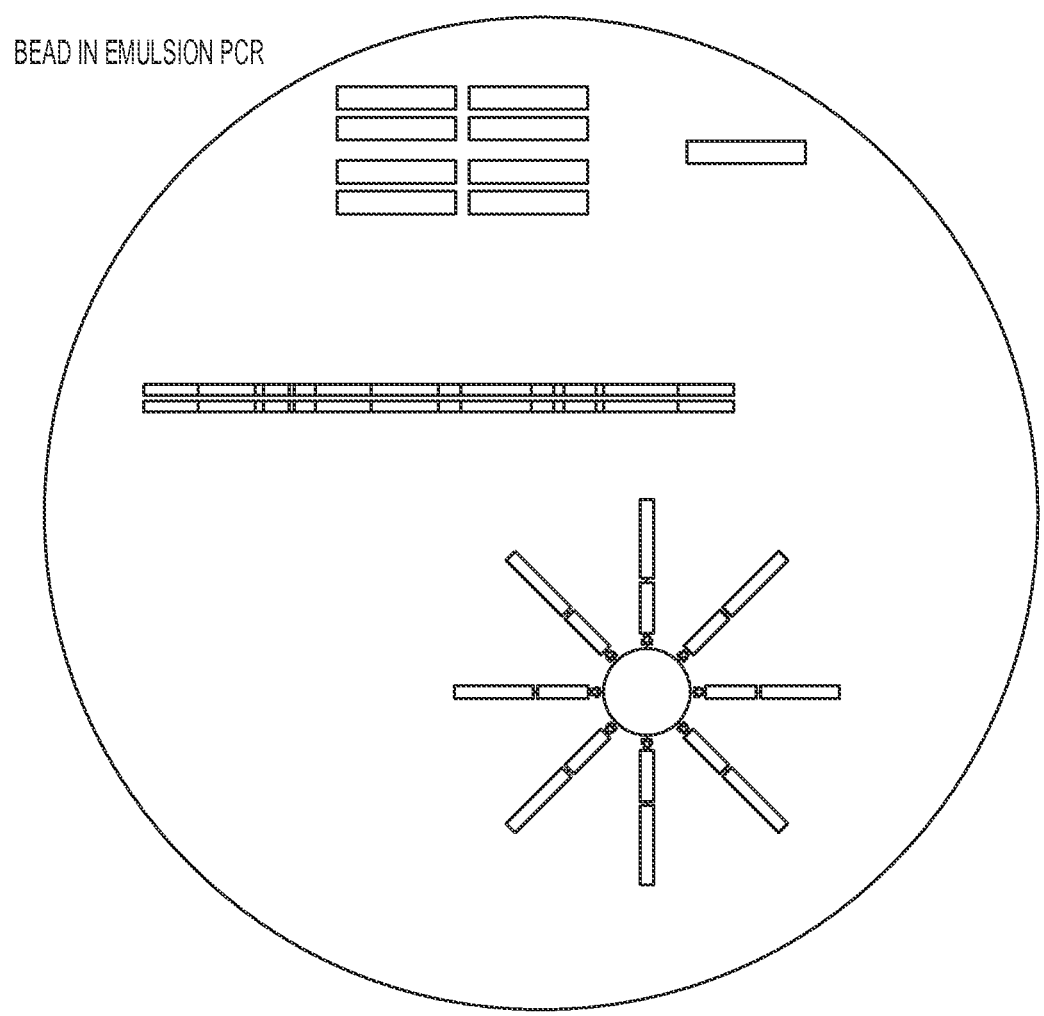

Examples, of constructed dsDNA libraries of the embodiments are shown in FIG. 5C. Both a library that encodes a polypeptide ORF alone and an ORF with a CPP are shown. In some aspects, these molecules can be purified following construction and prior to linkage with a bead, e.g., by size exclusion chromatography or gel purification.

Once constructed the DNA library can be immobilized such as on a bead. Examples of beads for use according to the embodiments are provided in FIG. 5A (and shown in FIG. 1-3). In general, the bead will include an affinity moiety that allows the bead to interact with a nucleic acid molecule. For instance, the bead may be a streptavidin-coated bead and a nucleic acid molecule for immobilization on the bead can include a biotin moiety. In some cases, each DNA molecule can include two affinity moieties, such as biotin, to further stabilize the DNA. Beads can include additional features for use in immobilizing nucleic acids or that can be used in a downstream screening or selection processes. For example, the bead may include a binding moiety (e.g., Annexin V), a fluorescent label or a fluorescent quencher. In some cases, the bead can be magnetic. To prepare the beads for addition of the library, the beads are coated with multiple copies of DNA molecules, as shown in FIG. 5A, thereby generating a population of beads that are each coated with a plurality of a identical DNA molecules that include a common primer binding sequence (i.e., a sequence that can anneal to sequences from the dsDNA library).

Figure 6:
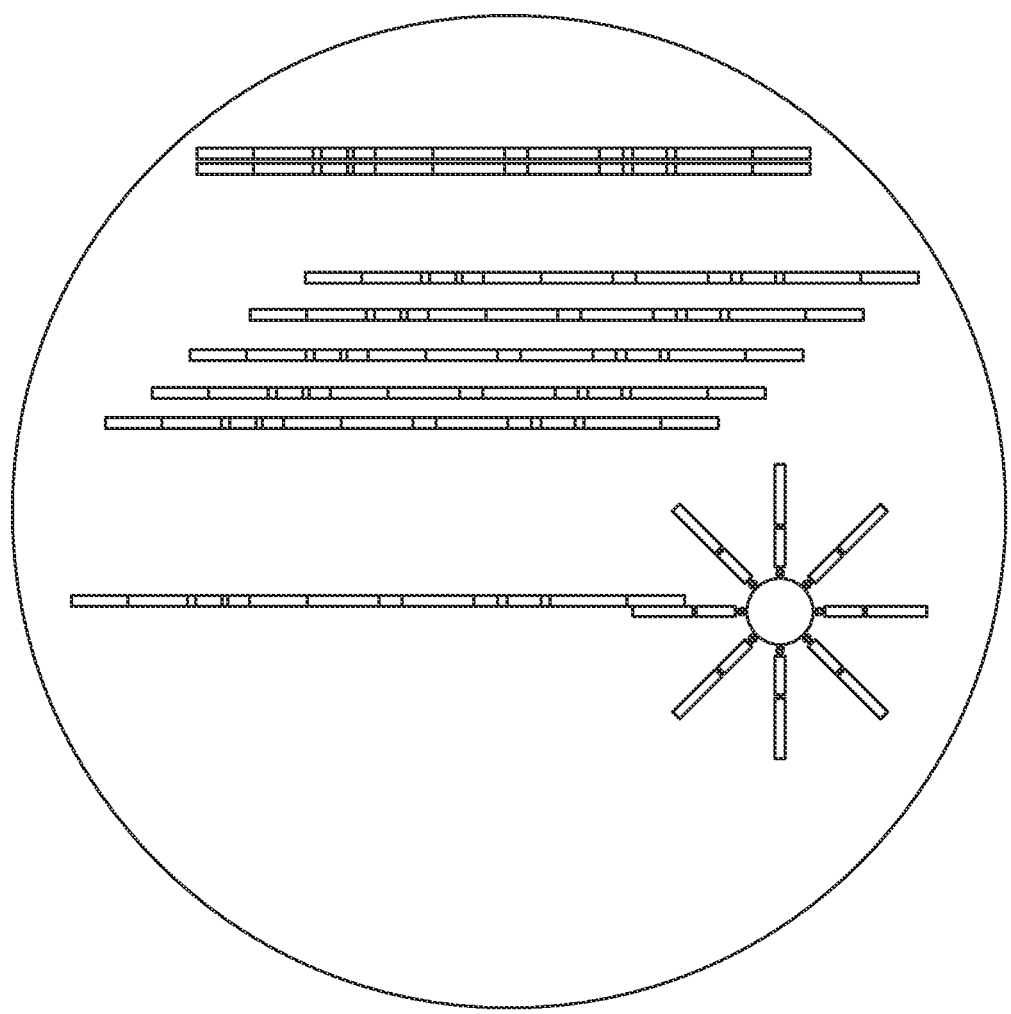
FIG. 6: A schematic showing an example asymmetric PCR step in an emulsion of the embodiments.
Figure 7:
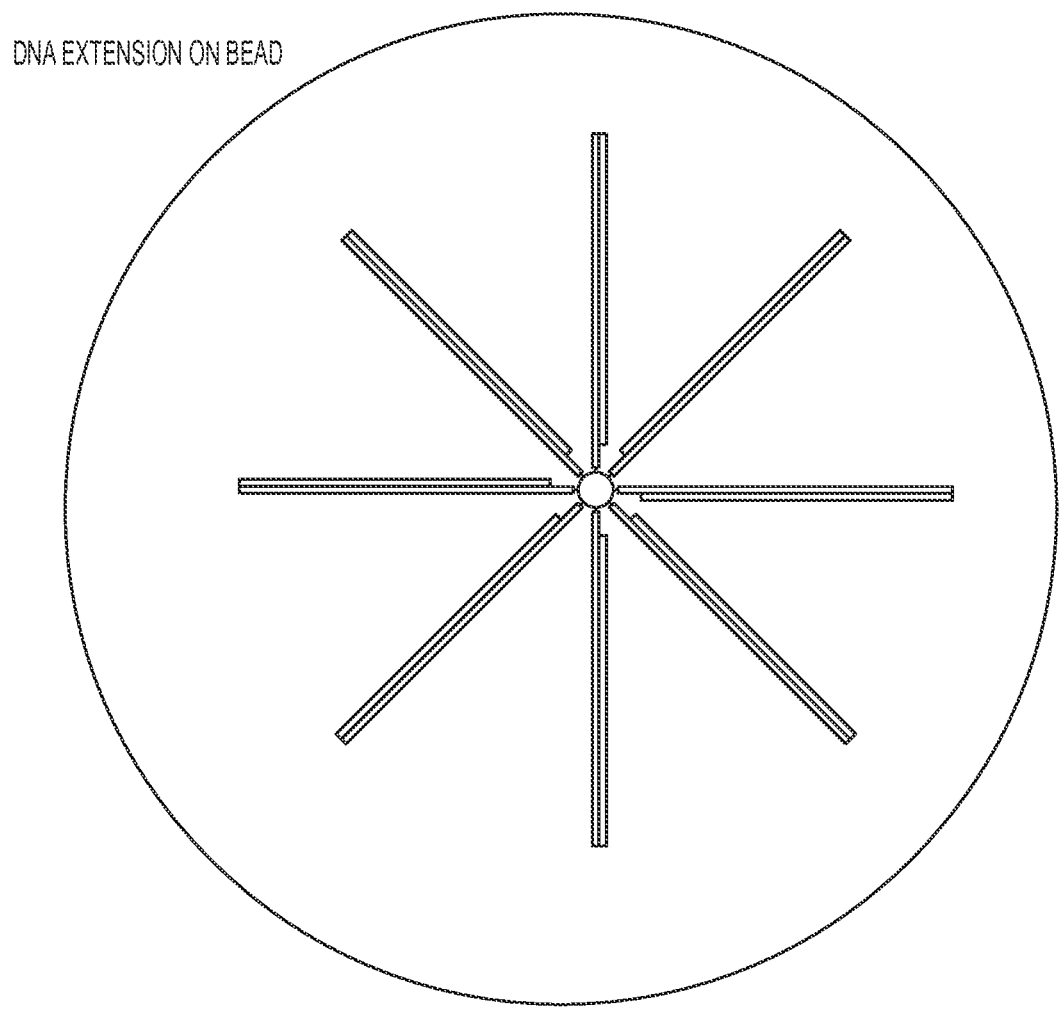
FIG. 7: A schematic showing an emulsion of the embodiments that comprises nucleic acid library linked to a bead.

An example process for linking a solution phase DNA library with the coated beads is shown in FIGS. 5-6. First, the coated beads and the DNA molecules are mixed and placed into a water-in-oil emulsion. Importantly, the formulation is mixed such that the majority of microcapsules (or droplets) of the emulsion include only one bead and one molecule from dsDNA library (of course a large number of droplets will include only a bead, only a DNA molecule or neither). Also, included in the emulsion system are DNA polymerase, free nucleotides, and an excess of free primer molecules, depicted in FIG. 5D as "$2^{nd}$ F Primer". The collection of microcapsules is then subjected to thermocycling to mediate PCR, i.e., emulsion PCR (ePCR), as shown in FIG. 6. Through multiple rounds of PCR the DNA molecules attached to the beads are first extended by the library template sequences and then a second strand is formed. The resulting population (an individual of which is represented in FIG. 7), is composed of beads that are each attached to a plurality of identical library DNA molecules. Thus, each bead carries with it multiple copies of a different member of the library.

Figure 8:
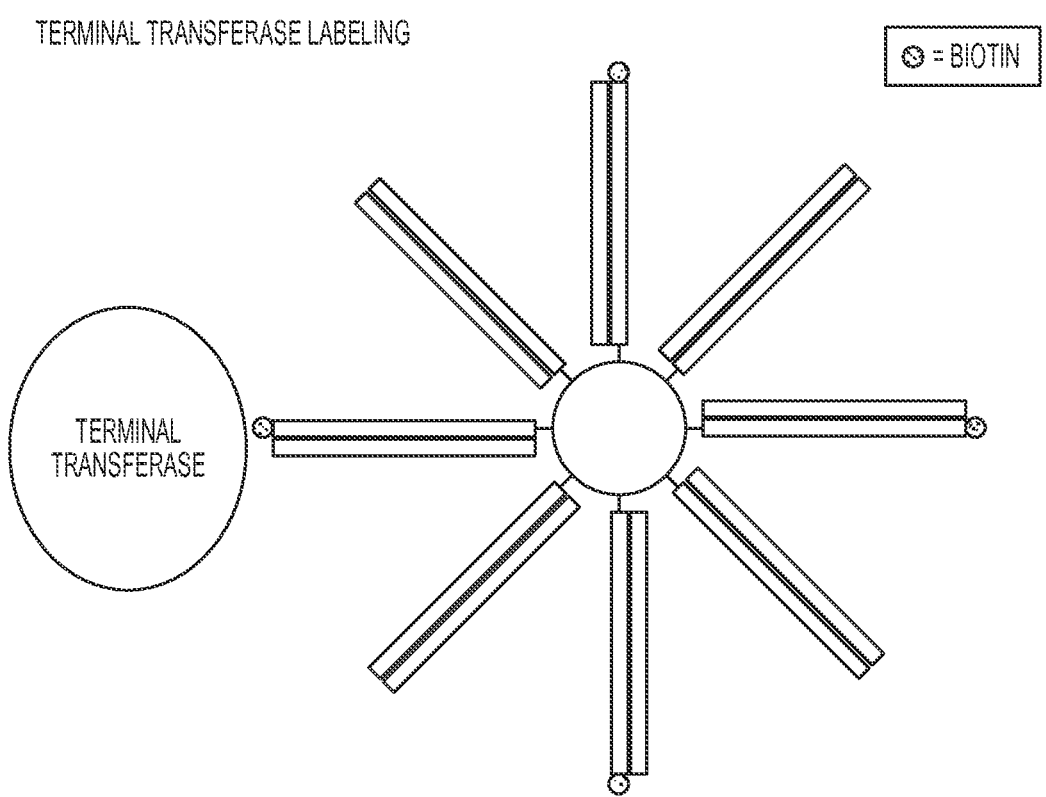
FIG. 8: A schematic showing an example terminal transferase step in accordance with the embodiments.
Figure 9:
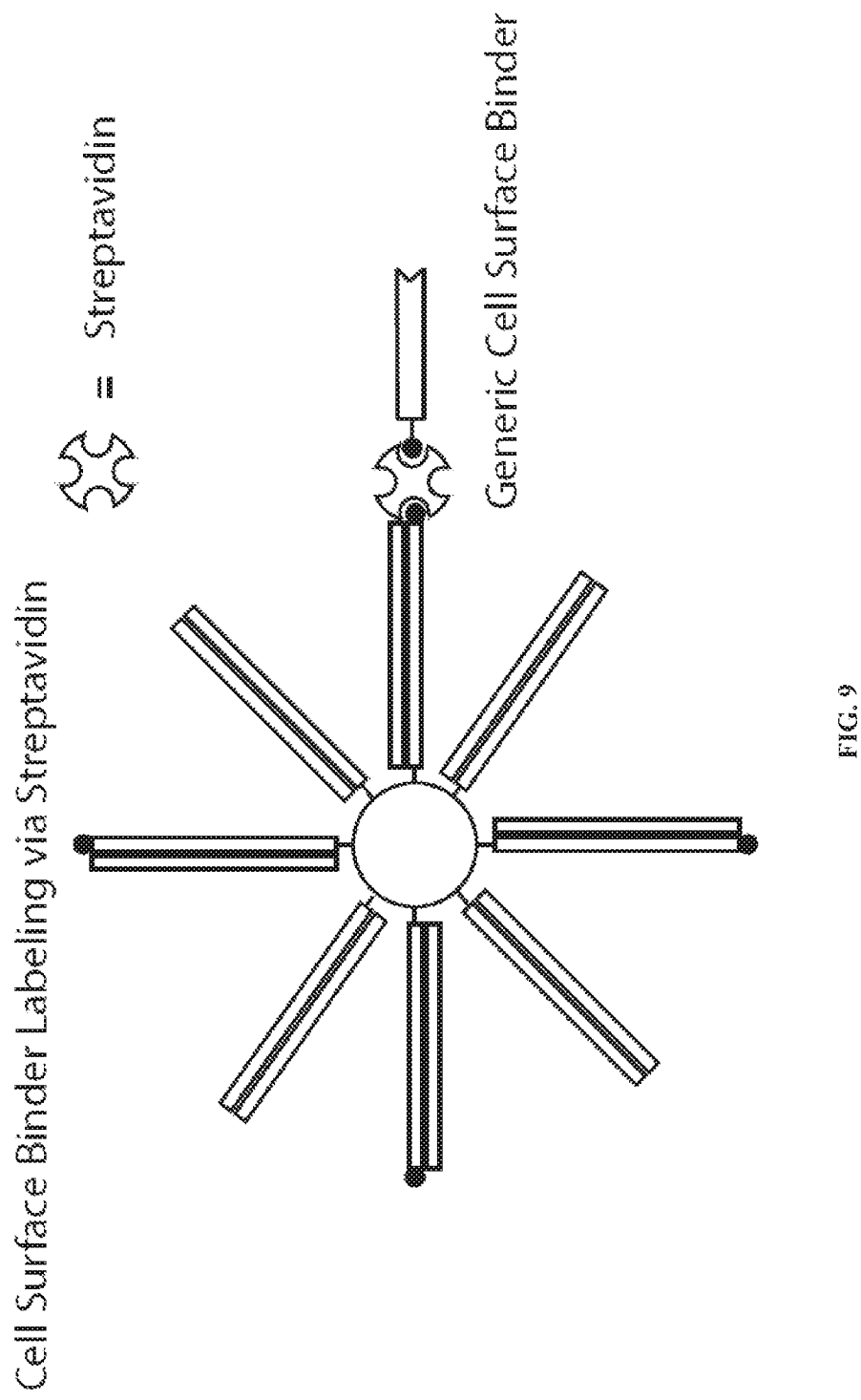
FIG. 9: A schematic showing the binding of a cell surface binding moiety to an on-bead library of the embodiments.

After linking the beads and the library, the bead-library can be removed from the emulsion. For instance, the emulsion can be broken by adding an organic solvent or a nonionic detergent, followed by mechanical disruption and gradient separation (e.g., vortexing and centrifugation). In some cases, the bead-library is also further purified (e.g., to remove excess primers and free DNA molecules, etc.). For example, the library could be purified by binding the beads to a column (e.g., a magnetic column) or by size exclusion chromatography. In some cases, the bead-library can also be further modified at this step. For example, a binding moiety can be linked to the bead library as shown in FIGS. 8-9. In this case, an affinity label, such as biotin, can be added to the DNA molecules coating the beads by using a terminal transferase (see, e.g., FIG. 8). In other aspects, the affinity label can be included in the primers used for ePCR and thereby directly incorporated in the DNA molecules upon their synthesis. Once the bead-library includes an affinity label the beads can then be linked to a binding moiety (indicated as "Generic Cell Surface Binder" in FIG. 9). An example of such linkage is shown in FIG. 9, where biotin and streptavidin are used to link the bead-library to the cell-binding moiety. Of course, a skilled worker will recognize that the beads themselves can be linked to a binding moiety and that, in this case, there would be no need for the further steps shown in FIGS. 8-9 to link the bead-library to a cell-binding moiety.

The bead-library (including the binding moiety) is next formulated into a second emulsion. Again, the emulsion is formulated to maximize the number of microcapsules that will comprise only a single member of the bead-library (see, FIG. 10) and, as such, many microcapsules will not include any bead. Also included in the aqueous portion of the emulsion are reagents for the expression of the library. In this case, such reagents include a mixture of enzymes and factors that together are competent for in vitro transcription and translation of the library. Many commercial systems are available that include these factors either separately or preformed into a complete transcription-translation system. In general, a prokaryotic (e.g., phage-based) transcription system, such as those based on the T7 or SP6 polymerase enzymes, is used. For translation, either a prokaryotic or eukaryotic system (e.g., a nuclease-treated rabbit reticulocyte lysate or HeLa cell lysate system) can be employed. Following expression, the resulting emulsion includes individual microcapsules that comprise the expression polypeptide bound to the bead, which, in turn, is bound to nucleic acid molecules encoding the expressed polypeptide (see, e.g., FIG. 11, FIG. 1B, FIG. 2B, and FIG. 3B). Thus, each bead has a plurality of identical DNA molecules and a plurality of identical polypeptide molecules expressed from those same DNA molecules. In some cases, due to random variation in the DNA amplification process, a certain low level of variation in both DNA and polypeptide sequences may exist on a given bead.

Figure 12:
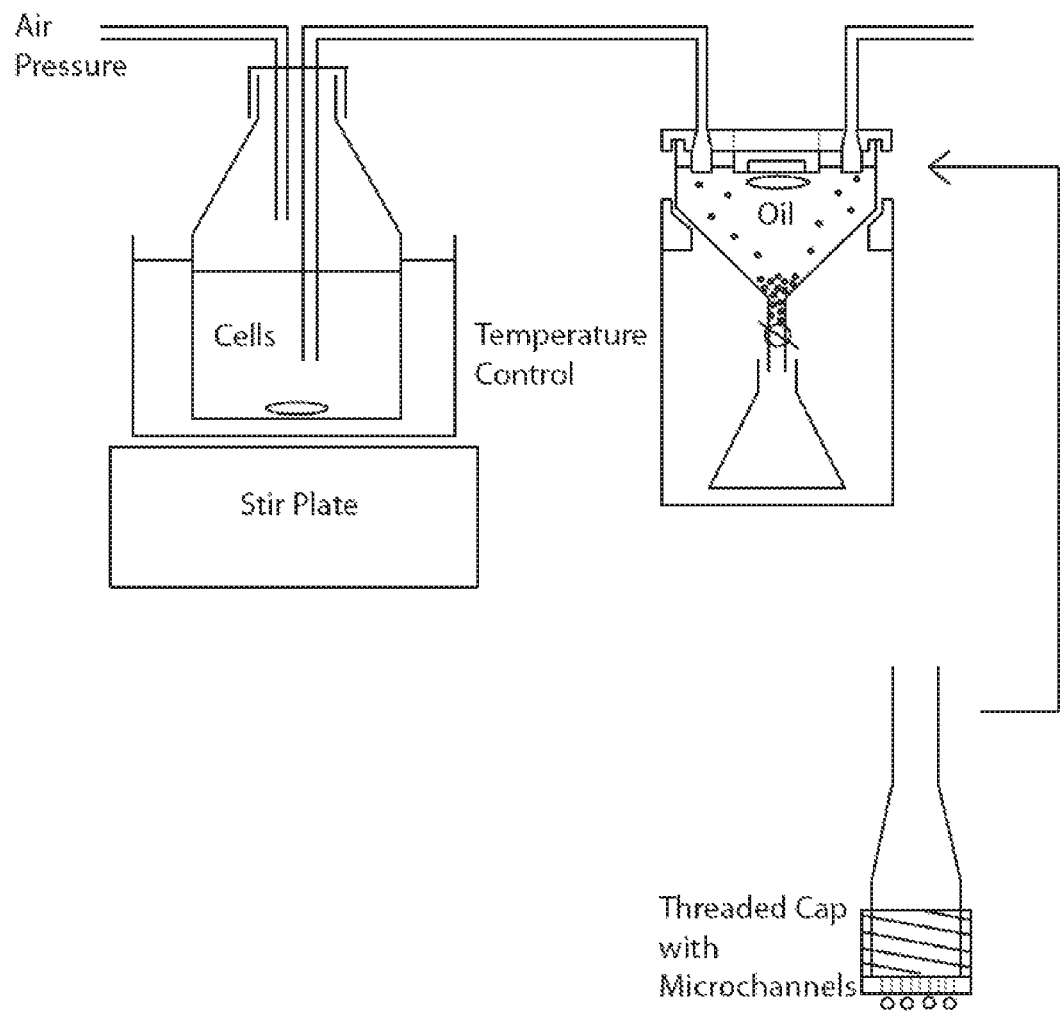
FIG. 12: A schematic showing an example system for generating a test cell emulsion of the embodiments.

To mediate screening of the expressed polypeptides, the bead library is formulated into a further emulsion that also comprises test cells and a dissociation agent that releases the polypeptide molecules from the bead. An example of an apparatus for use in formulating such a cell emulsion is shown in FIG. 12. In general, living cells are dispersed and separated in aqueous media, which is then mixed with the oil phase to form the emulsion. Again, the emulsion can be formulated such that the maximum possible number of microcapsules include an optimal number of cells (e.g. one, ten, 50, 500 or 5,000). In some cases, the cells can be maintained in, or even allowed to propagate in, the emulsion system. Moreover, in some cases, the cell emulsion can include additional elements in the aqueous phase, such as reporter molecules that mediate downstream screening (e.g., fluorescent dyes). Alternatively, microcapsules comprising the beads/nucleic acid-polypeptide complexes can be fused with microcapsules comprising test cells (see, e.g., FIG. 13).

In some cases the polypeptide expression procedure may be performed two or more times in sequence, each time with fresh transcription-translation reagents, so that the number of polypeptide molecules carried on each bead can be increased as desired.

In some cases, the number of library beads in a single microcapsule can be increased (e.g., to 5, 10, or greater) to reduce the number of microcapsules that have to be screened to identify cells that exhibit a biological response. In this case, repeated assays or sequence redundancy with-in the library will still allow identification of the polypeptide sequence that is active despite the presence of multiple coding regions associated with each "hit." For repeated assays, the DNA recovered from the hits may be reformulated as a library for each successive screen.

Figure 14:
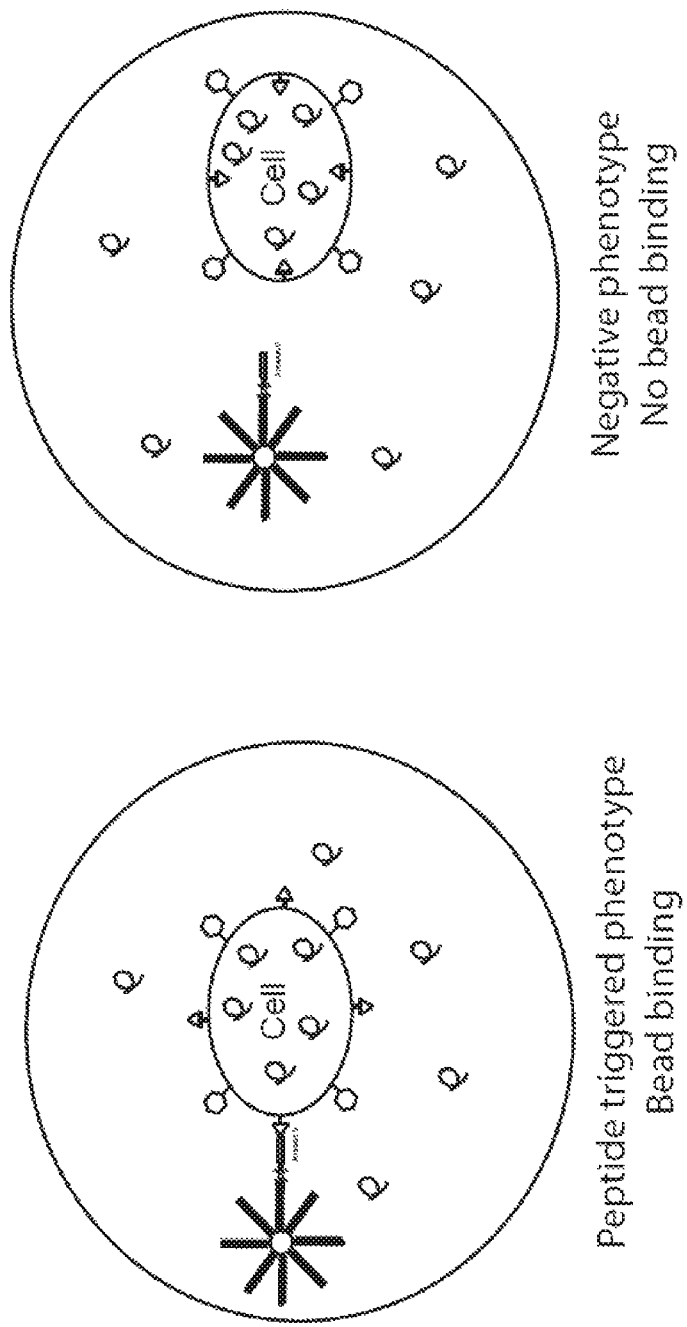
FIG. 14: A schematic showing an example of cell tagging in accordance with the embodiments. In this example, the cell surface binding moiety is Annexin V and the cell phenotype that is being screened is the induction of apoptosis.

Upon introduction of the beads of the library into microcapsules with test cells, microcapsules can be directly screened to determine whether the polypeptide comprised in any given microcapsule has a desired biological activity. An example, of such a microcapsule is shown graphically in FIG. 14. In this case, microcapsules can be sorted (e.g., by FACS) without breaking of the emulsion. If a standard FACS apparatus is used, a double emulsion can be formed by putting the existing emulsion into an aqueous continuous layer. This results in an aqueous solution for purposes of the FACS, a method that is designed for aqueous systems. For example, in some cases, biological activity can be determined by using cells that express a reporter gene (such as a fluorescent protein) in response to a biological activity. In this case, microcapsules demonstrating expression are selected by FACS. The microcapsules showing a biological response can then be isolated and the library nucleic acids sequenced to determine the structure (sequence) of biologically active polypeptide.

Figure 15:
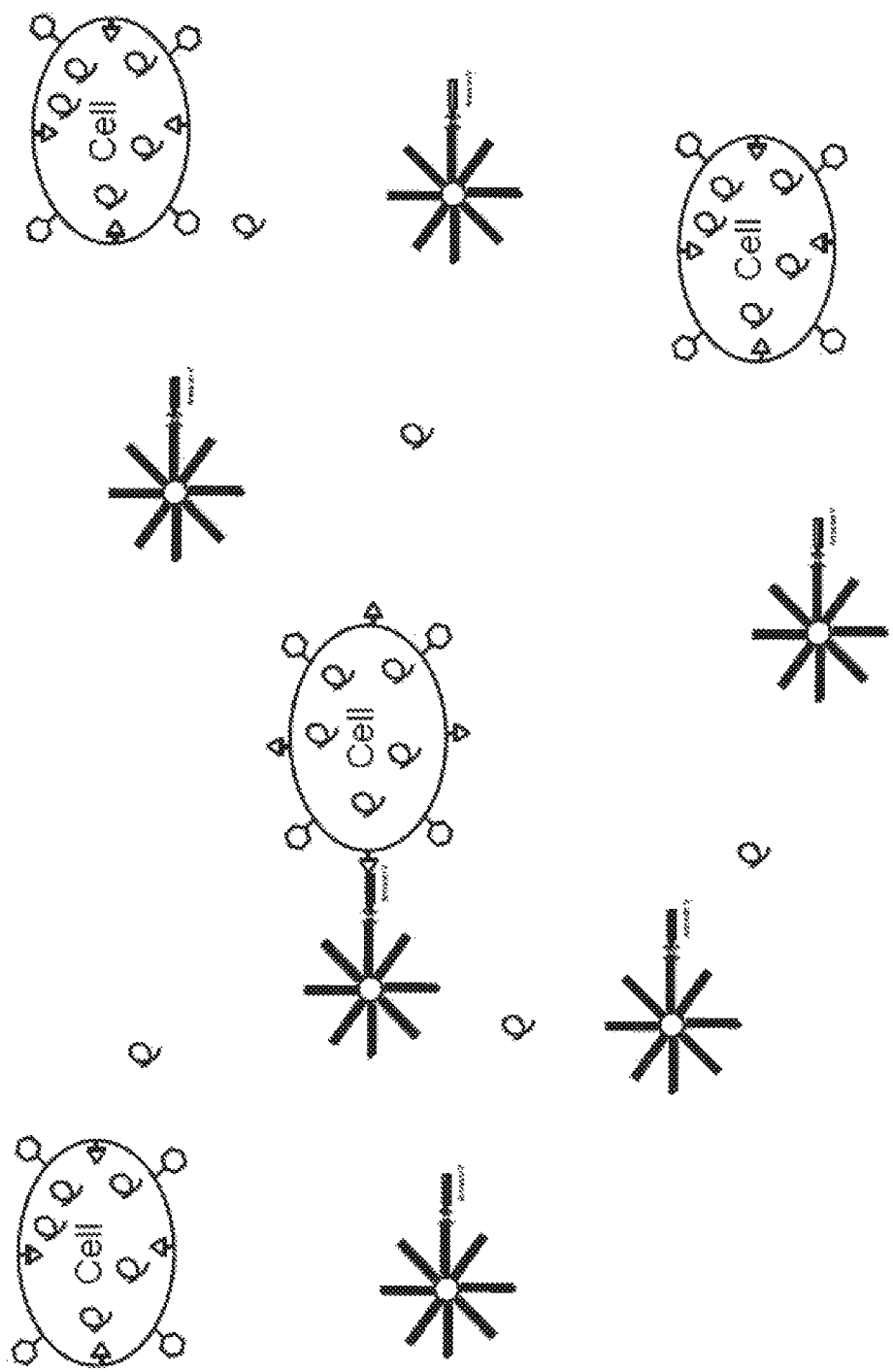
FIG. 15: A schematic showing an example of breaking an emulsion after cell tagging in accordance with the embodiments. In this example, the cell surface binding moiety is Annexin V.

In some cases, the emulsion can be broken before screening for a biological activity. In this case, by virtue of the binding moiety, the bead-library remains tethered to the test cells (see, e.g., FIG. 15). Thus, the test cells (including the bead library) can be assessed for a biological response to expressed polypeptides. For example, if the response is a change in the molecules displayed on the surface of the cell, an antibody that binds to a desired molecule (e.g., polypeptide) can be used to determine a biological response. Alternatively, the DNA molecules can be dissociated from the beads and thus only the DNA molecules would remain bound to the test cells via the binding moiety, but not the bead. Regardless of the methods used to screen or select cells that show a biological response, once the cells are identified they can separated and the tethered nucleic acid molecules sequenced to determine the coding sequence for the biologically active polypeptide.

Figure 16:
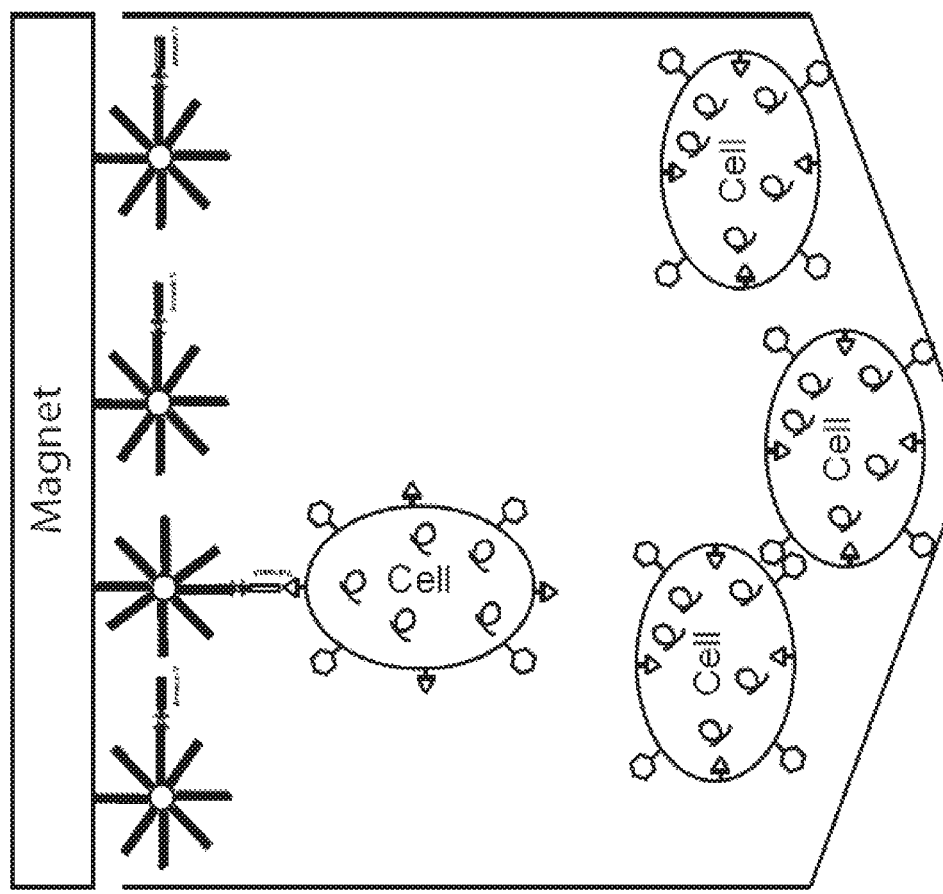
FIG. 16: A schematic showing an example magnetic bead capture after cell tagging in accordance with the embodiments. In this example, the cell surface binding moiety is Annexin V.
Figure 17:
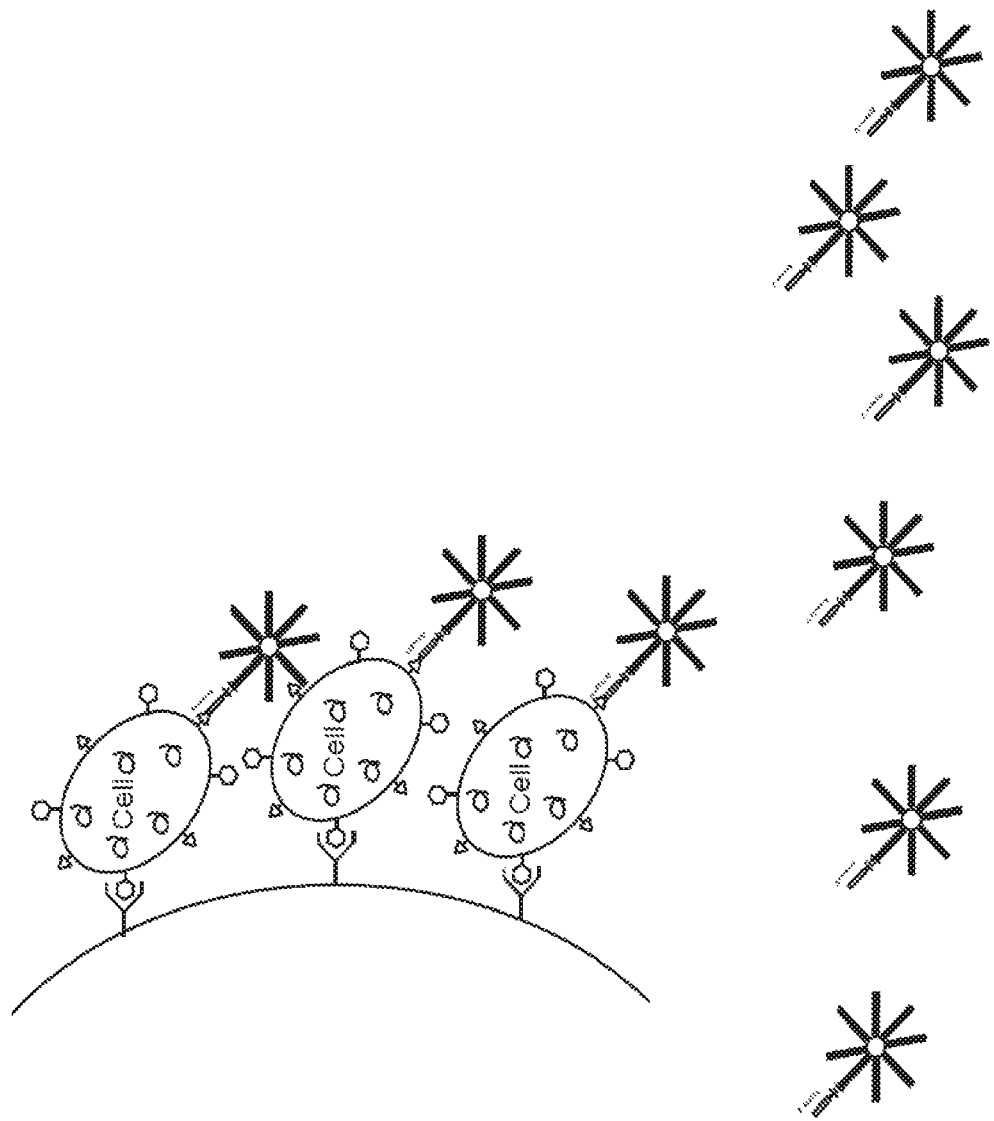
FIG. 17: A schematic showing an example of cell capture on a column in accordance with the embodiments. In this example, the cell surface binding moiety is Annexin V.

An example of a method of screening test cells for a response to a polypeptide is depicted in FIGS. 16-17. In this example, the binding moiety that is linked to bead library is also used to assess the biological response (see, FIG. 16). That is, the bead library will only bind to cells that exhibit a response to the expressed polypeptide. An example of such a binding moiety is Annexin V, which will only bind to cells that enter apoptosis in response to the polypeptide. It will, however, be recognized that virtually any cell-binding moiety could be used in a similar manner to interrogate a wide range of biological responses in the test cells. Thus, in the screening microcapsules, only cells that exhibit a biological response will be tethered to the beads. Accordingly, cells having a biological response can be purified away from other cells by isolating the beads, such as by using a magnetic isolation method (see, e.g., FIG. 16). Once the cells that do not exhibit a response are removed, the cells (and tethered beads) can be isolated from the untethered beads by a variety of methods. For example, as shown in FIG. 17, an affinity column can be used that binds to cells (e.g., using a generic cell-binding moiety). It will of course be recognized that the steps of removing cells that do not exhibit a biological response and removing beads that are not tethered to cells can be performed in any order. Alternatively, the DNA can be dissociated from the beads, such that only the DNA molecules remain tethered to the test cells. In either case, the isolated beads (including the library nucleic acids and tether cells) are sequenced to determine the sequences of biologically active polypeptides.

In a further example, the screening method detailed supra can be used to identify polypeptides that induce cell death (either via necrosis or apoptosis). For instance, the binding moiety can bind to an intracellular component from the test cells. Such a binding moiety can be an antibody against a common, robust intracellular protein such as a housekeeping protein, a RNA polymerase subunit, sigma 70 family proteins, GAPDH or Actin or an antibody that binds to an intracellular structure (e.g., chromatin or mitochondrial structures). Alternatively, a foreign protein can be expressed transgenically in the cells, and the foreign protein can have specific epitopes that are amenable to recovery via a binding moiety (e.g., Maltose Binding Protein with a His-tag that can be bound by a metal-charged chelating group). Importantly, the binding moiety should not interact with components present in the library expression system (which may be a translation competent cell lysate). To avoid this, in some aspects, the expression system can be derived from a different organism (e.g., an organism from a different Kingdom) than the test cells. For example, if test cell is a bacterium the expression system can be a rabbit reticulocyte lysate or a wheat germ extract. Likewise, in some aspects, highly specific binding moieties can be employed, such as an antibody that exhibit little or no cross-reactivity even relative to target proteins from related species. This system provides an assay for cell lysis useful in screening for antibiotics or peptides that cause cell death (e.g., in cancer cells). The only time the DNA coated bead would bind the protein is when the cell in the emulsion is lysed and spills out its contents (see for example FIG. 2E). The nucleic acids identified as "hits" can be purified in the same manner outlined above, such as by, using an affinity column with a secondary antibody to a different epitope on the same intracellular target as the first antibody and then magnetic collection of the hits. These last two steps can be performed in either sequence, magnetic collection then affinity purification or affinity purification followed by magnetic collection.

Hence, a system of the embodiments offers many significant advantages relative to other potential screening systems. For example, because the library is generated in situ it can have a nearly limitless size and diversity of sequence. Importantly, the candidate polypeptides remain associated with their coding sequences, first by virtue of the beads and then the emulsion system (or other method of compartmentalization), so active molecules can be identified by sequencing of the coding sequence. However, unlike a phage display system, candidate polypeptides need not be covalently tethered to superfluous sequences (e.g., phage protein sequences). This allows the candidate polypeptides to fold independently of such sequences, which may provide molecules with a higher activity than a sterically hindered fusion protein. Additionally, any biological activity of identified polypeptides is truly indicative of an activity of the candidate polypeptide rather than non-bioactive binding, or an artifact of a phage fusion protein. Furthermore, this system makes it possible to test biological activity in live cells; in other words the system is not limited to binding assays as is generally the case for phage-display and other display approaches. Thus, the methods of the embodiments not only provide for screening of a vast diversity of sequences, but also provide a screen that can be far more effective than any previous technique in providing biologically active candidate molecules. Further aspects applicable to the methods of the embodiments are discussed in detail below.

I. DNA Library

Certain aspects of the embodiments concern a library of DNA sequence, at least a subset of which encode a translation open reading frame (ORF) and can thereby serve as a template protein synthesis. Thus, as used herein the term "library" is used in reference to a collection of molecules (e.g., nucleic acid or polypeptide molecules) or cells wherein a plurality of individual species comprising the library are distinct from other cells or molecules of the same library in at least one detectable characteristic. Examples of libraries of molecules include libraries of nucleic acids, peptides, polypeptides, proteins, fusion proteins, polynucleotides, or oligonucleotides.

In certain embodiments a DNA library of the embodiments comprises (i) an ORF, including a translation initiation site (e.g., an ATG codon in a favorable Kozak consensus or a Shine-Dalgarno ribosome binding site (RBS)) and termination codon; (ii) a polymerase promoter sequence (e.g., a T7 polymerase binding site); (iii) a polymerase terminator sequence; and (iv) primer sequences that flank the ORF. In some preferred aspects the nucleic acid molecules further comprise an affinity tag, such a biotin tag. For example, a library may be composed of molecules comprising, in order from 5' to 3', a biotin tag—a forward primer binding sequence—a polymerase promoter sequence—an ORF—a polymerase terminator sequence—a reverse primer binding sequence (e.g., 5'-biotin-primer-T7 promoter-ORF-T7 terminator-primer-3'). In further aspects the ORF sequence can be further flanked by additional or alternative primer binding sequences such as, in order from 5' to 3', a biotin tag—a forward primer binding sequence—a polymerase promoter sequence—an additional forward primer binding sequence—an ORF—an additional reverse primer binding sequence—a polymerase terminator sequence—a reverse primer binding sequence.

A DNA library of the embodiments may be composed of naturally occurring or artificially synthesized molecules. For example, in certain aspects, a library is composed of nucleic acid sequences that represent genomic DNA sequences or cDNA sequences (or portions thereof) from an organism, such as a human. In further aspects, a library may comprise an essentially random ORF coding sequence. ORF coding sequence in a library can also be chimeric sequences including segments of sequence from two different organisms or segments of sequence derived from cDNA and segments that are randomized. Likewise, DNA microarrays can be used as a template for construction of a DNA library of the embodiments. In some aspects, a DNA library represents the entire (or nearly the entire) proteome of an organism, such as a human. In some preferred aspects a library is composed of artificially synthesized nucleic acid sequences derived from cDNA with one or more site specific randomized variants. In some aspects a library is composed of artificially synthesized single chain antibody fragments (e.g., a fusion protein of the variable regions of the heavy (VH) and light chains (VL) of an immunoglobulin), where specific sequence segments in the variable region are randomized.

Furthermore, in certain aspects, library sequences can include segments of sequence that encode polypeptides having a known function, such as a cell-binding domain or cell penetrating peptide (CPP) in the ORF sequence along with sequence derived from cDNA, genomic DNA, or randomized sequence (i.e., to generate an ORF encoding a fusion protein). Thus, in certain aspects, DNA molecules of the embodiments comprise an ORF that comprises a CPP coding sequence along with a segment of library sequence (such as randomized sequence), 5' of the CPP coding sequence 3' of the CPP coding sequence or both. As used herein the terms "cell penetrating peptide" and "membrane translocation domain" are used interchangeably and refer to segments of polypeptide sequence that allow a polypeptide to cross the cell membrane (e.g., the plasma membrane in the case of a eukaryotic cell). Examples of CPP segments include, but are not limited to, segments derived from HIV Tat, herpes virus VP22, the *Drosophila* Antennapedia homeobox gene product, or protegrin I. In still further aspects, library sequences can include segments of sequence that encode polypeptides that facilitate intracellular localization of the library polypeptides, such as sequences that promote escape from endosomes, provide nuclear localization or mitochondrial localization.

Methods for generating and amplifying a nucleic acid library of the embodiments are well known in the art. In certain embodiments, it may be desired to employ one or more techniques for the manipulation, isolation or amplification of nucleic acids. Such techniques may include, for example, the preparation of vectors as well as methods for cloning selected nucleic acid segments from a cell (e.g., cloning cDNA sequences or fragments thereof).

Nucleic acids used as a template for amplification may be isolated from cells, tissues or other samples according to standard methodologies (Sambrook et al., 1989) or amplified from synthetic DNA, where the synthetic DNA is derived from linear strands, plasmids, or from a DNA microarray. In certain embodiments, nucleic acids may be amplified from whole cells or tissue homogenates or biological fluid samples (with or without substantial purification of the template nucleic acid). The nucleic acid may be genomic DNA or fractionated or whole cell RNA. Where RNA is used, it may be desired to first convert the RNA to a complementary DNA by use of a reverse transcriptase, as outlined below.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids comprising one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to generate cDNA sequence (or cDNA fragments). Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids, which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 discloses a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

As detailed herein, in certain aspects, a library of DNA molecules of the embodiment can be bound to a support such as bead. For example, in the case a library of DNA molecules that comprise a biotin moiety, the library can be bound to streptavidin-coated beads. In still further aspects, a bead for use in the embodiments can comprise one or more binding moieties (e.g., a polypeptide and a cell-binding moiety) and/or a moiety that aids in purification of the bead (e.g., a bead may comprise a fluorescent marker or the beads can be magnetic).

As used herein a "cell-binding moiety" refers to a molecule that binds to a component of a test cell such as a cell surface protein or an intracellular protein. Such moieties can bind to cells generally or bind to specific cell populations (e.g., stem cells, cells of certain tissue type or cells that are apoptotic). For example, the cell-binding moiety can be an antibody (e.g., a monoclonal antibody), an aptamer, a lectin, a proteoglycan, or a receptor or ligand polypeptide. In some specific aspects, the cell-binding moiety is Annexin V or an anti-CD34 antibody. In another example the cell-binding moiety is an anti-CD-63 antibody, which will bind to activated basophils. In this case, the assay could be used to screen polypeptides for induction of allergic reactions. Further examples of cell-binding moieties include anti-CD44+, anti-CD49fhi or CD133hi antibodies for binding to estrogen-negative breast cancer cells. In a further example, the cell-binding moiety can be a protein expressed by the cell as a transgene. For instance, an anti-microbial polypeptide that causes cell lysis of E. coli can be detected by (i) expressing maltose binding protein with a histidine-tag in the E. coli test cells, and (ii) using a nickel-charged chelating group as a binding moiety to capture the maltose binding protein that is released from E. coli cells that are lysed.

II. Emulsion PCR

For emulsion PCR, an emulsion PCR reaction is created by vigorously shaking or stirring a "water in oil" mix to generate a multitude of miniature aqueous compartments. The DNA library is mixed in a limiting dilution to generate compartments containing, on average, just one DNA molecule and bead (at the optimal dilution many compartments may be empty). To facilitate amplification efficiency, both an upstream (low concentration, matches primer sequence on bead) and downstream PCR primers (high concentration) are included in the reaction mix. Depending on the size of the aqueous compartments generated during the emulsification step, up to $3 \times 10^9$ individual PCR reactions per µl can be conducted simultaneously in the same tube. Essentially each little compartment in the emulsion forms a micro PCR reactor. The average size of a compartment in an emulsion ranges from sub-micron in diameter to over 100 microns, depending on the emulsification conditions.

Emulsion Systems

A wide variety of microencapsulation procedures are available (see Benita, 1996) and may be used to create microcapsules used in accordance with the present embodiments. More than 200 microencapsulation methods have been identified in the literature (Finch, 1993). These include membrane enveloped aqueous vesicles such as lipid vesicles (liposomes; New, 1990) and non-ionic surfactant vesicles (van Hal et al., 1996). These are closed-membranous capsules of single or multiple bilayers of non-covalently assembled molecules, with each bilayer separated from its neighbor by an aqueous compartment. In the case of liposomes the membrane is composed of lipid molecules; these are usually phospholipids but sterols such as cholesterol may also be incorporated into the membranes (New, 1990). A variety of enzyme-catalyzed biochemical reactions, including RNA and DNA polymerization and RNA translation, can be performed within liposomes (Chakrabarti et al., 1994; Oberholzer et al., 1995a; Oberholzer et al., 1995b; Walde et al., 1994; Wick & Luisi, 1996). Enzyme-catalyzed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi and Steinmann-Hofmann, 1987; Mao & Walde, 1991; Mao et al., 1992; Perez-Gilabert et al., 1992; Walde et al., 1994; Walde et al., 1993; Walde et al., 1988) such as the AOT-isooctane-water system (Menger & Yamada, 1979).

With a membrane-enveloped vesicle system much of the aqueous phase is outside the vesicles and is therefore non-compartmentalized. In some aspects, this continuous, aqueous phase is removed or the biological systems in it inhibited or destroyed (for example, by digestion of nucleic acids with DNase or RNase) in order that the reactions are limited to the microcapsules (Luisi and Steinmann-Hofmann, 1987).

Microcapsule droplets can also be generated by interfacial polymerization and interfacial complexation (Whateley, 1996). Microcapsules of this sort can have rigid, nonpermeable membranes, or semipermeable membranes. Semi-permeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992). Non-membranous microencapsulation systems based on phase partitioning of an aqueous environment in a colloidal system, such as an emulsion, may also be used.

Preferably, the microcapsule droplets of the present embodiments are formed from emulsions. The primary water-in-oil microcapsule droplets are formed from heterogeneous systems of two immiscible liquid phases with one of the phases dispersed in the other as droplets of microscopic or colloidal size (Becher, 1957; Sherman, 1968; Lissant, 1974; Lissant, 1984). Emulsions may be produced from any suitable combination of immiscible liquids. Preferably the emulsion of the present embodiments has water that contains the biochemical components, as the phase present in the form of finely divided microcapsules (the disperse, internal or discontinuous phase) and a hydrophobic, immiscible liquid (an "oil", such as mineral oil) as the matrix in which these microcapsules are suspended (the nondisperse, continuous or external phase). Such emulsions are termed "water-in-oil" (w/o). This has the advantage that the entire aqueous phase containing the biochemical components is compartmentalized in discreet microcapsules (the internal phase). The hydrophobic oil phase, generally contains none of the biochemical components and hence is inert.

The primary emulsion may be stabilized by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Particularly suitable oils include light white mineral oil and non-ionic surfactants (Schick, 1966) such as sorbitan monooleate (Span™ 80; ICI), octyl phenol ethoxylate (Triton™ X-100) and polyoxyethylenesorbitan monooleate (Tween™ 80; ICI). Other emulsifying agents that may be used include, silicone-based emulsifier such as Bis-PEG/PPG-14/14 Dimethicone, Cyclopentasiloxane (ABIL EM 90)

The use of anionic surfactants may also be beneficial. Suitable surfactants include sodium cholate and sodium taurocholate. Particularly preferred is sodium deoxycholate, at a concentration, such as 0.5% w/v, or less. Inclusion of such surfactants can, in some cases, increase the expression of the nucleic acids molecules and/or the activity of the encoded polypeptides. Addition of some anionic surfactants to a non-emulsified reaction system completely abolishes translation. During emulsification, however, the surfactant is transferred from the aqueous phase into the interface and activity is restored. Addition of an anionic surfactant to the mixtures to be emulsified ensures that reactions proceed only after compartmentalization.

Creation of an emulsion generally requires the application of mechanical energy to force the phases to mix together. There are a variety of ways of doing this, which utilize a variety of mechanical devices, including stirrers (such as magnetic stir-bars, propeller and turbine stirrers, vortexers, paddle devices and whisks), homogenizes (including rotor-stator homogenizes, high-pressure valve homogenizes and jet homogenizes), colloid mills, ultrasound and "membrane emulsification" devices (Becher, 1957; Dickinson, 1994).

Water-in-oil microcapsule emulsions of the present embodiments are generally stable with little if any exchange of contents (e.g., nucleic acids) between the microcapsules. Additionally, biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

III. Emulsion Expression

There are many possible available protocols for emulsion expression. For example, protocols are provided in Tawfik and Griffiths 1998; Ghadessy et al. 2001; Ghadessy and Hollinger 2004 and in U.S. Pat. Publns. 20070077572 and 20090197248, each of which is incorporated herein by reference in its entirety. In general, expression involves providing the nucleic acid molecules in the presence of factors required for expression, which can be produced recombinantly, provided by cell lysates (or extracts thereof) or a combination of the two. In the case of nucleic acids molecules composed of RNA, only translation machinery needs to be provided. However, in preferred aspects the nucleic acid molecules are DNA and the expression system includes factors for RNA synthesis and protein synthesis (i.e., transcription and translation). Reagents for such combined transcription and translation ("TnT") are commercially available and can be used in accordance with the embodiments (see e.g., the TNT® systems available from Promega, Madison Wis.).

The processes of expression must occur within each individual microcapsule provided by the present embodiments. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. In some aspects a eukaryotic translation system (such as a mammalian cell lysate) is used in the expression system. In this case, the efficiency of protein synthesis may be significantly enhanced by providing a transcription system that includes reagents to mediate capping of the RNA transcripts and/or additional of a poly-A tail to the RNAs. In still further aspects, a stretch of poly-A residues may be template on the coding DNA molecules (e.g., following the ORF coding sequence).

The effective genetic element, namely, DNA or RNA, concentration in the microcapsules may be artificially increased by various methods that will be well known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Q.beta. replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*). Increasing the effective local nucleic acid concentration enables larger microcapsules to be used effectively.

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM. In the case of reactions involving translation, it is to be noted that the ribosomes necessary for the translation to occur are themselves approximately 20 nm in diameter. Hence, the preferred lower limit for microcapsules is a diameter of approximately 0.1 µm (100 nm).

The size of emulsion microcapsules may be varied simply by tailoring the emulsion conditions used to form the emulsion according to requirements of the selection system. The larger the microcapsule size, the larger is the volume that will be required to encapsulate a given library, since the ultimately limiting factor will be the size of the microcapsules and thus the number of microcapsules possible per unit volume.

The size of the microcapsules is selected not only having regard to the requirements of the transcription/translation system, but also those of the downstream selection/screening system employed and the size of the test cells.

IV. Cell Emulsions

A wide range of cells can be compartmentalized in microcapsules, such as the aqueous microcapsules of a water-in-oil emulsion (see, e.g., Ghadessy, 2001). In certain aspects, cells for an emulsion will be cells that have been adapted for growth in suspension. For example, cells that overexpress MDM2 can be used, as can suspension adapted HeLa S3 cells a variety of leukemia cell lines (e.g., Jurkat), and certain strains of 293T cells. In some other aspects, cells are not adapted for suspension growth, but are suspended just prior preparation of the cell-containing emulsion. For example, cells isolated from a tissue being grown on a substrate can be disrupted by mechanical agitation and/or treatment with protease (e.g., trypsin) prior to emulsification; in some cases such cells will grow in cluster or spheroids and exhibit desirable properties for bioactivity testing. In further cases, adherent cell lines can be grown on micro-carrier beads, such as the Cytodex™ beads (available from Sigma-Aldrich). These cell-coated beads can then be placed into emulsion.

A schematic showing a system for producing cell emulsions is provided as FIG. 12. In general emulsion formation can be carried out as detailed above and previously described in U.S. Pat. Publns. 20070077572 and 20090197248, each incorporated herein by reference. Methods for generating a single cell emulsions are also provided in Brouzes et al. (2009); Baret et al. (2010); and in U.S. Patent Publn. 20100022414, each of which is incorporated herein by reference.

Microcapsules in the cell emulsions can further comprise components that will be used to assay for biological activity of the library polypeptides. For example, such components can include fluorescent dyes, buffers, ions (e.g., $Ca^{2+}$, or $Mg^{2+}$), enzymes, antibodies, cofactors and the like. Likewise, nuclease inhibitors, protease inhibitors and/or non-specific blockers, to reduce non-specific or low affinity interactions between a binding moiety and its target, can be included. Non-specific blockers can be, for example, abundant serum proteins, such albumin (e.g., bovine serum albumen (BSA)). In further aspects, any of the foregoing components can be added to the system just prior to performing an assay to identify cells that exhibit a biological response (that is after the merger of the library and cell emulsions).

V. Emulsion Merger

In some aspects, microcapsules can be fused or split. For example, aqueous microcapsules can be merged (and split) using microfluidics systems (Song et al., 2003). Microcapsule fusion allows the mixing of reagents, such as library components and test cells. For example, in one set of embodiments, systems and methods are provided that are able to cause two or more microcapsules (e.g., arising from discontinuous streams of fluid) to fuse or coalesce into one microcapsule in cases where the two or more microcapsules ordinarily are unable to fuse or coalesce, for example, due to composition, surface tension, microcapsule size, the presence or absence of surfactants, etc. In certain microfluidic systems, the surface tension of the microcapsules, relative to the size of the microcapsules, may also prevent fusion or coalescence of the microcapsules from occurring in some cases.

In one embodiment, two fluidic microcapsules may be given opposite electric charges (i.e., positive and negative charges, not necessarily of the same magnitude), which may increase the electrical interaction of the two microcapsules such that fusion or coalescence of the microcapsules can occur due to their opposite electric charges, e.g., using the techniques described herein. For instance, an electric field may be applied to the microcapsules, the microcapsules may be passed through a capacitor, a chemical reaction may cause the microcapsules to become charged, etc. The microcapsules, in some cases, may not be able to fuse even if a surfactant is applied to lower the surface tension of the microcapsules. However, if the fluidic microcapsules are electrically charged with opposite charges (which can be, but are not necessarily of, the same magnitude), the microcapsules may be able to fuse or coalesce.

In another embodiment, the fluidic microcapsules may not necessarily be given opposite electric charges (and, in some cases, may not be given any electric charge), and are fused through the use of dipoles induced in the fluidic microcapsules that cause the fluidic microcapsules to coalesce. An electric field for use in such methods can be an AC field or a DC field and may be created, for instance, using electrodes. The induced dipoles in each of the fluidic microcapsules may cause the fluidic microcapsules to become electrically attracted towards each other due to their local opposite charges, thus causing the microcapsules to fuse.

In various embodiments, the two or more microcapsules allowed to coalesce are not necessarily required to meet "head-on." Any angle of contact, so long as at least some fusion of the microcapsules initially occurs, is sufficient. Other examples of fusing or coalescing fluidic microcapsules are described in International (PCT) Patent Application No. PCT/US2004/010903, incorporated herein by reference.

VI. Assay for Bioactive Polypeptides

In a further aspect, the embodiments provide systems and methods for screening or sorting test cells and/or microcapsules in a liquid (e.g., of a microcapsule), a well, a tube or a gel and assessing biological activity of polypeptides. For example, a characteristic of a cell or microcapsule may be sensed and/or determined in some fashion (e.g., as further described below), then the microcapsule or cell may be selected or directed towards a particular region of the device, for example, for sorting or screening purposes. In further aspects, cells or microcapsules can be purified based on a detectable bioactivity of a polypeptide. For example, in the case an activity that changes the composition at the cell surface, a moiety, such as an antibody that detects this change can be used to purify the cell. In the case of a biological activity that induces apoptosis, for instance, binding of Annexin to the cells can be used purify the cells.

As discussed above, in some aspects, the microcapsules (or merged microcapsules) are broken before an assay to detect or select cells that exhibit a biological response is performed. Accordingly, reagents for use in selection or screening can be added to an aqueous phase, just before, during or just after braking of the emulsion. For example such components can include fluorescent dyes, buffers, ions (e.g., $Ca^{2+}$, or $Mg^{2+}$), enzymes, antibodies, cofactors and the like. Likewise, non-specific blockers, such as serum proteins (e.g., BSA) can be added. In further aspects, nuclease inhibitors and/or excess amounts of irrelevant nucleic acid can be added to aid in preserving the nucleic acid molecules that constitute the library.

In some cases, a specific blocker can be added, such as an excess amount of a soluble component recognized by the binding moiety associated with the nucleic acid library. In the case of a binding moiety that is an antibody, a peptide containing the antibody-recognized epitope can be added. Such blockers will block the binding moieties on the majority of unbound antibodies (i.e., from droplets that were negative for a biological activity) and thereby prevent them from binding to positive cells or cell components after the emulsion is broken (when the aqueous phases become mixed). For instance, the DNA coated beads will, in many cases, have multiple copies of the binding moiety and multiple binding events per bead will greatly increase the strength of the binding. However, once the aqueous phases are mixed, beads from all of the microcapsules could potentially bind to cells that exhibit a biological response. The use of such specific blockers at this step reduces these interactions and thereby decreases the number of false positives that could be identified. This step can also be performed with a large dilution and/or at a low temperature to slow the binding kinetics and reduce binding of false positives.

In some aspects, biologically active polypeptides may be detecting an enzymatic activity or a fluorescence signal. For example, in some aspects, a test cell may be a transgenic cell that comprises an enzyme, such that a desirable biological activity results in a detectable enzymatic catalysis. For instance, a test cell may express luciferase such that if cell lysis releases the enzyme (in the presence of a substrate) a detectable luminesce signal is produced indicating cell lysis. In another example, a test cell may have a promoter responsive to a desired biological activity that controls expression of a reporter gene (such as GFP). In this case activation of the promoter would result in detectable expression of the gene indicative of the biological activity of the polypeptide.

One example of a biological response that can be screened or selected in accordance with the methods of the embodiments is cell death or lysis. For example, lysis of bacterial cells that have been incubated with the products of the in vitro transcription/translation reactions in water-in-oil emulsions can be detected using antibodies to intracellular targets such as sigma 70 family proteins, housekeeping proteins or RNA polymerase subunits. Alternatively, the intracellular target detected can be a protein expressed by the cell as a transgene. Similar methods can likewise be employed to measure the lysis of eukaryotic cells using antibodies specific for intracellular targets such as housekeeping proteins or RNA polymerase subunits GAPDH or actin. In either case, beads including the DNA library can be conjugated to a primary antibody. The beads can then be used for emulsion transcription/translation reactions in water-in-oil emulsion and fused with the bacterial (or eukaryotic) cells and incubated for a period of time (protease inhibitors can be added to the emulsions when necessary to protect the integrity of the target protein). The water-in-oil emulsions are then broken using previously described methods and the aqueous phase is passed over a resin coupled to the secondary binding moiety (such as an antibody that binds to a different epitope on the same target as the primary antibody). Beads that do not contain the protein of interest bound to the primary antibody are washed from the resin and collected. Beads containing the protein of interest bound to the primary antibody are eluted from the column using standard methods and as detailed below and the isolated nucleic acids (e.g., isolated from the eluted beads) are sequenced.

In some aspects, detecting a biological response can involve detecting a characteristic such as fluorescence of a cell or microcapsule may be determined, and an electric field may be applied or removed from the cell or microcapsule to direct it to a particular channel. In some cases, high sorting speeds may be achievable using certain systems and methods of the invention. Thus, in one embodiment of the invention, fluorescence activated cell sorting (FACS) screening or other automated flow cytometric techniques may be used for the efficient isolation of test cells or microcapsules (and associated nucleic acid molecules) that exhibit a response to a candidate polypeptide. Instruments for carrying out flow cytometry are known to those of skill in the art and are commercially available. Examples of such instruments include FACS Star Plus, FACScan and FACSort instruments from Becton Dickinson (Foster City, Calif.) Epics C from Coulter Epics Division (Hialeah, Fla.) and MOFLO™ from Cytomation (Colorado Springs, Co).

Flow cytometric techniques in general involve the separation of cells, emulsion microcapsules or other particles in a liquid sample. Typically, the purpose of flow cytometry is to analyze the separated cells or particles for one or more characteristics thereof, for example, presence of a labeled ligand or other molecule. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

Rapid quantitative analysis of cells can thus be achieved with FACS. The system permits quantitative multiparameter analysis of cellular properties at rates of several thousand cells per second. These instruments provide also the ability to differentiate among cell types, for example, in an assay to identify cell differentiation promoting molecules. Importantly, cells or particles that display a desired parameter (e.g., fluoresce) can be channeled into a separate flow stream, thereby isolating the cell and/or particle. Thus, not only is cell analysis performed by flow cytometry, but so too is sorting of cells. In U.S. Pat. No. 3,826,364, an apparatus is disclosed which physically separates particles, such as functionally different cell types. In this machine, a laser provides illumination, which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, another advantage known to those of skill in the art is that nonviable cells can be recovered using flow cytometry. Since flow cytometry is essentially a particle sorting technology, the ability of a cell to grow or propagate is not necessary. Thus, FACS can be used to screen for polypeptides that induce cell death, such as apoptosis. Techniques for the recovery of nucleic acids from such non-viable cells are well known in the art and may include, for example, use of template-dependent amplification techniques including PCR.

While various embodiments contemplate the use of microfluidic methods for screening a biological activity it is also contemplated that cells may be screened while compartmentalized or immobilized, such as in gel, a well or on a slide. For example, the test cells can comprise an array with each compartment or isolated zone comprising test cells and (on average) one member of a library for testing. Methods for assessing activity may be employed as outlined above (e.g., enzymatic activity, fluorescence, luminescence, etc.) and positive hits can be selected from each of the isolated cell populations. As with flow cytometry methods, methods using plates or arrays of cell populations are highly amenable to automation, as would be preferable for high-throughput screening. Furthermore, methods involving the use of immobilized cells can also employ antibodies or other binding moieties to detect a biological activity in cells (e.g., as in a modified ELISA assay).

Once a cell and associated nucleic acid have been isolated the nucleic acid can be sequenced to provide the structure of the polypeptide having the desired biological activity. For instance, primer binding sequences comprised in the nucleic acid molecules can be used to rapidly amplify and/or sequence the molecules. In some cases, a coding sequence with an identified biological activity is used as the basis for a new library in a screening method such as that detailed here. For example, the identified coding sequence can be partially randomized and subjected to one or more additional screening steps to identify coding sequences that have enhanced biological activity or to determine which portions of a coding sequence are required for a biological activity.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screen for Biologically Active Polypeptide in Eukaryotic Cells

General DNA Bead Tagging of Cells
Equipment:
thermocycler apparatus (PCR™ machine)
Nanodrop spectrophotometer
Reagents:
DNA oligonucleotides For DNA library construction beads are labeled with the library coding sequences that are amplified from DNA oligonucleotide molecules. Oligonucleotide molecules can be chemically synthesized on site or a obtained from a commercial supplier, such as IDT (see the World Wide Web at (idtdna.com/Home/Home.aspx). In general, degenerate DNA oligonucleotides encoding a peptide library with a forward and reverse universal primer sequence on each end and an ATG at the start site of translation will be used. The basic forward primer includes a 5' biotin, a spacer, a T7 promoter, a spacer, a Shine-Dalgarno ribosome binding site (RBS), a spacer, and a universal primer sequence. A basic reverse primer includes a T7 termination sequence and a universal primer. See, e.g., FIG. 5.

In some aspects a cell penetrating peptide (CPP) can be included in the library coding sequences. In this case the forward primers include in the following order: a 5' biotin, a spacer, a T7 promoter, a spacer, a Shine-Dalgarno RBS, a spacer, a CPP encoding region starting with an ATG site, a forward universal primer.

A basic PCR™ procedure is as follows:
1. Bring up the DNA in water or TE to a standard stock concentration. Make two primer sets. The first is for intracellular targets and will include the CPP primers. The other is for extracellular targets and uses only the basic primers. For intracellular targets, mix basic and CPP forward primers in equimolar concentrations and aliquot.
2. Set up PCR reaction using the DNA library oligos as the DNA template and the pooled forward primers and the basic reverse primer for the primers. Run a standard PCR protocol 3. Purify the PCR™ products using standard methods and quantify the DNA using the spectrophotometer.
Bead-Based Emulsion PCR
Protocols for bead-based emulsion PCR can be found for example in Williams et al. 2006, incorporated herein by reference. A diagram of the process and the resulting product are shown in FIGS. 5-7.
Equipment:
ULTRA-TURRAX® Tube Drive Workstation—IKA
ST-20 Tubes—IKA
Overhead Stirrer
Microcentrifuge
PCR machine
Vacuum centrifuge
Reagents:
Streptavidin coated, silica based, magnetic beads (see, e.g., the world wide web at: products.invitrogen.com/ivgn/product/65601).
DNA reverse primer plus linker with duel 5' biotins—IDT
DNA forward primer with 5' nuclease resistant phosphorothioate bonds (alternatively, Locked Nucleic Acids, LNAs, can be used instead of phosphorothioate bonds).
ABIL EM 90, a surfactant (Degussa)
BSA (Sigma-Aldrich)
dNTPs (Roche)
Diethyl Ether (water saturated—Riedel-de-Haen)
Ethyl acetate (water saturated—Riedel-de-Haen)
Mineral oil (Sigma-Aldrich)
Pfu Turbo DNA polymerase (2.5 U/uL; Stratagene)
Span™ 80, a surfactant (Fluka)
Triton® X-100, a surfactant (Fisher Scientific)
Tween™ 80, a surfactant (Sigma-Aldrich)
Procedure:
1. Prepare the oil-surfactant mixture by mixing in a 50-mL tube at 25 degrees C.:

| Span 80 | 2.25 mL |
| Tween 80 | 200 μL |
| Triton X-100 | 25 μL |
| Mineral oil | to 50 Ml |

For a more stable oil-surfactant mixture, 2% ABIL EM 90 and 0.05% Triton X-100 can be used.
2. Prepare standard PCR™ reaction mix with the following modifications:
Add ~$10^9$ beads (see above).
Add ~$10^9$ DNA molecules from the library
Add forward and reverse primers
3. Add the PCR reaction mix dropwise to the stirring oil-surfactant mixture to create the emulsion. Transfer to PCR tubes and a PCR machine and run a standard protocol.
4. Pool the PCR products and centrifuge. Dispose of the upper oil phase.
5. Extract beads from emulsion with diethyl ether and magnet.
6. Wash beads with a mix of ethanol and hybe buffer.
7. Use terminal transferase to end label the DNA on the beads with biotin.
8. Prepare streptavidin/cell surface binder conjugate by mixing equimolar concentrations of streptavidin and biotin labeled, relevant cell surface binder for the cell line being used (e.g., a biotin tagged monoclonal antibody against CD34 for stem cells) in a streptavidin/biotin compatible binding buffer.
9. Add the relevant cell surface binder/streptavidin conjugates for binding to the beads by resuspending the beads in streptavidin/biotin compatible buffer and mixing with streptavidin/cell surface binder conjugate at <1:1000 (bead to cell surface binder) molar ratio. See, e.g., FIGS. 8-9.

10. Purify beads magnetically, wash and dry.

Emulsion Expression

Figure 10:
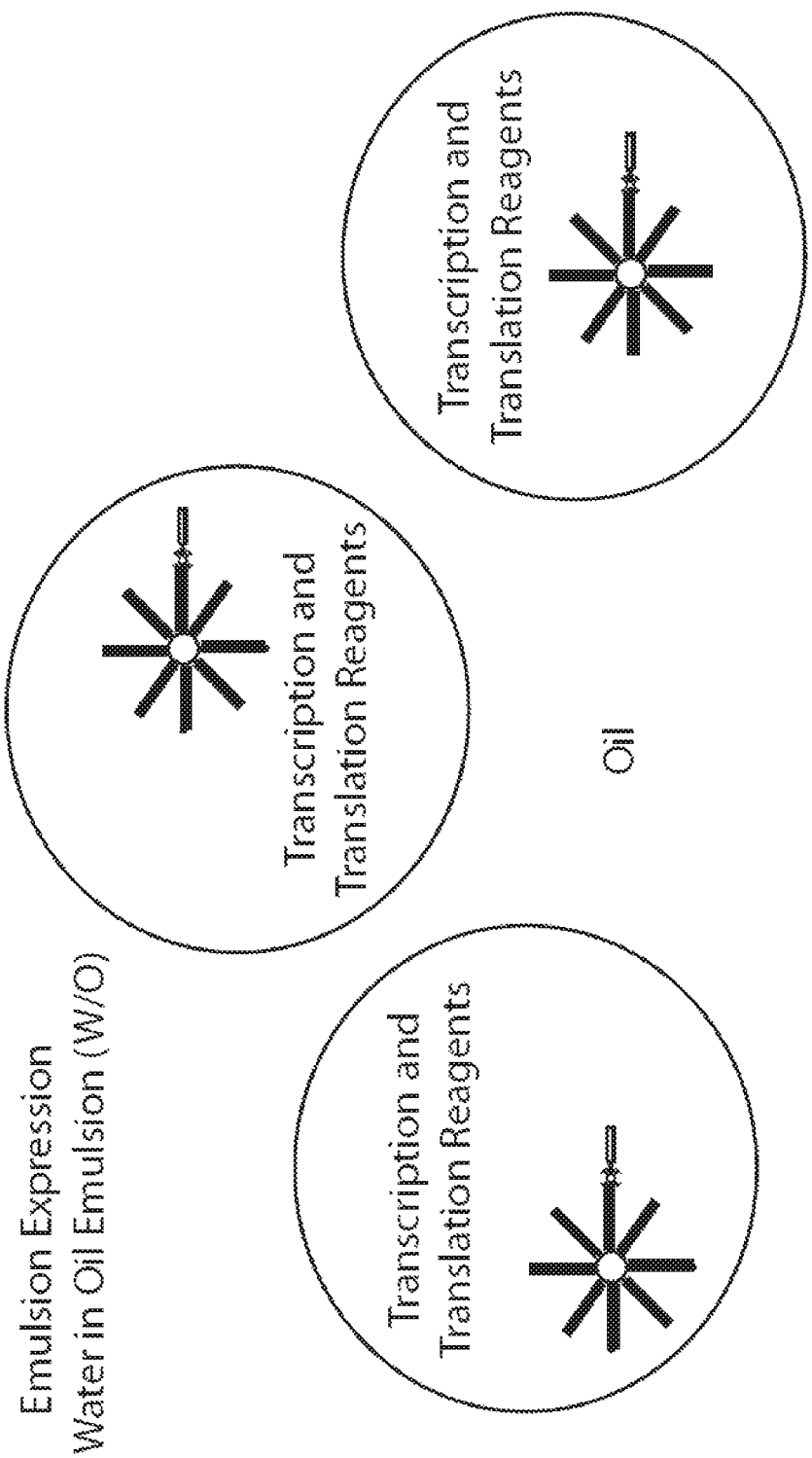
FIG. 10: A schematic showing an example library expression step in an emulsion of the embodiments.
Figure 11:
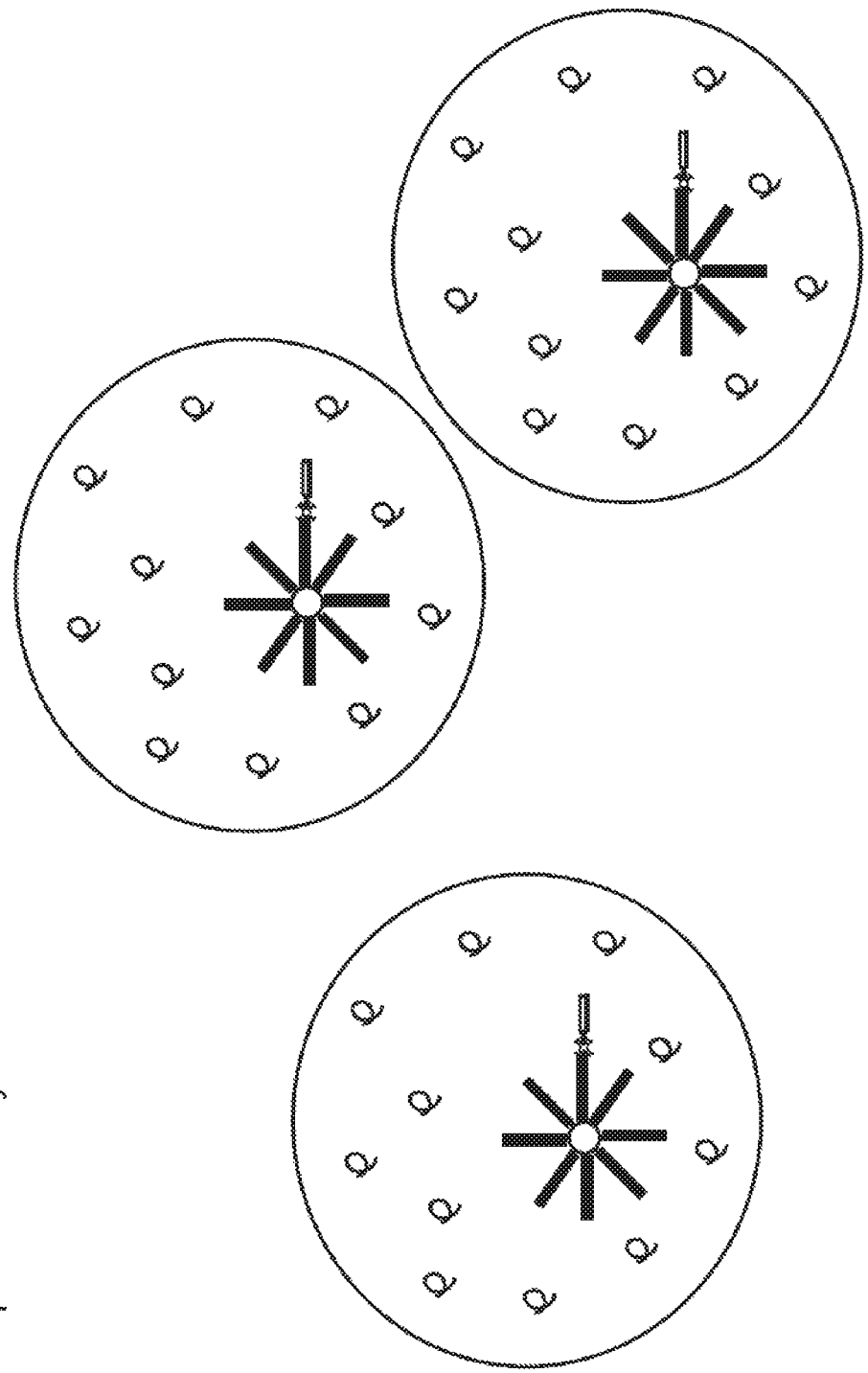
FIG. 11: A schematic showing an example of an expressed peptide library in an emulsion of the embodiments.

A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004) DOI: 10.1093/protein/gzho25, each of which is incorporated herein by reference. An example schematic is shown in FIGS. 10-11.

Equipment:
Ultra-Turrax Tube Drive Workstation—IKA
St-20 tubes—IKA
Reagents:

| Product | Vendor |
|---|---|
| E. coli S30 Extract | Promega |
| T7 RNA Polymerase | Promega |
| Sodium Deoxycholate | Sigma |
| Span 80 | Sigma |
| Mineral Oil | Sigma |
| Tween 80 | Pierce |

Procedure:
1. Supplement the Promega E. coli S30 extract kit with 10 nM G3 carrier DNA, 100 U T7 RNA polymerase ($10^4$ units), 40 U RNase inhibitor, sodium deoxycholate (0.5% w/v for emulsified reactions) with beads at 4° C.
2. Create oil phase by dissolving 4.5% (v/v) Span 80 in mineral oil followed by 0.5% Tween 80.
3. Add supplemented Expression Kit reagents with beads dropwise to stirring oil-surfactant mix in a CryoTube vial (5×10 μL over ~2 min). Stir for 1 minute after addition of reaction mixture to the oil.
4. Incubate at 37° C. for 2 hours.

Cell Emulsification
Equipment:
Cell Emulsifier
Cell culture system
Sterile hood
Autoclave
Incubator
Reagents:
Cells from a MDM2 overexpressing cell line capable of growing in suspension
Growth Medium
Procedure:
1. In sterile hood, add cells to Cell Emulsifier system at a concentration that results in an average of one cell per emulsion droplet.
2. Encapsulate cells in appropriate growth medium for the chosen cell line with or without serum supplements and with $CaCl_2$ supplement to ~2.5 mM in ~100 μm water droplets in oil.
3. Incubate for 1-4 hours to allow equilibration of cells to new environment. An example system for cell emulsification is shown in FIG. 12.

Figure 13:
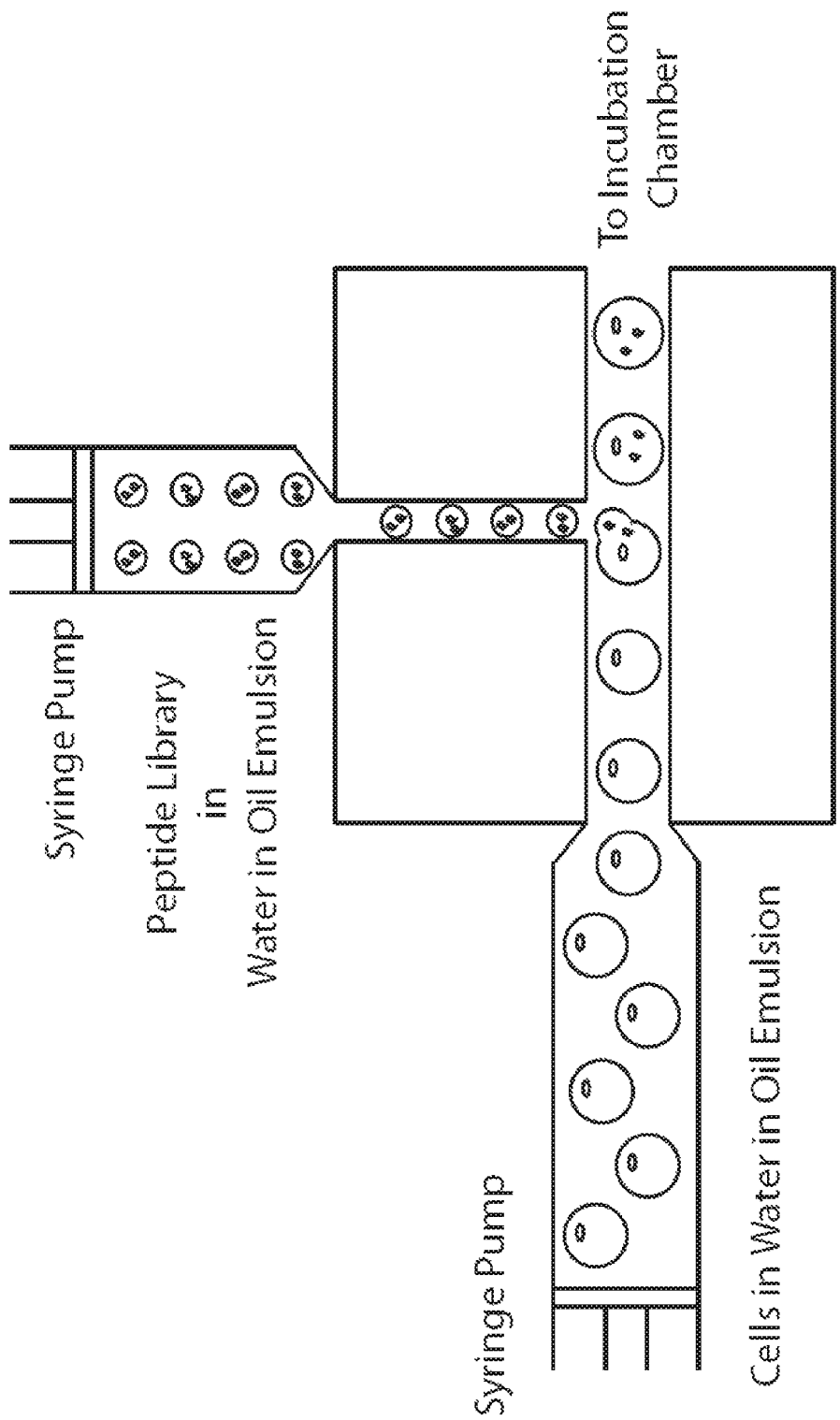
FIG. 13: A schematic showing an example system for fusing microcapsules from emulsions of the embodiments.

Peptide Delivery to Cells
Equipment:
Custom microfluidic chips for merge of separate water-in-oil emulsion streams
Syringe pumps for delivering emulsion streams to merge chip
Aliquot collection system for collecting the merge emulsion stream
Incubator
Procedure:
1. Load large syringe with cell emulsion
2. Load small syringe with peptide emulsion
3. Pump both emulsion streams through the merge module on the microfluidics chip.
4. Collect the merged emulsion stream in 1-3 hour aliquots and incubate. During incubation the cell surface binder tagged DNA coated beads will bind to the cells. An example system for merging emulsions is shown in FIG. 13.

Phenotype Labeling and Hit Identification
Equipment:
Magnetic bead collection apparatus
Flow cytometer
PCR machine
Reagents:
Phenotype specific labeling reagents (e.g. Fluorescently labeled Annexin V or live/dead stains)
Standard PCR reagents
Procedure:
1. Break emulsion by adding ether.
2. Collect beads and attached cells with the magnetic bead collection apparatus.
3. Incubate cells with labeling reagents. Labeling reagents can be a fluorescent label attached to a phenotype specific binding protein such as Annexin V. Alternatively, they could be live/dead staining dyes for differentiating living vs. dead cells.
4. Collect hits using a cell sorting device that will segregate the labeled hits from the unlabeled negatives.
5. PCR amplify the DNA from the beads attached to the collected hits using the appropriate primers to prepare the DNA for sequencing.
6. Sequence the amplified DNA or send amplified DNA to sequencing service company. The sequencing results will identify the peptides that induced the desired phenotype.

Example 2

Screen for Apoptosis Inducing Polypeptides

General DNA Bead Tagging of Cells
Equipment:
thermocycler apparatus (PCR™ machine)
Nanodrop spectrophotometer
Reagents:
DNA oligonucleotides
For DNA library construction beads are labeled with the library coding sequences that are amplifies from DNA oligonucleotide molecules. Oligonucleotide molecules can be chemically synthesized on site or a obtained from a commercial supplier, such as IDT (see the World Wide Web at (idtdna.com/Home/Home.aspx). In general, degenerate DNA oligonucleotides encoding a peptide library with a forward and reverse universal primer sequence on each end and an ATG at the start site of translation will be used. The basic forward primer includes a 5' biotin, a spacer, a T7 promoter, a spacer, a Shine-Dalgarno ribosome binding site (RBS), a spacer, and a universal primer sequence. A basic reverse primer includes a T7 termination sequence and a universal primer. See, e.g., FIG. 5.

In some aspects a cell penetrating peptide (CPP) can be included in the library coding sequences. In this case the forward primers include in the following order: a 5' biotin, a spacer, a T7 promoter, a spacer, a Shine-Dalgarno RBS, a spacer, a CPP encoding region starting with an ATG site, a forward universal primer.

A basic PCR™ procedure is as follows:

1. Bring up the DNA in water or TE to a standard stock concentration. Make two primer sets. The first is for intracellular targets and will include the CPP primers. The other is for extracellular targets and uses only the basic primers. For intracellular targets, mix basic and CPP forward primers in equimolar concentrations and aliquot.

2. Set up PCR reaction using the DNA library oligos as the DNA template and the pooled forward primers and the basic reverse primer for the primers. Run a standard PCR protocol 3. Purify the PCR™ products using standard methods and quantify the DNA using the spectrophotometer.

Bead-Based Emulsion PCR

Protocols for bead-based emulsion PCR can be found for example in Williams et al. 2006, incorporated herein by reference. A diagram of the process and the resulting product are shown in FIGS. 5-7.

Equipment:
ULTRA-TURRAX® Tube Drive Workstation—IKA
ST-20 Tubes—IKA
Overhead Stirrer
Microcentrifuge
PCR machine
Vacuum centrifuge Reagents:
Streptavidin coated, silica based, magnetic beads (see, e.g., the world wide web at: products.invitrogen.com/ivgn/product/65601).
DNA reverse primer plus linker with duel 5' biotins—IDT
DNA forward primer with 5' nuclease resistant phosphorothioate bonds (alternatively, Locked Nucleic Acids, LNAs, can be used instead of phosphorothioate bonds).
ABIL EM 90, a surfactant (Degussa)
BSA (Sigma-Aldrich)
dNTPs (Roche)
Diethyl Ether (water saturated—Riedel-de-Haen)
Ethyl acetate (water saturated—Riedel-de-Haen)
Mineral oil (Sigma-Aldrich)
Pfu Turbo DNA polymerase (2.5 U/uL; Stratagene)
Span™ 80, a surfactant (Fluka)
Triton® X-100, a surfactant (Fisher Scientific)
Tween™ 80, a surfactant (Sigma-Aldrich)

Procedure:
1. Prepare the oil-surfactant mixture by mixing in a 50-mL tube at 25 degrees C.:

| Span 80 | 2.25 mL |
| Tween 80 | 200 uL |
| Triton X-100 | 25 uL |
| Mineral oil | to 50 mL |

For a more stable oil-surfactant mixture, 2% ABIL EM 90 and 0.05% Triton X-100 can be used.

2. Prepare standard PCR™ reaction mix with the following modifications:
Add ~$10^9$ beads (see above).
Add ~$10^9$ DNA molecules from the library
Adjust the primer concentrations for asymmetric PCR and have the forward primer at 8× the concentration of the reverse primer.

3. Add the PCR reaction mix dropwise to the stirring oil-surfactant mixture to create the emulsion. Transfer to PCR tubes and a PCR machine and run a standard protocol.

4. Pool the PCR products and centrifuge. Dispose of the upper oil phase.

5. Extract beads from emulsion with diethyl ether and magnet.

6. Wash beads with a mix of ethanol and hybe buffer.

7. Use terminal transferase to end label the DNA on the beads with biotin.

8. Prepare streptavidin/cell surface binder conjugate by mixing equimolar concentrations of streptavidin and biotin labeled, relevant cell surface binder for the cell line being used (e.g., a biotin tagged monoclonal antibody against CD34 for stem cells) in a streptavidin/biotin compatible binding buffer.

9. Add the relevant cell surface binder/streptavidin conjugate for binding to the beads by resuspending the beads in streptavidin/biotin compatible buffer and mixing with streptavidin/cell surface binder conjugate at <1:1000 (bead to cell surface binder) molar ratio. See, e.g., FIGS. 8-9.

10. Purify beads magnetically, wash and dry.

Emulsion Expression

A wide range of protocols are available for emulsion expression, see for example Tawfik and Griffiths (1998); Ghadessy et al. (2001); or Ghadessy and Hollinger (2004), each of which is incorporated herein by reference. An example schematic is shown in FIGS. 10-11.

Equipment:
Ultra-Turrax Tube Drive Workstation—IKA
St-20 tubes—IKA

Reagents:

| Product | Vendor |
| --- | --- |
| E. coli S30 Extract | Promega |
| T7 RNA Polymerase | Promega |
| Sodium Deoxycholate | Sigma |
| Span 80 | Sigma |
| Mineral Oil | Sigma |
| Tween 80 | Pierce |

Procedure:
1. Supplement the Promega E. coli S30 extract kit with 10 nM G3 carrier DNA, 100 U T7 RNA polymerase ($10^4$ units), 40 U RNase inhibitor, sodium deoxycholate (0.5% w/v for emulsified reactions) with beads at 4° C.

2. Create oil phase by dissolving 4.5% (v/v) Span 80 in mineral oil followed by 0.5% Tween 80.

3. Add supplemented Expression Kit reagents with beads dropwise to stirring oil-surfactant mix in a CryoTube vial (5×10 µL over ~2 min). Stir for 1 minute after addition of reaction mixture to the oil.

4. Incubate at 37° C. for 2 hours.

Cell Emulsification

Equipment:
Cell Emulsifier
Cell culture system
Sterile hood
Autoclave
Incubator

Reagents:
Cells from a MDM2 overexpressing cell line capable of growing in suspension
Growth Medium Procedure:
1. In sterile hood, add cells to Cell Emulsifier system at a concentration that results in an average of one cell per emulsion droplet.

2. Encapsulate cells in appropriate growth medium for the chosen cell line with or without serum supplements and with CaCl$_2$ supplement to ~2.5 mM in ~100 µm water droplets in oil.

3. Incubate for 1-4 hours to allow equilibration of cells to new environment. An example system for cell emulsification is shown in FIG. 12.

Peptide Delivery to Cells

Equipment:
Custom microfluidic chips for merge of separate water-in-oil emulsion streams
Syringe pumps for delivering emulsion streams to merge chip
Aliquot collection system for collecting the merge emulsion stream
Incubator Procedure:
1. Load large syringe with cell emulsion
2. Load small syringe with peptide emulsion
3. Pump both emulsion streams through the merge module on the microfluidics chip.
4. Collect the merged emulsion stream in 1-3 hour aliquots and incubate. During incubation cells that have peptides that induce apoptosis will present the phosphotidylserine on the extracellular membrane and the annexin V tagged DNA coated beads will bind to the cells. An example system for merging emulsions id shown in FIG. 13.

Hit Identification

Equipment:
Magnetic bead collection apparatus
PCR machine

Reagents:
Cell-binding column
Standard PCR reagents

Procedure:
1. Break emulsion by adding ether (see, e.g., FIG. 15).
2. Collect beads with the magnetic bead collection apparatus (see, FIG. 16).
3. Run the collected beads over the cell-binding column to collect apoptotic cells and bound beads (see, FIG. 17).
4. PCR amplify the DNA from the beads attached to the apoptotic cells using the appropriate primers to prepare the DNA for sequencing.
5. Sequence the amplified DNA or send amplified DNA to sequencing service company. The sequencing results will identify the peptides that induced apoptosis.

Example 3

Screen for Antimicrobial Peptides

Library Preparation

Equipment:
Nanodrop spectrophotometer

Reagents:
A master DNA library with site-specific randomized variants of the bee venom Melittin, which is optimized for in vitro expression; obtained from DNA 2.0 (see the World Wide Web at dna20.com) and cloned into the pIVEX vector (5 Prime, Inc.).
A raw sub-library amplified from the master library with the Illustra GenomiPhi V2 DNA amplification kit (GE Healthcare)
A linearized sub-library made from the raw sub-library using the Restriction enzyme CLA1 (cut DNA)

Figure 18B:
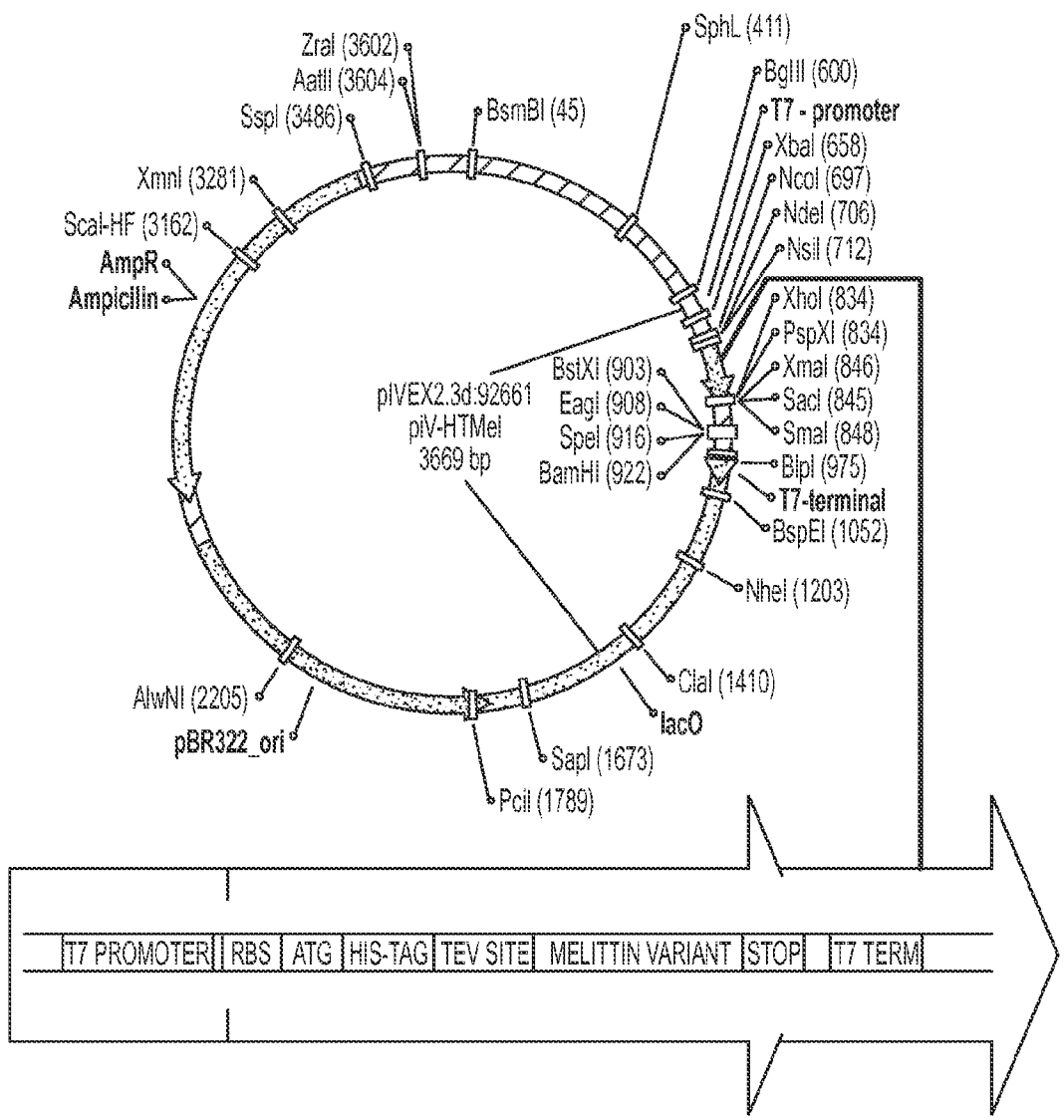

The DNA library was based on the wild-type sequence of Melittin from the honeybee (*Apis mellifera*), which is: GIGAVLKVLTTGLPALISWIKRKRQQ (SEQ ID NO: 1). To construct the library, residues number 5, 6, 10, 15, 22, 25, and 26 were randomly varied using a degenerate approach, where the corresponding codons were replaced with NNK, where N is any base and K is either deoxyguanosine (G) or deoxythymidine (T). Residue number 14 was randomly varied using a degenerate approach, where that codon was replaced with CSK, where C is deoxycytidine, S is either C or G, and K is either G or T. The degenerate sequence is illustrated in FIG. 18A. Also included in the vector was: a T7 promoter, a spacer, a Shine-Dalgarno ribosome binding site (RBS), an ATG at the start site of translation, a His Tag™ (i.e. hexahistidine, HHHHHH; SEQ ID NO: 26), a cleavage site sequence for the Tobacco Etch Virus (TEV) protease, a Melittin variant sequence, two sequential stop codons (i.e. TAA, TAG, or TGA), a spacer, a T7 termination sequence. See, e.g., FIG. 18B. The theoretical number of unique sequences in library is 10 billion (i.e. $10^{10}$).

The master library was amplified using 1.5 µl of the master library at 6.9 ng/µl concentration and the standard Illustra Genomiphi protocol (on the World Wide Web at: gelifesciences.com/gehcls_images/GELS/Related%20Content/Files/1314774443672/litdocGPHI_V2_25660030_revB_20110831102610.pdf) and cut with the restriction enzyme CLA1.

To assess the diversity of the linearized sub-library, a small sample was sequenced using Illumina MiSeq next-generation sequencing instrument. In a multiplexed run, approximately 3.1 million reads were devoted to sequencing the linearized sub-library; roughly 1.9 million sequences were unique. The diversity of the linearized sub-library was assessed using a computer program:

DNA sequences were translated into amino acid sequences
Net charge was calculated
Hydrophobic residues were counted
Out of the eight (8) variable residues listed above, the ones identical to wild-type Melittin were counted.

Figure 19:
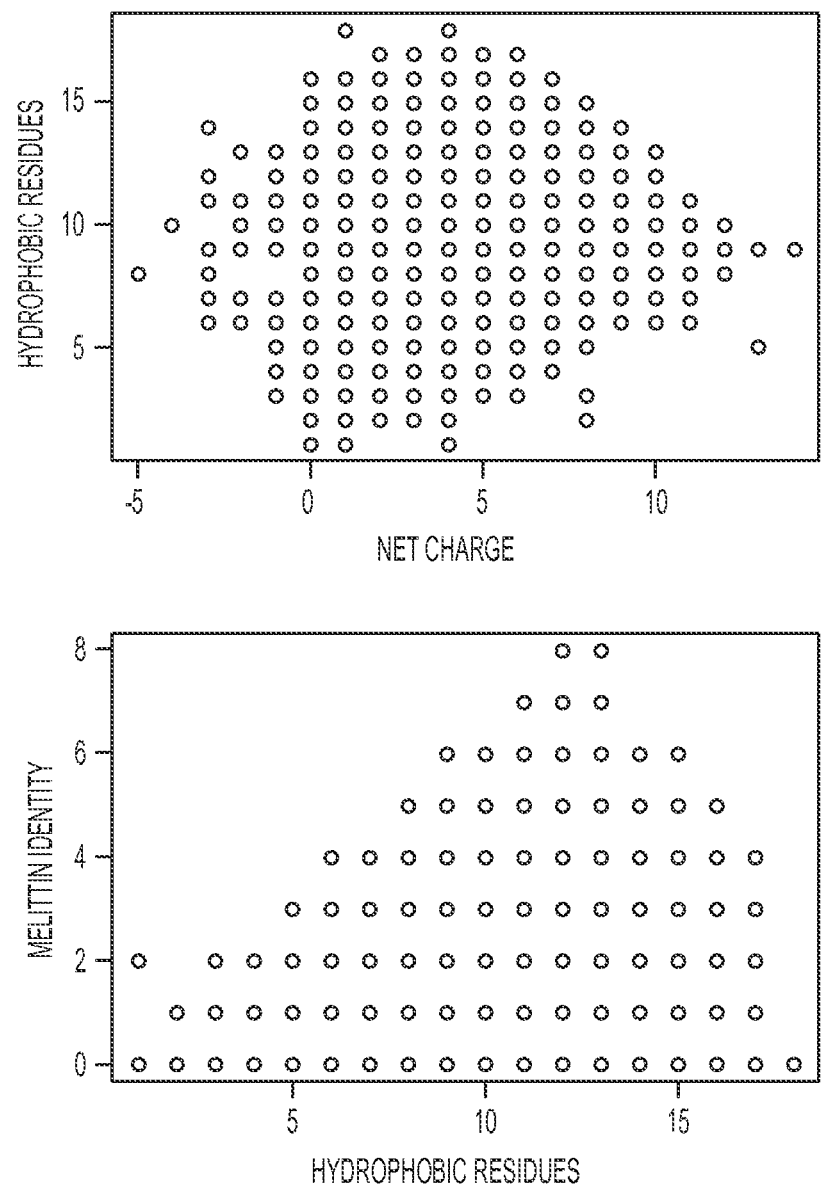
FIG. 19: Scatter-plots showing the distribution of the hydrophobic residue count vs. net charge (upper panel), and Melittin identity vs. hydrophobic residue count (lower panel). The figure shows how a wide range of charges and hydrophobicity is represented in the linearized sub-library.

Scatter-plots showing the distribution of the hydrophobic residue count vs. net charge, and Melittin identity vs. hydrophobic residue count are shown in FIG. 19. This figure shows how a wide range of charges and hydrophobicity is represented in the linearized sub-library. Some sequences have all 8 of the varied residues identical to Melittin; among those some have 12 hydrophobic residues like Melittin. Others have picked up mutations outside the varied residues, which have resulted in 13 hydrophobic residues, even as all 8 of the intentionally varied residues are identical to Melittin.

Bead-Based Emulsion PCR

Figure 20:
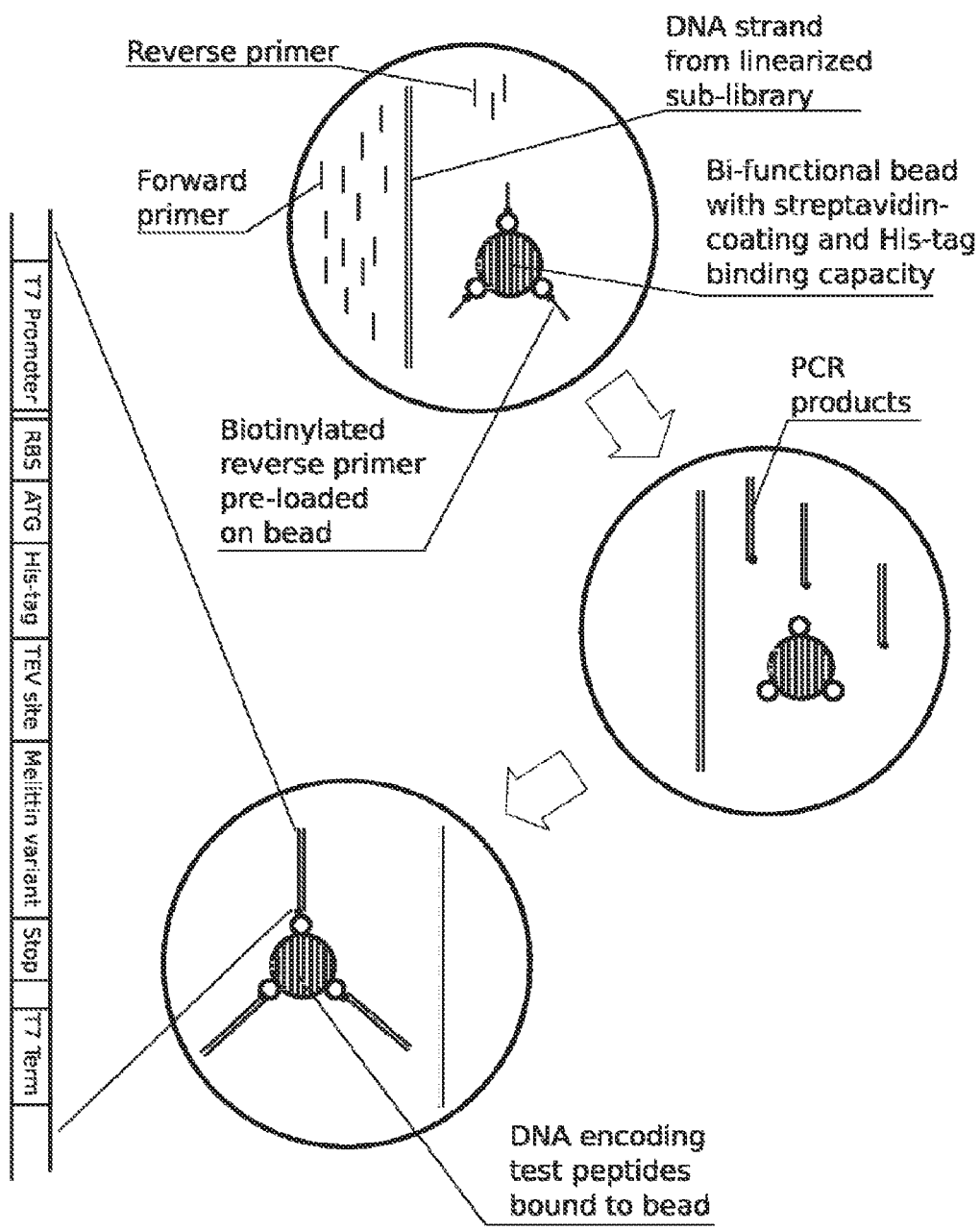
FIG. 20: A schematic of an example bead-based emulsion PCR of the embodiments.

Protocols for bead-based emulsion PCR can be found for example in Williams et al. 2006, incorporated herein by reference. A diagram of the process and the resulting product are shown in FIG. 20.

Equipment:
Vibroturbulator (Union Scientific Corp.)
Microcentrifuge (Eppendorf)
PCR machine (Applied Biosystems)

Reagents:
Bi-functional beads with a streptavidin coating and His-tag binding capacity
DNA reverse primer plus linker with 5' dual biotin (IDT)
DNA reverse primer (IDT)
DNA forward primer (IDT)
ABIL EM 90, a surfactant (Degussa)
BSA (Sigma-Aldrich)
dNTPs (Roche)

Mineral oil (Sigma-Aldrich)
Pfu Turbo DNA polymerase (2.5 U/uL; Stratagene)
Span™ 80, a surfactant (Fluka)
Breaking buffer (10 mM Tris, pH 7.5; 100 mM NaCl; 1% TritonX-100)
PCR Buffer (20 mM Tris, pH 8.4; 50 mM KCl)
Linearized sub-library (see library preparation section)
Procedure:
1. Preload bi-functional beads with biotinylated reverse primer
2. Prepare the oil-surfactant mixture by mixing in a 50-mL tube at 25° C.:

| | |
|---|---|
| Span 80 | 1% w/w |
| ABIL EM 90 | 4% w/w |
| Mineral oil | 95% w/w |

Figure 21:
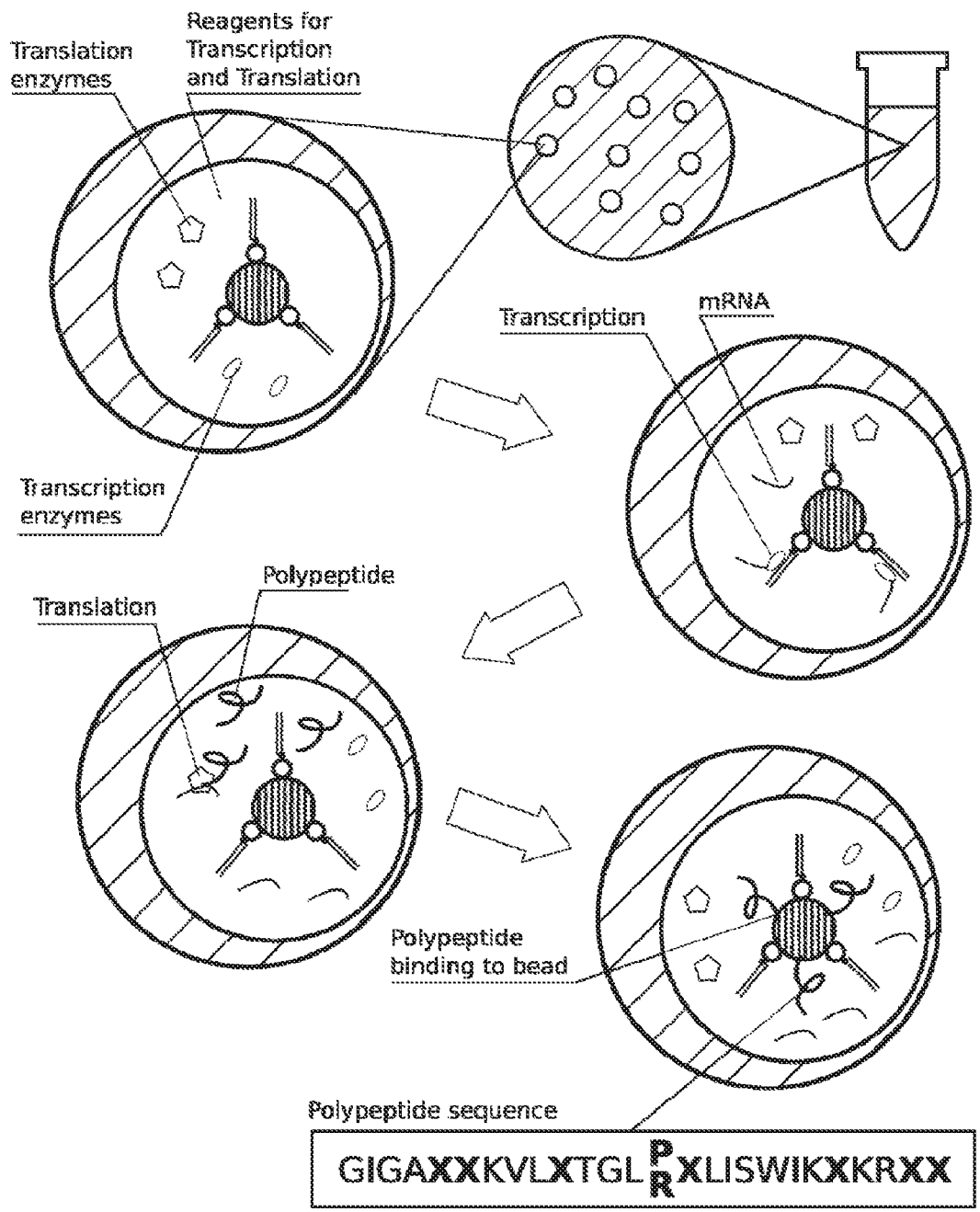
FIG. 21: A schematic of an example emulsion-based polypeptide expression of the embodiments (SEQ ID NO: 25).

3. Prepare standard PCR™ reaction mix with modifications as follows:
Bring up the DNA in TE buffer to standard stock concentration
Set up PCR reaction with the linearized sub-library as the DNA template. Add ~1.5×10$^6$ molecules from the library to the reaction
Add ~1.5×10$^6$ beads (see above).
Add forward and reverse primers that amplify a 1015 base pair segment of the vector DNA sequence, including the T7 promoter, RBS binding site, hexahistidine, TEV protease cleavage site, the degenerate sequence, and the T7 terminator
4. Create an emulsion as follows:
Dispense 900 μl of oil-surfactant mixture into a micro-centrifuge tube.
Add 100 μl of the PCR reaction mix to the tube
Place the micro-centrifuge tube in a horizontal tube rack on the Vibroturbulator.
Shake the tubes at an amplitude of 0.07-0.09 inches for 2.5 minutes to create the emulsion.
This process creates an emulsion with drop diameter in the range of 5-100 nm, where the majority of beads are one per drop.
5. Transfer to PCR tubes and a PCR machine and run the following protocol:
94° C. for 5 min
Cycle 40 times:
  94° C. for 30 sec
  57° C. for 30 sec
  72° C. for 2 min
72° C. for 7 min
Cool to 4° C.
5. Pool the PCR products and centrifuge. Dispose of the upper oil phase.
6. Extract beads from emulsion with 3 sequential washes with Breaking buffer.
7. Wash beads with PCR Buffer
8. Purify beads by centrifugation, wash and store in nuclease-free water.
Emulsion Expression
A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004) DOI: 10.1093/protein/gzho25, each of which is incorporated herein by reference. An example schematic is shown in FIG. 21.

Equipment:
Vibroturbulator (Union Scientific Corp.)
Reagents:
RTS 100 HY Cell Free Expression kit (5 Prime)
Span 80 (Sigma)
Mineral Oil (Sigma)
Abil EM90 (Degussa)
RNasin Plus (Promega)
Halt Protease Inhibitor Cocktail, EDTA free (Thermo)
Rifampicin (Sigma)
Herring Sperm DNA
Breaking buffer (10 mM Tris, pH 7.5; 100 mM NaCl; 1% TritonX-100)
DNA-loaded beads from bead-based emulsion PCR section
Procedure:
1. Supplement the 5 Prime RTS 100 HY extract kit with 20 U RNasin Plus, Halt Protease inhibitor, 2 μg/mL Rifampicin, 1 ug Herring Sperm DNA with beads at 4° C.
2. Prepare oil phase by dissolving 4% Abil EM90 (v/v), 1% (v/v) Span 80 in mineral oil.
3. Create an emulsion as follows:
Dispense 950 μl of oil-surfactant mixture into a micro-centrifuge tube.
Add 50 μl of supplemented expression kit to the tube
Place the microfluidic tube in a horizontal tube rack on the Vibroturbulator.
Shake the tubes at an amplitude of 0.07-0.09 inches for 2.5 minutes to create the emulsion.
4. Incubate at room temperature for 4 hours.
5. Dispose of the upper oil phase.
6. Extract beads from emulsion with 3 sequential washes with Breaking buffer.
7. Wash beads with PCR Buffer
8. Purify beads by centrifugation, wash and store in PBS.
Cell Emulsification and Screening
Equipment:
Incubator/shaker (New Brunswick Scientific)
30° C. water bath (VWR Scientific)
Reagents:
Glycerol stock of *E. coli* BL21(DE3)Tuner_His_MBP_pJexpress414
  (i.e. *E. coli* BL21(DE3)Tuner strain [Novagen/EMD-Millipore/Merck], transfected with pJexpress414 vector carrying His-tagged Maltose Binding Protein [DNA2.0 Inc.])
M9 Minimal Media
LB Media
1000× Ampicillin
0.1 M DTT
1 M IPTG
Mineral oil+4% Abil EM90+1% Span80
14 mL polypropylene round bottom tube
HaloTEV Protease
BacLight Viability kit (optional)
Procedure:
Day 1
1) Start an overnight culture of the bacterial strain from glycerol stock in 5 mL of LB+Amp (1 μL of 1000× Amp per 1 mL of LB) in the 14-mL round bottom tube with cap.
2) Incubate overnight in shaker at 30° C. with shaking at 200 rpm.
Day 2
1) Establish induction culture, to induce expression of His-tagged MBP, by adding 1 mL of overnight culture to 4 mL of LB+5 μL of 1000× Amp in a 14-mL round bottom tube with cap. Incubate for 1 hour at 30° C. in shaker.

2) Induce culture by adding 2.5 µL of 1 M IPTG to the culture. Incubate for 2 hours at 30° C. in the shaker.
3) Dilute bacteria to $OD_{600}=0.05$ using the M9 mix (prepare as described below) for use in the screen. This dilution should be made just before beads are ready to be screened.

| M9 mix | |
|---|---|
| 0.1M DTT | 10 µL |
| M9 Minimal Media | 990 µL |
| Baclight Dyes (optional) | 1.5 µL (each dye) |

4) Prepare the HaloTEV/Bacteria sample for screening:

| | Volume per Sample (µL) |
|---|---|
| Bacterial Dilution in M9 Mix | 90 |
| HaloTev | 10 |

Figure 22:
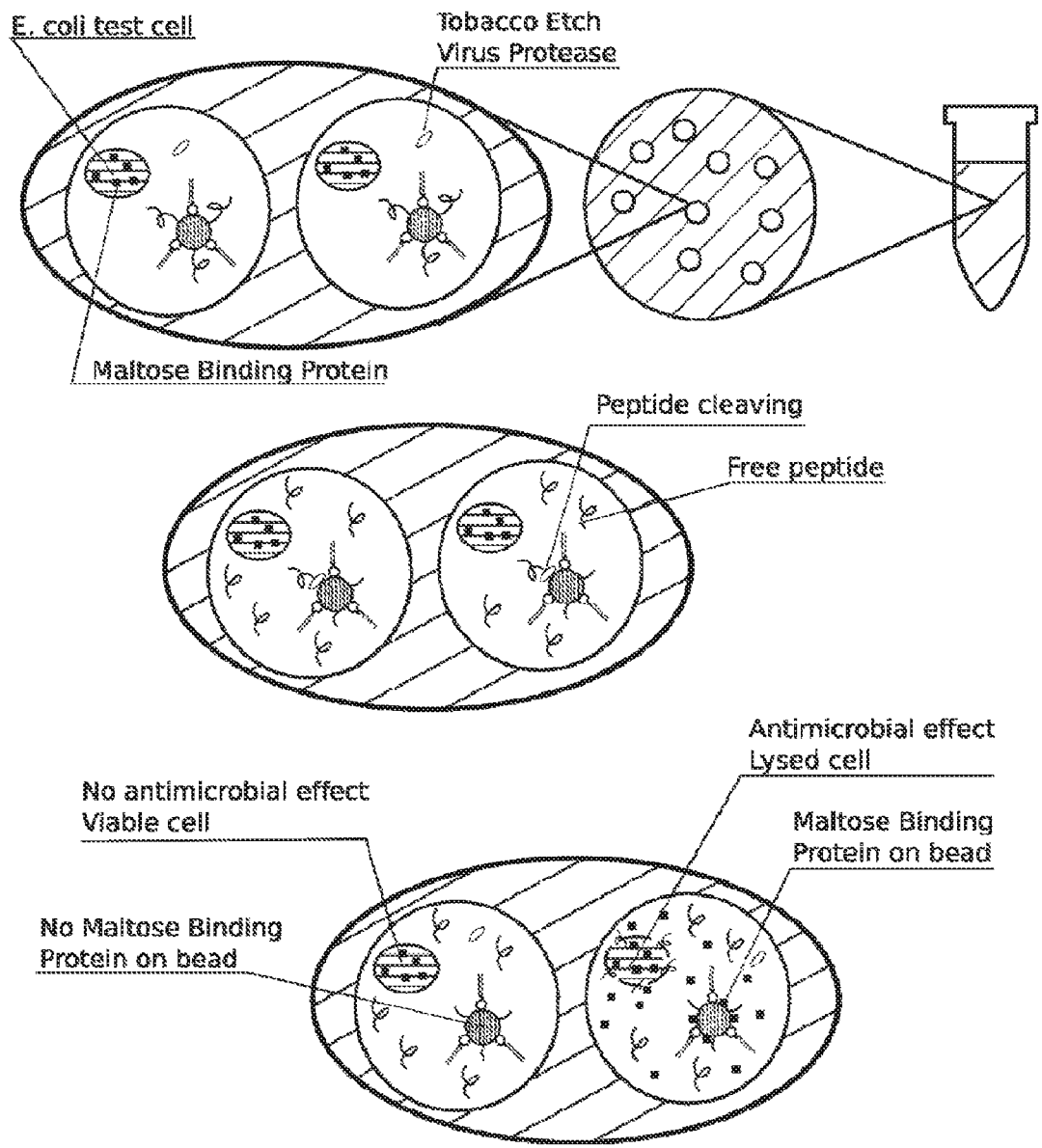
FIG. 22: A schematic of an example emulsion-based screening protocol of the embodiments.

5) Add 100 µl of HaloTEV/Bacteria Dilution to each set of beads coming from Emulsion expression. Quickly resuspend beads.
6) Add 900 µl of the Mineral oil mix to each sample. Flick bottom to roughly mix oil and aqueous layers.
7) Make emulsions using the vibroturbulator, by shaking the tubes at an amplitude of 0.07-0.09 inches for 2.5 minutes. This provides in the range of 8-40 bacterial cells and, on average, one bead per microcapsule in the emulsion.
8) Incubate for 4 hours at 30° C. to allow: (a) dissociation of peptide molecules from the beads due to the activity of the TEV protease; (b) exposure of the cells to the peptide; (c) lysis of those bacteria that are exposed to peptides possessing antimicrobial activity; (d) release of His-tagged Maltose Binding Protein (MBP) from lysed cells; and (e) binding of released MBP to the beads via the His-tag. A schematic illustrating the screening process is shown in FIG. 22.

Figure 23:
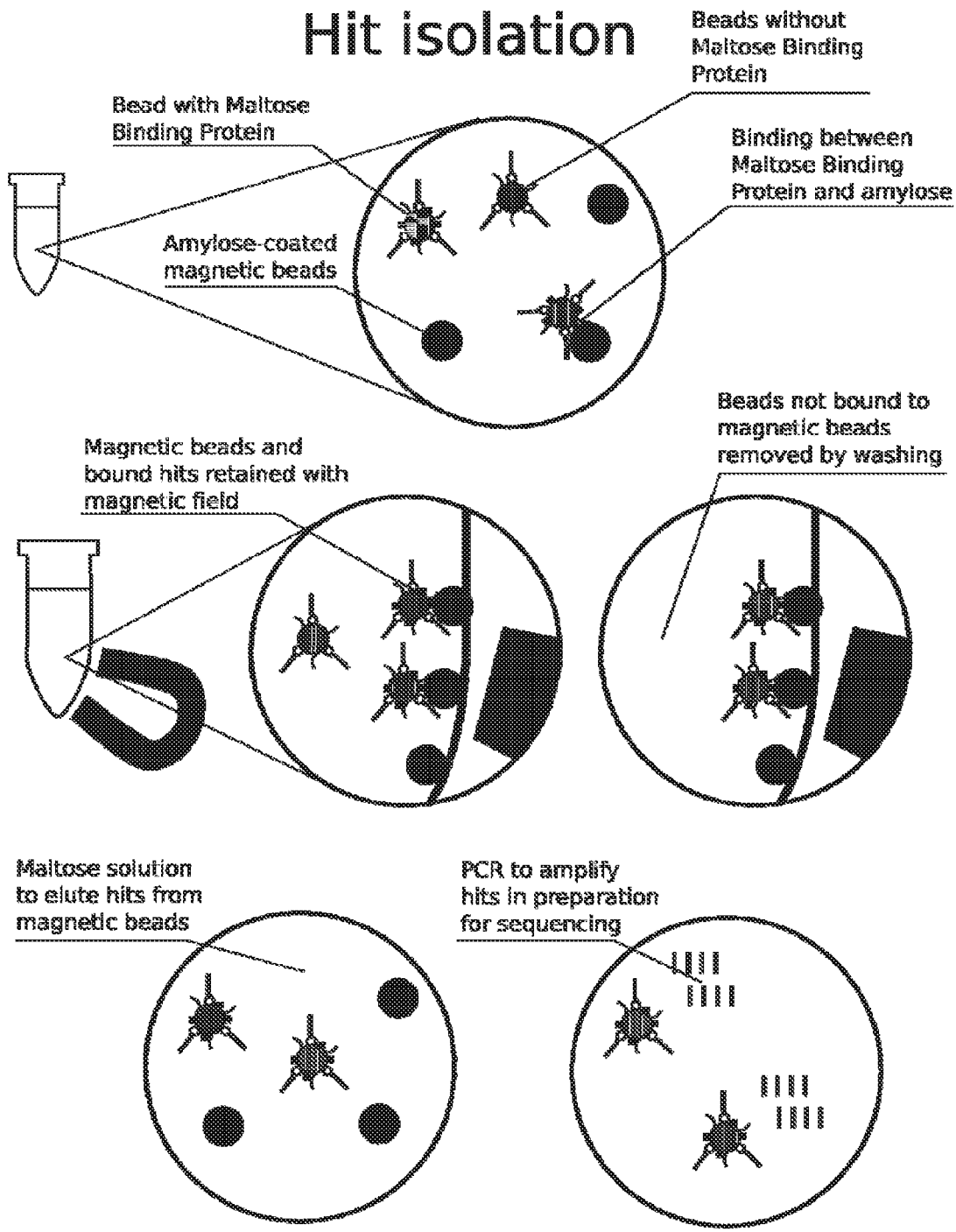
FIG. 23: A schematic of an example "hit" isolation protocol of the embodiments for identification of biologically active polypeptides.
Figure 24:
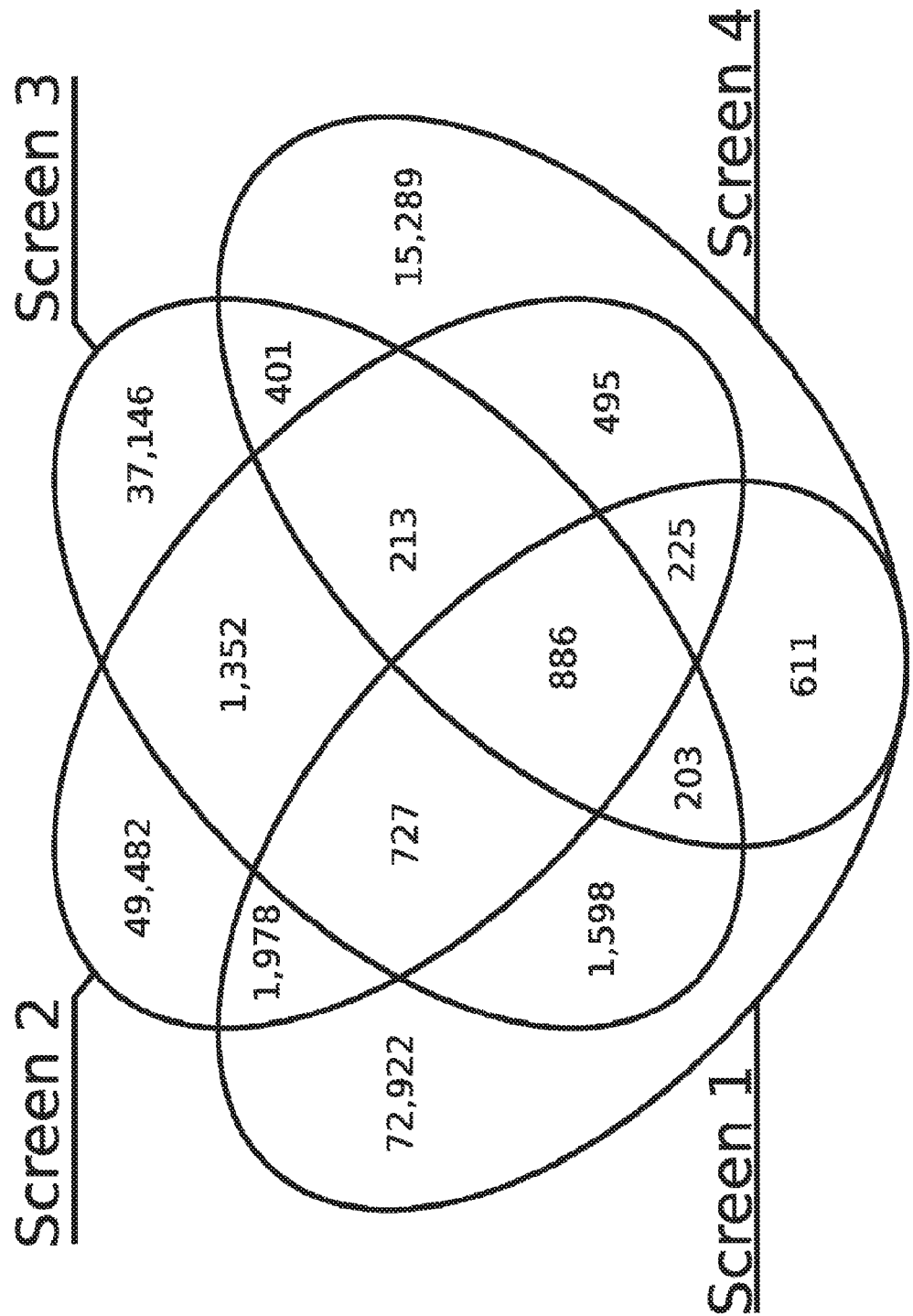
FIG. 24: A Venn diagram showing hit counts in each of the four screens detailed in Example 3.

Hit Isolation
Equipment:
Magnetic bead collection apparatus
PCR machine
Reagents:
Standard PCR reagents
Amylose-coated magnetic beads
Breaking Buffer (10 mM Tris, pH 7.5; 100 mM NaCl; 1% TritonX-100)
Procedure:
1. Break emulsion by:
i. Centrifuge, remove oil layer
ii. Break emulsion with several washes of Breaking buffer
iii. Wash beads with PBS
2. Combine bi-functional beads with amylose-coated magnetic beads and incubate for 45 min.
3. Collect hits by isolating amylose-coated magnetic beads and attached bi-functional beads with the magnetic bead collection apparatus.
4. Elute hits from magnetic beads by incubating with PBS+10 mM Maltose for 45 min.
5. PCR amplify the DNA from the bi-functional beads collected as hits using the appropriate primers to prepare the DNA for sequencing.
6. The amplified DNA was sent to a sequencing service company.
The process used to isolate hits is illustrated in FIG. 23.
Hit Identification
Equipment:
Personal computer with DNA analysis software Procedure:
1. Retrieve data files containing raw DNA sequences from the sequencing service company.
2. Identify degenerate Melittin sequences and translate into amino acid sequences.
3. Collect information about the occurrence of each unique sequence in each experiment and derive information about each sequence: net charge, hydrophobic residue count, how many residues are identical to wild-type Melittin.
4. To minimize false positives, four replicate screens were performed and only hits that occurred in two or more screens were moved forward for validation. FIG. 24 is a Venn diagram showing hit counts in each of the four screens and how they overlap.
Hit Validation
Equipment:
Absorption and fluorescence plate reader—Tecan Safire
$CO_2$ Incubator
Reagents:
Six chemically synthesized peptides—Biosynthesis Inc.
E. coli MG1655 (ATCC)
LB media (Sigma-Aldrich)
Alamar Blue assay kit (Life Tech)
Procedure:
1) Three hits were selected for validation. The selection criteria were:
At least three of the randomly varied amino acids must be identical to Melittin
In four replicate screens, the hits were identified in either two or three screens.
The sequences of the three hits were:

```
Hit 1:
                                         (SEQ ID NO: 2)
GIGAVLKVLTTGLPTLISWIKSKRQK

Hit 2:
                                         (SEQ ID NO: 3)
GIGALIKVLTTGLPMLISWIKRKRNK

Hit 3:
                                         (SEQ ID NO: 4)
GIGAWTKVLTTGLPGLISWIKRKRLR
```

2) Three sequences were randomly selected as control. The control sequences had the same residues randomly varied as described for the library. The control sequences also had at least three of the randomly varied amino acids identical to Melittin.
The sequences of the control peptides were:

```
Control 1:
                                         (SEQ ID NO: 5)
GIGATVKVLSTGLRFLISWIKRKRKY Control 2:
                                         (SEQ ID NO: 6)
GIGAIAKVLSTGLPRLISWIKGKRIR Control 3:
                                         (SEQ ID NO: 7)
GIGAVLKVLGTGLPALISWIKFKRFP
```

3) Start an overnight culture of E. coli MG1655 in 5 mL of LB and grow at 37° C. with shaking at 200 rpm.
4) In the morning dilute overnight culture to $OD_{600}=0.00075$ in 10 mL LB+1 mL Alamar Blue Stain.
5) Make seven (7), 1:2 serial dilutions of each peptide starting at 500 nM in a final volume of 70 µL of PBS.

6) Add 20 μL of serial dilution of peptides in triplicate to a white small volume 96-well plate. Add 20 μl of PBS alone to the 8$^{th}$ well.
7) Add 120 μL of *E. coli*/Alamar blue dilution to each of the test wells.
8) Incubate overnight (18 hrs) at 35° C.
9) At 18 hours determine the Minimal Inhibitory Concentration (MIC) for each peptide as shown in Table 1.

TABLE 1

MIC at 18 hrs in *E. coli*

| Peptide | Class | Ave MIC (μM) | Std Dev |
|---|---|---|---|
| Melittin | Positive Control | 13 | 2 |
| Hit 1 | Hit | 12 | 2 |
| Hit 2 | Hit | 14 | 5 |
| Hit 3 | Hit | 20 | 2 |
| Cont 1 | Negative Control | >30 | |
| Cont 2 | Negative Control | 15 | |
| Cont 3 | Negative Control | >30 | |

Figure 25:
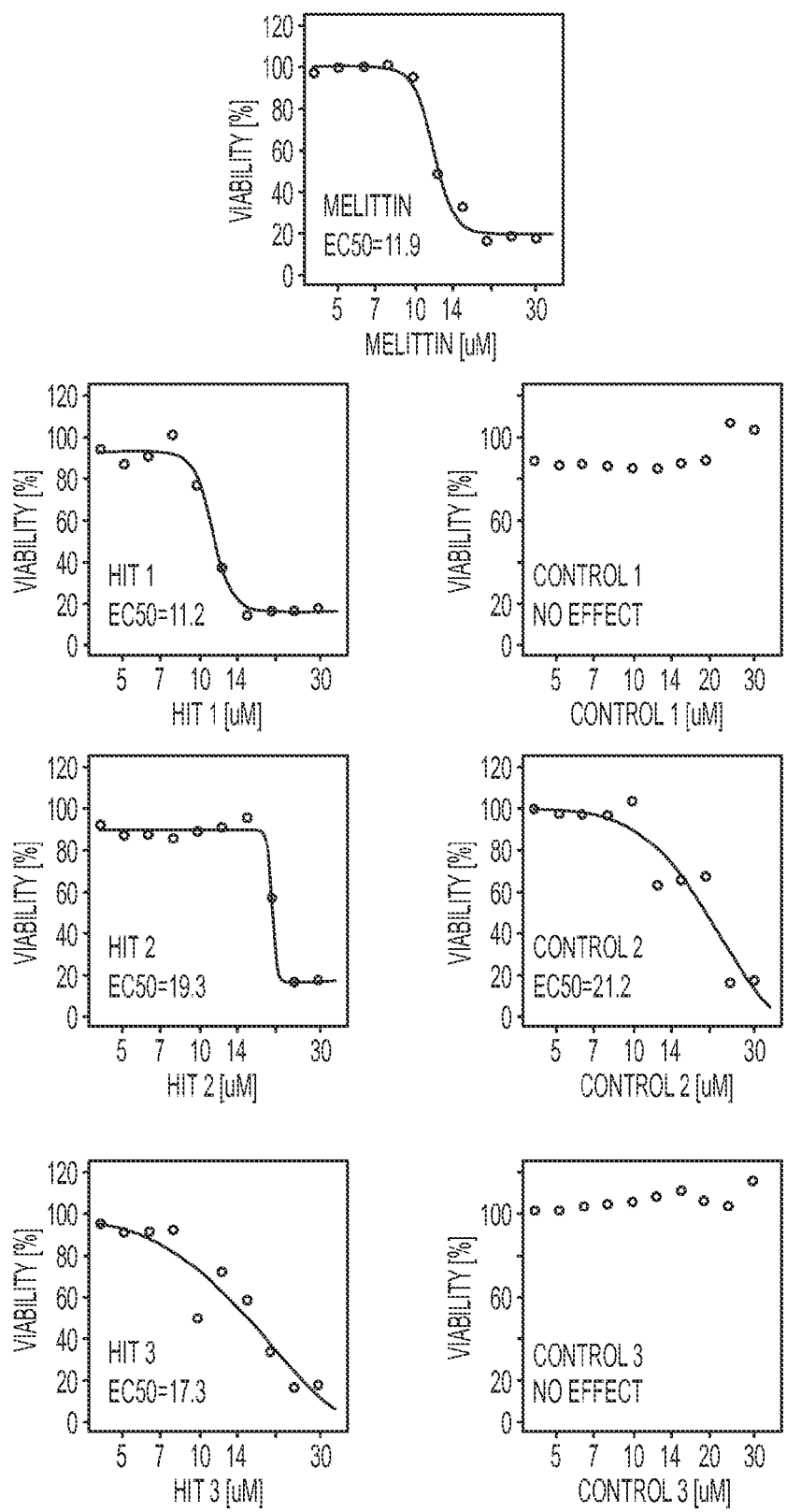
FIG. 25: Graphs show the calculated effective concentration $EC_{50}$ data for Melittin, hits 1, 2, and 3, and controls 1, 2, and 3 isolated in Example 3.

10) The 50% effective concentration ($EC_{50}$) was also calculated for each peptide based on a curve-fit of a four-parameter log-logistic function to the dose curve as measured by the adsorption plate reader. $EC_{50}$ data for Melittin, hits 1, 2, and 3, and controls 1, 2, and 3 are shown in FIG. 25.

Example 4

Biological Activity Testing in Micro Titer Plates

Nucleotide Sequence Preparation
Reagents:
DNA constructs representing two different variants of tumor necrosis factor alpha (TNF-alpha), which is optimized for in vitro expression; obtained from DNA 2.0 (see the World Wide Web at dna20.com) and cloned into the pIVEX vector (5 Prime, Inc.).
Two DNA sequence constructs were designed.
Construct 1

(SEQ ID NO: 8)
MHHHHHHENLYFQGVRSSSRTPSDKPVAHVVANPQAEGQLQWLNRRAN

ALLANGVELRDNQLVVPSEGLYLIYSQVLFKGQGCPSTHVLLTHTISR

IAVSYQTKVNLLSAIKSPCQRETPEGAEAKPWYEPIYLGGVFQLEKGD

RLSAEINRPDYLDFAESGQVYFGIIAL**

Construct 2

(SEQ ID NO: 9)
MHHHHHHGSGGSGENLYFQGVRSSSRTPSDKPVAHVVANPQAEGQLQW

LNRRANALLANGVELRDNQLVVPSEGLYLIYSQVLFKGQGCPSTHVLL

THTISRIAVSYQTKVNLLSAIKSPCQRETPEGAEAKPWYEPIYLGGVF

QLEKGDRLSAEINRPDYLDFAESGQVYFGIIAL**

Two DNA constructs were created. Construct 1 consisted of a His-tag, TEV cleavage site and the soluble form of TNF-alpha. Construct 2 consisted of a His-tag, a spacer, TEV cleavage site and the soluble form of TNF-alpha. These constructs were used to examine how the placement of amino acid spacer regions (Seq: GSGGSG; bold-underlined in construct 2 sequence above) influences the activity of the TNF construct. Construct 1 was designed without any spacer regions. Construct 2 was designed to test the placement of a spacer region between the His-tag and TEV-protease site.

Bead-Based Emulsion PCR

Protocols for bead-based emulsion PCR can be found for example in Williams et al. 2006, incorporated herein by reference. A diagram of the process and the resulting product are shown in FIG. 20.
Equipment:
Vortex Genie 2 (Fisher Scientific)
Microcentrifuge (Eppendorf)
PCR machine (Applied Biosystems)
Reagents:
Bi-functional beads with a streptavidin coating and His-tag binding capacity
DNA reverse primer plus linker with 5' dual biotin (IDT)
DNA reverse primer (IDT)
DNA forward primer (IDT)
ABIL EM 90, a surfactant (Degussa)
Mineral oil (Sigma-Aldrich)
2× GoTaq Green Master Mix (Promega)
Span™ 80, a surfactant (Fluka)
1-Butanol (Sigma)
Breaking buffer (10 mM Tris, pH 7.5; 100 mM NaCl; 1% TritonX-100)
PCR Buffer (20 mM Tris, pH 8.4; 50 mM KCl)
TNF-alpha constructs cloned into pIVEX 2.3d (DNA 2.0/5 Prime)
Procedure:
1. Preload bi-functional beads with biotinylated reverse primer
2. Prepare the oil-surfactant mixture by mixing in a 50-mL tube at 25° C.:

| Span 80 | 1% w/w |
|---|---|
| ABIL EM 90 | 4% w/w |
| Mineral oil | 95% w/w |

3. Prepare standard PCR™ reaction mix with modifications as follows:
Bring up the DNA in TE buffer to standard stock concentration
Set up PCR reaction with the DNA constructs in the pIVEX vector (100 ng/sample)
Add ~3×10$^5$ beads (see above).
Add forward and reverse primers that amplify a 1408 and 1426 base pair segment of the vector DNA sequence for Constructs 1 and 2, respectively, including the T7 promoter, RBS binding site, hexahistidine, TEV protease cleavage site, the TNF-alpha sequence, and the T7 terminator
4. Create an emulsion as follows:
Dispense 950 μl of oil-surfactant mixture into a microcentrifuge tube.
Add 50 μl of the PCR reaction mix to the tube
Flick tube a few times to disperse water in oil
Vortex the tube for 15 seconds on highest setting (8).
This process creates an emulsion with drop diameter in the range of 5-100 μm, where the majority of beads are one per drop.
5. Transfer to PCR tubes and a PCR machine and run the following protocol:
94° C. for 5 min
Cycle 40 times:
94° C. for 30 sec
57° C. for 30 sec
72° C. for 4 min 72° C. for 7 min
Cool to 4° C.
5. Pool the PCR products and centrifuge. Dispose of the upper oil phase.
6. Extract beads from emulsion with 2 sets of alternating washes of 1-Butanol and Breaking buffer.
7. Wash beads with PCR Buffer
8. Purify beads by centrifugation, wash and store in nuclease-free water.

Emulsion Expression

A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004) DOI: 10.1093/protein/gzho25, each of which is incorporated herein by reference. An example schematic is shown in FIG. 21.

Equipment:
Vortex Genie 2 (Fisher Scientific)
Reagents:
RTS 100 HY Cell Free Expression kit (5 Prime)
Span 80 (Sigma)
Mineral Oil (Sigma)
Abil EM90 (Degussa)
RNasin Plus (Promega)
Halt Protease Inhibitor Cocktail, EDTA free (Thermo)
Rifampicin (Sigma)
Herring Sperm DNA
DNA-loaded beads from bead-based emulsion PCR section
Procedure:
1. Supplement the 5 Prime RTS 100 HY extract kit with 20 U RNasin Plus, Halt Protease inhibitor, 2 ng/mL Rifampicin, 1 μg Herring Sperm DNA with beads at 4° C.
2. Prepare oil phase by dissolving 4% Abil EM90 (v/v), 1% (v/v) Span 80 in mineral oil.
3. Create an emulsion as follows:
Dispense 950 μl of oil-surfactant mixture into a microcentrifuge tube.
Add 50 μl of supplemented expression kit to the tube
Flick tube a few times to disperse water in oil
Vortex the tube for 15 s on highest setting (8).
4. Incubate at room temperature for 3 hours.
5. Centrifuge tube and remove top oil layer.
6. Break emulsion with 3 washes of Breaking buffer.
7. Wash beads twice with PBS.
8. Resuspend beads in PBS.

Bioactivity Testing
Equipment:
Cell culture incubator (Fisher Scientific)
Microplate reader (Tecan Safire)
Black, clear bottom, 96-well microtiter plate (Corning)
Reagents:
Jurkat cells transfected with GFP reporter construct for NF-kappa-B (System Biosciences, Inc.)
RPMI 1640+10% Fetal Bovine Serum+Penicillin/Streptomycin (Life Tech)
HaloTEV Protease (Promega)
Phosphate Buffered Saline (PBS) (Sigma)
0.1 M Dithiothreitol (Sigma)
TNF-alpha (50 ug/mL) (Millipore)
TNF construct 1 (DNA and protein) on beads
TNF construct 2 (DNA and protein) on beads
Procedure:
1) Dilute NF-κB-Jurkat cells to 100,000 cells/ml using the supplemented RPMI 1640 growth media.
2) Add 25 μl of PBS to column 1, rows 2-12.
3) Add 37.5 μl of TNF-alpha to column 1, row 1. Make 1 to 3 serial dilutions down the column by transferring 12.5 μl.
4) Dilute and add 8 μl of construct 1 and construct 2 beads to row 1, in columns 2 and 3, respectively, so that approximately 150 TNF-beads are delivered.
5) Make the following HaloTev protease mix:

| HaloTev | 350 uL |
|---|---|
| 0.1M DTT | 35 uL |

6) Add 5 μl of the HaloTev protease mix to each of the test wells.
7) Add 100 μl of NF-κB-Jurkat cells to all wells of the plate.
8) Incubate the plate for 18 hours at 37 C and 5% $CO_2$.
9) Measure the GFP fluorescence of each well using the Tecan Safire plate reader.

Figure 26:
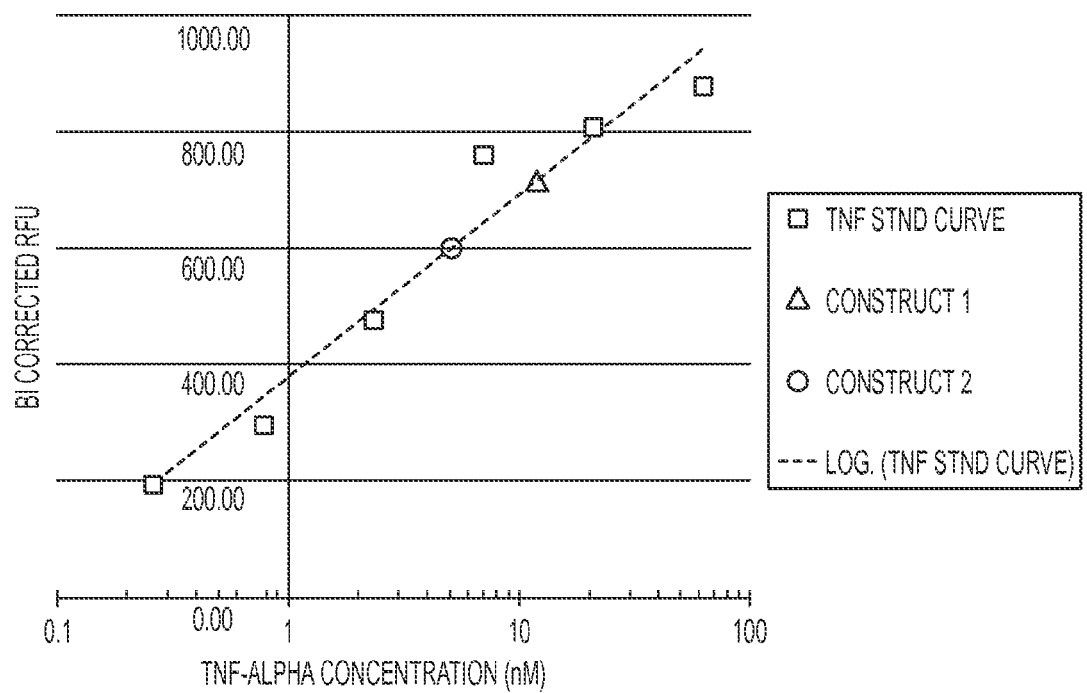
FIG. 26: Graphs show the results of a fluorescence based TNF-alpha reporter assay using constructs detailed in Example 4.

The effective concentration of TNF-alpha protein that was expressed, captured, and successfully cleaved from the bead and able to stimulate the NF-κB reporter cell line was calculated using a fluorescence-based microtiter plate assay and a standard curve. The Jurkat cell line has been engineered so that GFP is expressed when the NF-κB pathway has been activated. The addition of TNF-alpha activates the NF-κB signaling pathway and initiates expression of the GFP reporter. A pure commercial source of TNF-alpha was used to generate a standard curve measuring the GFP fluorescence generated by a range of concentrations of TNF-alpha (filled squares in FIG. 26). The fluorescence generated by the test constructs was fit on the standard curve and the concentration of active TNF generated from 150 beads was calculated (open triangles and circles in FIG. 26). The theoretical load per bead and theoretical concentration that can be delivered per bead in a 100 μm emulsion drop was calculated using the concentration calculated for each construct (Table 2).

TABLE 2

| Sample | Molecules/Bead | nMoles/Bead | Concentration (nM) from one Bead in 0.1 mm drop |
|---|---|---|---|
| Construct 1 | 5.2E+09 | 8.6E−06 | 16516 |
| Construct 2 | 2.2E+09 | 3.7E−06 | 7038 |

Example 5

DNA Hand-Off and Isolation

Protocols for bead-based emulsion PCR can be found for example in Williams et al. 2006, incorporated herein by reference. A diagram of the process and the resulting product are shown in FIG. 20.

Equipment:
Vortex Genie 2 (Fisher Scientific)
Microcentrifuge (Eppendorf)
PCR machine (Applied Biosystems)
Tube rotator
Reagents:
Bi-functional beads with a streptavidin coating and His-tag binding capacity
DNA reverse primer plus linker with 5' dual biotin (IDT)
DNA reverse primer (IDT)
DNA forward primer (IDT)
DNA forward primer plus linker with 5' biotin (IDT)

ABIL EM 90, a surfactant (Degussa)
Mineral oil (Sigma-Aldrich)
2× GoTaq Green Master Mix (Promega)
Span™ 80, a surfactant (Fluka)
1-Butanol (Sigma)
Breaking buffer (10 mM Tris, pH 7.5; 100 mM NaCl; 1% TritonX-100)
PCR Buffer (20 mM Tris, pH 8.4; 50 mM KCl)
TNF-alpha construct cloned into pIVEX 2.3d (DNA 2.0/5 Prime); the construct contains a His-tag, spacer, TEV cleavage site, and the soluble form of TNF-alpha; the sequence of the construct is:

(SEQ ID NO: 10)
MHHHHHHGSGGSGENLYFQGVRSSSRTPSDKPVAHVVANPQAEGQL

QWLNRRANALLANGVELRDNQLVVPSEGLYLIYSQVLFKGQGCPST

HVLLTHTISRIAVSYQTKVNLLSAIKSPCQRETPEGAEAKPWYEPI

YLGGVFQLEKGDRLSAEINRPDYLDFAESGQVYFGIIAL** streptavidin (Sigma)
biotinylated *galanthus nivalis* lectin (Vector Labs)
Procedure:
1. Preload bi-functional beads with biotinylated reverse primer
2. Prepare the oil-surfactant mixture by mixing in a 50-mL tube at 25° C.:

| Span 80 | 1% w/w |
| ABIL EM 90 | 4% w/w |
| Mineral oil | 95% w/w |

3. Prepare standard PCR™ reaction mix with modifications as follows:
Bring up the TNF-alpha construct DNA in TE buffer to standard stock concentration.
Set up PCR reaction with the DNA construct in the pIVEX vector (100 ng/sample)
Add ~3×10$^5$ beads/sample (see above).
Add forward and reverse primers that amplify a 1426 base pair segment of the vector DNA sequence, including the T7 promoter, RBS binding site, hexahistidine, TEV protease cleavage site, the TNF-alpha sequence, and the T7 terminator. Two samples were prepared; sample 1 used a basic forward primer; sample 2 used a 5' biotinylated forward primer.
4. Create an emulsion as follows:
Dispense 950 μl of oil-surfactant mixture into a microcentrifuge tube.
Add 50 μl of the PCR reaction mix to the tube
Flick tube a few times to disperse water in oil
Vortex the tube for 15 s on highest setting (8).
This process creates an emulsion with drop diameter in the range of 5-100 μm, where the majority of beads are one per drop.
5. Transfer to PCR tubes and a PCR machine and run the following protocol:
94° C. for 5 min
Cycle 40 times:
94° C. for 30 sec
57° C. for 30 sec
72° C. for 4 min
72° C. for 7 min
Cool to 4° C.

Figure 27:
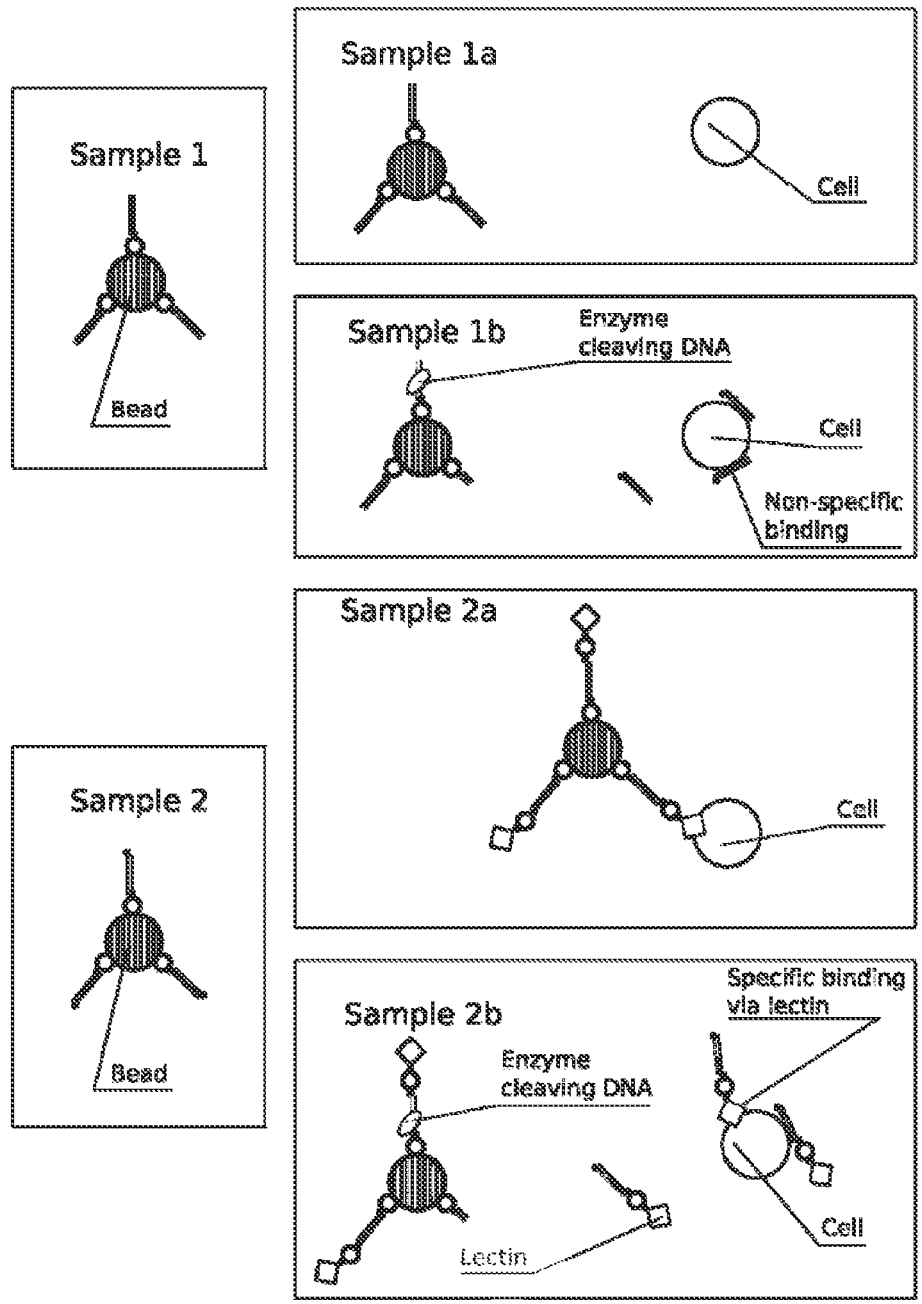
FIG. 27: A schematic of an example "hit" isolation protocol where nucleic acid molecules are bound to test cells.
Figure 28:
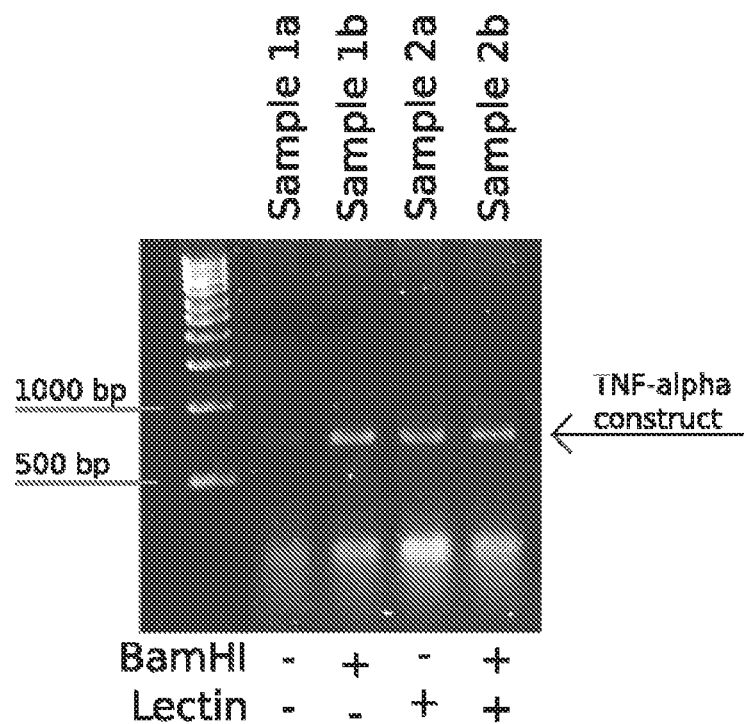
FIG. 28: Reproduction of an agarose gel electrophoresis showing successful hit isolation using a protocol where nucleic acid molecules are bound to test cells as detailed in Example 4.

5. Pool the PCR products and centrifuge. Dispose of the upper oil phase.
6. Extract beads from emulsion with 2 sets of alternating washes of 1-Butanol and Breaking buffer.
7. Wash beads with PCR Buffer
8. Purify beads by centrifugation, wash and store in nuclease-free water.
9. Treat beads the beads from sample 2 (that have biotinylated forward primer) sequentially with streptavidin then biotinylated lectin
DNA Isolation
Equipment:
Microcentrifuge (Eppendorf)
Incubator
PCR machine (Applied Biosystems)
Reagents:
Jurkat cells
RPMI 1640+10% Fetal Bovine Serum+Penicillin/Streptomycin (Life Tech)
BamHI (New England Biolabs)
amylose-coated magnetic beads (New England Biolabs)
His-tagged Maltose Binding Protein (His-MBP)
Magnetic bead collection apparatus
DNA reverse primer (IDT)
DNA forward primer (IDT)
2× GoTaq Green Master Mix (Promega)
Procedure:
1. Incubate Jurkat cells with PCR beads and with or without BamHI at 37° C. for 1 h at 5% $CO_2$ to cut DNA from the bead and transfer to the Jurkat cells through specific (via lectin) or nonspecific binding, and controls are run without the BamHI present. Four samples were prepared:
Sample 1a: beads from sample 1 without BamHI
Sample 1b: beads from sample 1 with BamHI
Sample 2a: beads from sample 2 with biotinylated primer, streptavidin, biotinylated lectin, and without BamHI
Sample 2b: beads from sample 2 with biotinylated primer, streptavidin, biotinylated lectin, and with BamHI
2. Incubate amylose magnetic beads with His-MBP.
3. Incubate the cells+beads with amylose-coated magnetic beads pre-loaded with His-MBP for 5 min at room temperature
4. Deplete sample of bi-functional beads, which are attached to amylose-coated magnetic beads through His-MBP, with the magnetic bead collection apparatus
5. Centrifuge unbound solution containing cells at 500×g for 1 min, wash cells with water and re-centrifuge
6. Amplify DNA from cells using primers interior to the initial linear template that amplify a 689 base pair segment, with 2× GoTaq master mix and standard PCR preparation
7. Transfer to PCR tubes and a PCR machine and run the following protocol:
94° C. for 5 min
Cycle 25 times:
94° C. for 30 sec
60° C. for 30 sec
72° C. for 1 min
72° C. for 7 min
Cool to 4° C.
8. Run a portion of the unpurified PCR products on a 1% agarose gel in TBE to verify the presence or absence of DNA on the cells
FIG. 27 shows a schematic of the DNA hand-off process and FIG. 28 shows the results from the agarose gel, which indicate that in samples 1b, 2a, and 2b, the test DNA from the TNF-alpha construct was present on the surface of the cell and supported PCR amplification of the sequence. In contrast, DNA was not present on the cells from sample 1a. Even though DNA was not cleaved from the beads in sample 2a, the specific binding via the lectin caused some beads to be carried through with the cells and not washed away as in the case of sample 1a.

Example 6

Protein Dosing from Beads

Nucleotide Sequence Preparation
Reagents:
DNA construct containing the Dasher green fluorescent protein sequence, which is optimized for in vitro expression; obtained from DNA 2.0 (see the World Wide Web at dna20.com) and cloned into the pIVEX vector (5 Prime, Inc.).
The sequence of the Dasher construct is:

(SEQ ID NO: 11)
MHHHHHHENLYFQGSAGQSSGRATALTEGAKLFEKEIPYITELEGD

VEGMKFIIKGEGTGDATTGTIKAKYICTTGDLPVPWATLVSTLSYG

VQCFAKYPSHIKDFFKSAMPEGYTQERTISFEGDGVYKTRAMVTYE

RGSIYNRVTLTGENFKKDGHILRKNVAFQCPPSILYILPDTVNNGI

RVEFNQAYDIEGVTEKLVTKCSQMNRPLAGSAAVHIPRYHHITYHT

KLSKDRDERRDHMCLVEVVKAVDLDTYQAGAMASMTGGQQMG*

The Dasher construct consisted of a His-tag, TEV cleavage site and a green fluorescent protein sequence obtained from DNA 2.0 Inc. This construct allows the yield from combined emulsion PCR and emulsion expression to be monitored using an epifluorescence microscope or fluorescence plate reader.

Bead-Based Emulsion PCR
Protocols for bead-based emulsion PCR can be found for example in Williams et al. 2006, incorporated herein by reference. A diagram of the process and the resulting product are shown in FIG. 20.
Equipment:
Vortex Genie 2 (Fisher Scientific)
Microcentrifuge (Eppendorf)
PCR machine (Applied Biosystems)
Spectrophotometer (Thermo Fisher; Nanodrop)
Reagents:
Bi-functional beads with a streptavidin coating and His-tag binding capacity
DNA reverse primer plus linker with 5' dual biotin (IDT)
DNA reverse primer (IDT)
DNA forward primer (IDT)
ABIL EM 90, a surfactant (Degussa)
Mineral oil (Sigma-Aldrich)
2× GoTaq Green Master Mix (Promega)
Span™ 80, a surfactant (Fluka)
1-Butanol (Sigma)
Breaking buffer (10 mM Tris, pH 7.5; 100 mM NaCl; 1% TritonX-100)
PCR Buffer (20 mM Tris, pH 8.4; 50 mM KCl)
Dasher construct cloned into pIVEX 2.3d (DNA 2.0/5 Prime), amplified to linear construct using DNA forward and reverse primers
Procedure:
1. Preload bi-functional beads with biotinylated reverse primer 2. Prepare the oil-surfactant mixture by mixing in a 50-mL tube at 25° C.:

| Span 80 | 1% w/w |
| ABIL EM 90 | 4% w/w |
| Mineral oil | 95% w/w |

3. Prepare standard PCR™ reaction mix with modifications as follows:
   Set up PCR reaction with the linear Dasher construct from the pIVEX vector (100 ng/sample; quantified using spectrophotometer)
   Add ~3×10$^5$ beads (see above).
   Add forward and reverse primers that amplify a 1708 base pair segment of the vector DNA sequence from the Dasher construct including the T7 promoter, RBS binding site, hexahistidine, TEV protease cleavage site, and the T7 terminator
4. Create an emulsion as follows:
   Dispense 950 µl of oil-surfactant mixture into a microcentrifuge tube.
   Add 50 µl of the PCR reaction mix to the tube
   Flick tube a few times to disperse water in oil
   Vortex the tube for 15 seconds on highest setting (8).
   This process creates an emulsion with drop diameter in the range of 5-100 nm, where the majority of beads are one per drop.
5. Transfer to PCR tubes and a PCR machine and run the following protocol:
   94° C. for 5 min
   Cycle 40 times:
     94° C. for 30 sec
     57° C. for 30 sec
     72° C. for 4 min
   72° C. for 7 min
   Cool to 4° C.
5. Pool the PCR products and centrifuge. Dispose of the upper oil phase.
6. Extract beads from emulsion with 2 sets of alternating washes of 1-Butanol and Breaking buffer.
7. Wash beads with PCR Buffer
8. Purify beads by centrifugation, wash and store in nuclease-free water.

Emulsion Expression
A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004) DOI: 10.1093/protein/gzho25, each of which is incorporated herein by reference. An example schematic is shown in FIG. 21.
Equipment:
Vortex Genie 2 (Fisher Scientific)
Reagents:
RTS 100 HY Cell Free Expression kit (5 Prime)
Span 80 (Sigma)
Mineral Oil (Sigma)
Abil EM90 (Degussa)
RNasin Plus (Promega)
Halt Protease Inhibitor Cocktail, EDTA free (Thermo)
Rifampicin (Sigma)
Herring Sperm DNA
DNA-loaded beads from bead-based emulsion PCR section
Breaking buffer (10 mM Tris, pH 7.5; 100 mM NaCl; 1% TritonX-100)

Procedure:
1. Supplement the 5 Prime RTS 100 HY extract kit with 20 U RNasin Plus, Halt Protease inhibitor, 2 ug/mL Rifampicin, 1 ug Herring Sperm DNA with beads at 4° C.
2. Prepare oil phase by dissolving 4% Abil EM90 (v/v), 1% (v/v) Span 80 in mineral oil.
3. Create an emulsion as follows:
Dispense 950 nl of oil-surfactant mixture into a microcentrifuge tube.
Add 50 μl of supplemented expression kit to the tube
Flick tube a few times to disperse water in oil
Vortex the tube for 15 seconds on highest setting (8).
4. Incubate at room temperature for 2 hours.
5. Centrifuge tube and remove top oil layer.
6. Break emulsion with 3 washes of Breaking buffer.
7. Wash beads twice with PBS.
8. Resuspend beads in PBS.
9. Three samples were prepared
Sample 1: steps 1 through 8 above were performed once
Sample 2: steps 1 through 8 above were performed twice sequentially
Sample 3: steps 1 through 8 above were performed three times sequentially Protein Yield Quantification
Equipment:
Epifluorescence microscope with camera (Zeiss Axioskop)
CellProfiler software (see World Wide Web at: cellprofiler.org)
Reagents and supplies:
Microscope slides
Cover slips (CapitolBrand M3453-2222, 22 mm Length, 22 mm Width, #1 Thick)
Procedure:
1) Beads from samples 1, 2, and 3 where dispensed separately onto microscope slides and covered with cover slips. Analyses were done on all three samples at the same time to allow equal folding of existing GFP from previous expression rounds across samples.
2) Photomicrographs were captured using an epifluorescence microscope with an attached camera.
3) The photomicrographs were analyzed using CellProfiler software to determine the integrated fluorescence intensity of each bead detected.

Figure 29:
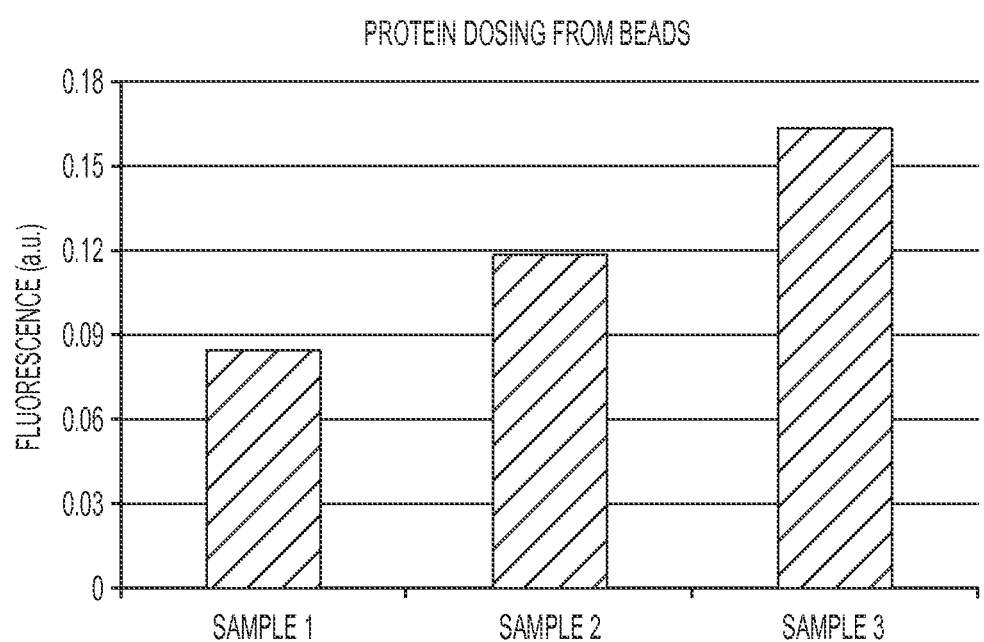
FIG. 29: A bar plot showing average fluorescence intensity of green fluorescent protein for beads from samples which were expressed 1, 2, or 3 times, respectively.

FIG. 29 shows a bar plot of average fluorescence intensity for beads from samples 1, 2, and 3, which were express once, twice, and three times, respectively. The data indicate that each consecutive round of expression increases the dose of protein carried on each bead.

Example 7

Biological Activity Testing of Single-Chain Antibody Fragment

Nucleotide Sequence Preparation
Reagents:
A test DNA construct representing a single-chain antibody fragment (scFv); a control DNA construct representing an unrelated protein (Ophioluxin subunit alpha from King Cobra); both constructs are optimized for in vitro expression and obtained from DNA 2.0 (see the World Wide Web at dna20.com) and cloned into the pIVEX vector (5 Prime, Inc.).

DNA Sequences:
scFv Test Construct:

```
                                          (SEQ ID NO: 12)
MHHHHHHGSGGSGENLYFQGGSGGSGDIQMTQSPSSLSASVGDRVTI

TCKASQNVGTNVAWYQQKPGKAPKALIYSASFLYSGVPYRFSGSGSG

TDFTLTISSLQPEDFATYYCQQYNIYPLTFGQGTKVEIKGGGGSGGG

GSGGGGSGGGGSEVQLVESGGGLVQPGGSLRLSCAASGYVFTDYGMN

WVRQAPGKGLEWMGWINTYIGEPIYADSVKGRFTFSLDTSKSTAYLQ

MNSLRAEDTAVYYCARGYRSYAMDYWQQGTLVTVSS**
```

King Cobra Control Construct:

```
                                          (SEQ ID NO: 13)
MHHHHHHGSGGSGENLYFQGDFKCPSEWYAYDQHCYRIIN**
```

The scFv test construct consisted of a His-tag, a spacer (Seq: GSGGSG; bold-underlined in sequence above), TEV cleavage site, a spacer (Seq: GSGGSG; bold-underlined in sequence above), and the single-chain antibody fragment with a variable sequence known to bind tumor necrosis factor alpha (TNF-alpha). Control construct consisted of a His-tag, a spacer (Seq: GSGGSG; bold-underlined in sequence above), TEV cleavage site, and the King Cobra protein (control) that would not be expected to bind TNF-alpha.

Bead-Based Emulsion PCR
Protocols for bead-based emulsion PCR can be found for example in Williams et al. 2006, incorporated herein by reference. A diagram of the process and the resulting product are shown in FIG. 20.
Equipment:
Vortex Genie 2 (Fisher Scientific)
Microcentrifuge (Eppendorf)
PCR machine (Applied Biosystems)
Reagents:
Bi-functional beads with a streptavidin coating and His-tag binding capacity
DNA reverse primer plus linker with 5' dual biotin (IDT)
DNA reverse primer (IDT)
DNA forward primer (IDT)
ABIL EM 90, a surfactant (Degussa)
Mineral oil (Sigma-Aldrich)
2× GoTaq Green Master Mix (Promega)
Span™ 80, a surfactant (Fluka)
1-Butanol (Sigma)
Breaking buffer (10 mM Tris, pH 7.5; 100 mM NaCl; 1% TritonX-100)
PCR Buffer (20 mM Tris, pH 8.4; 50 mM KCl)
scFv construct cloned into pIVEX 2.3d (DNA 2.0/5 Prime), amplified to linear construct using DNA forward and reverse primers
Control construct cloned into pIVEX 2.3d (DNA 2.0/5 Prime), amplified to linear construct using DNA forward and reverse primers
Procedure:
1. Preload bi-functional beads with biotinylated reverse primer
2. Prepare the oil-surfactant mixture by mixing in a 50-mL tube at 25° C.:

| | |
|---|---|
| Span 80 | 1% w/w |
| ABIL EM 90 | 4% w/w |
| Mineral oil | 95% w/w |

3. Prepare standard PCR™ reaction mix with modifications as follows:
  Set up PCR reaction with the linear DNA constructs from the pIVEX vector (100 ng/sample)
  Add ~$3\times10^5$ beads (see above).
  Add forward and reverse primers that amplify a 1708 and 1015 base pair segment of the vector DNA sequence from the scFv and Control constructs, respectively, including the T7 promoter, RBS binding site, hexahistidine, TEV protease cleavage site, the scFv (or control) sequence, and the T7 terminator
4. Create an emulsion as follows:
  Dispense 950 µl of oil-surfactant mixture into a microcentrifuge tube.
  Add 50 µl of the PCR reaction mix to the tube
  Flick tube a few times to disperse water in oil
  Vortex the tube for 15 seconds on highest setting (8).
  This process creates an emulsion with drop diameter in the range of 5-100 nm, where the majority of beads are one per drop.
5. Transfer to PCR tubes and a PCR machine and run the following protocol:
  94° C. for 5 min
  Cycle 40 times:
    94° C. for 30 sec
    57° C. for 30 sec
    72° C. for 4 min
  72° C. for 7 min
  Cool to 4° C.
5. Pool the PCR products and centrifuge. Dispose of the upper oil phase.
6. Extract beads from emulsion with 2 sets of alternating washes of 1-Butanol and Breaking buffer.
7. Wash beads with PCR Buffer
8. Purify beads by centrifugation, wash and store in nuclease-free water.

Emulsion Expression

A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004) DOI: 10.1093/protein/gzho25, each of which is incorporated herein by reference. An example schematic is shown in FIG. 21.

Equipment:
Vortex Genie 2 (Fisher Scientific)
Reagents:
RTS 100 HY Cell Free Expression kit (5 Prime)
Span 80 (Sigma)
Mineral Oil (Sigma)
Abil EM90 (Degussa)
RNasin Plus (Promega)
Halt Protease Inhibitor Cocktail, EDTA free (Thermo)
Rifampicin (Sigma)
Herring Sperm DNA
DNA-loaded beads from bead-based emulsion PCR section
Breaking buffer (10 mM Tris, pH 7.5; 100 mM NaCl; 1% TritonX-100)
Procedure:
1. Supplement the 5 Prime RTS 100 HY extract kit with 20 U RNasin Plus, Halt Protease inhibitor, 2 ug/mL Rifampicin, 1 ug Herring Sperm DNA with beads at 4° C.
2. Prepare oil phase by dissolving 4% Abil EM90 (v/v), 1% (v/v) Span 80 in mineral oil.
3. Create an emulsion as follows:
  Dispense 950 µl of oil-surfactant mixture into a microcentrifuge tube.
  Add 50 µl of supplemented expression kit to the tube
  Flick tube a few times to disperse water in oil
  Vortex the tube for 15 s on highest setting (8).
4. Incubate at room temperature for 3 hours.
5. Centrifuge tube and remove top oil layer.
6. Break emulsion with 3 washes of Breaking buffer.
7. Wash beads twice with PBS.
8. Resuspend beads in PBS.

TNF-Alpha Cell-Free Expression

Equipment:
Vortex Genie 2 (Fisher Scientific)
Incubator-Shaker (New Brunswick Scientific)
Cell culture incubator (Fisher Scientific)
Reagents:
RTS 100 HY Cell Free Expression kit (5 Prime)
RNasin Plus (Promega)
Halt Protease Inhibitor Cocktail, EDTA free (Thermo)
Rifampicin (Sigma)
Herring Sperm DNA
His-space-TEV-TNF-alpha construct 2 from example 4
Dithiothreitol (DTT)
HaloTEV
Procedure:
1. Supplement the 5 Prime RTS 100 HY extract kit with 20 U RNasin Plus, Halt Protease inhibitor, 2 ug/mL Rifampicin, 1 ug Herring Sperm DNA, and with DNA construct at 1 µg at 4° C.
4. Incubate at 37° C. for 2 hours in incubator with shaking.
5. Add His-tag binding beads (~1.5e7 beads) and incubate 10 min at room temperature
6. Wash away unbound TNF-alpha with two washes of PBS.
7. Incubate beads at 37° C. with DTT and HaloTEV in incubator overnight.
8. Centrifuge sample and use supernatant containing cleaved TNF-alpha for next section.

Testing of Antibody Fragment Binding

Equipment:
Epifluorescence microscope with camera (Zeiss Axioskop)
Reagents and supplies:
Wash buffer (PBS+20 mM Imidazole+0.05% Tween20)
anti-TNF-alpha-FITC antibody (Abcam, ab65099)
Microscope slides (Fisher Scientific)
Cover slips (CapitolBrand M3453-2222, 22 mm Length, 22 mm Width, #1 Thick)
Protein and DNA loaded bi-functional beads (scFv and control)
cleaved TNF-alpha supernatant
Procedure:
1. Beads with expressed scFv or control protein were treated with the cleaved TNF-alpha supernatant for 1 hour.
2. Beads were washed twice with wash buffer
3. Beads were incubated for 1 hour in wash buffer containing 1 mg anti-TNF-alpha-FITC antibody
4. Beads from the scFv and control samples were dispensed separately onto microscope slides and covered with cover slips.
5. Photomicrographs were captured using an epifluorescence microscope with an attached camera.
6. The photomicrographs were analyzed using CellProfiler software to determine the integrated fluorescence intensity of each bead detected.

Figure 30:
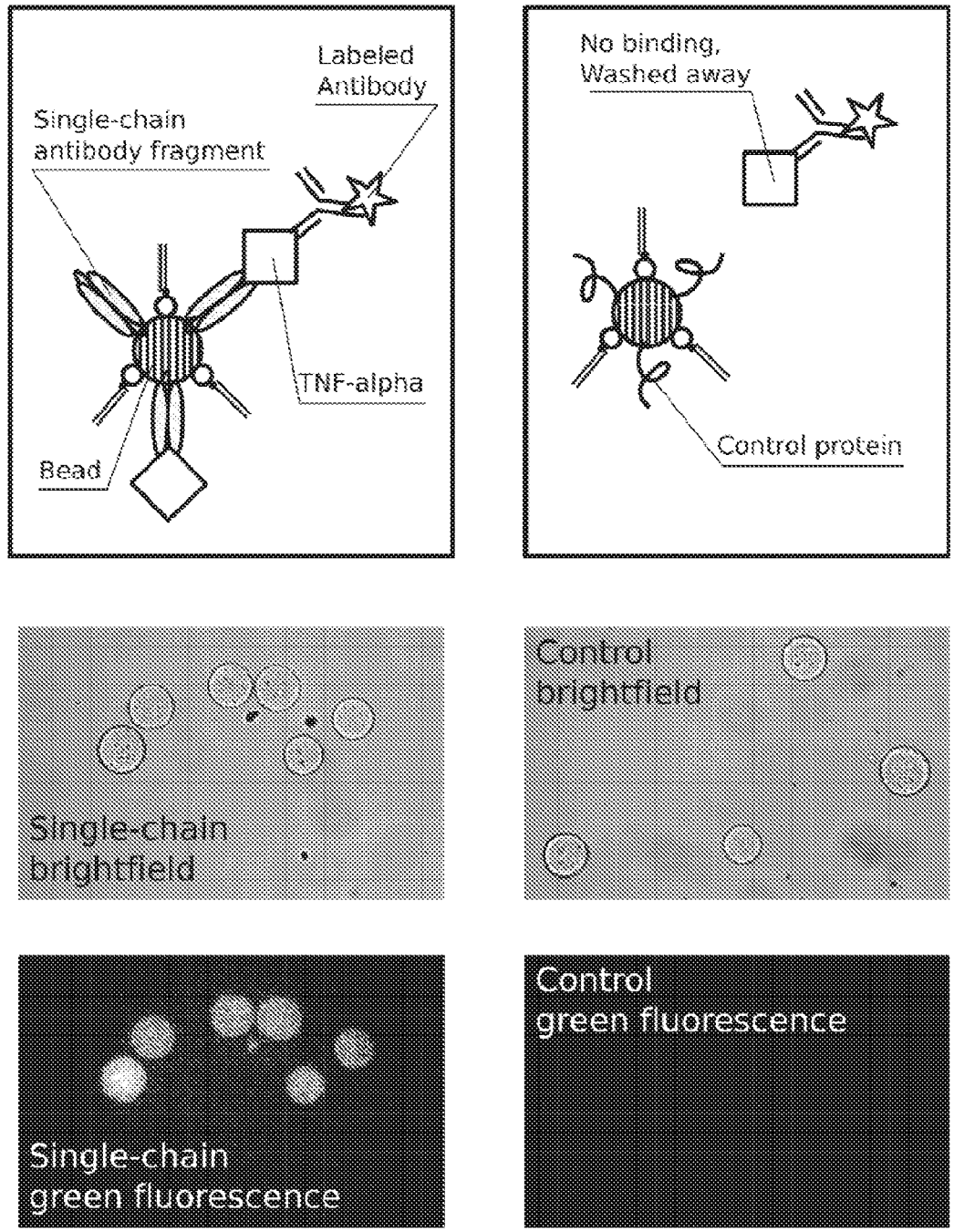
FIG. 30: A schematic of single-chain antibody fragment test and control protein test of the embodiments (upper panel). Examples of brightfield and fluorescence microscopy-based detection of single-chain antibody fragment tests are shown in the lower panels.

FIG. 30 shows a schematic of single-chain antibody fragment test and control protein test. bar plot of average fluorescence intensity for beads from these two samples. The data indicate that the scFv expressed on bead binds to TNF-alpha expected.

Example 8

Biological Activity Testing of Single Beads in Micro Titer Plates

Nucleotide Sequence Preparation
Reagents:
Two different DNA constructs; one construct representing tumor necrosis factor alpha (TNF-alpha); another construct representing a single chain antibody fragment (used as a control); both constructs are optimized for in vitro expression; each obtained from DNA 2.0 (see the World Wide Web at dna20.com) and cloned into the pIVEX vector (5 Prime, Inc.).
DNA Sequence of Constructs to be Tested:
TNF-Alpha Test Construct (SEQ ID NO: 14)
MHHHHHHGSGGSGENLYFQGGSGGSGVRSSSRTPSDKPVAHVVANPQAE

GQLQWLNRRANALLANGVELRDNQLVVPSEGLYLIYSQVLFKGQGCPST

HVLLTHTISRIAVSYQTKVNLLSAIKSPCQRETPEGAEAKPWYEPIYLG

GVFQLEKGDRLSAEINRPDYLDFAESGQVYFGIIAL\*\*

Control ScFV Construct (SEQ ID NO: 15)
MHHHHHHGSGGSGENLYFQGGSGGSGDIQMTQSPSSLSASVGDRVTI

TCKASQNVGTNVAWYQQKPGKAPKALIYSASFLYSGVPYRFSGSGSG

TDFTLTISSLQPEDFATYYCQQYNIYPLTFGQGTKVEIKGGGGSGGG

GSGGGGSGGGGSEVQLVESGGGLVQPGGSLRLSCAASGYVFTDYGMN

WVRQAPGKGLEWMGWINTYIGEPIYADSVKGRFTFSLDTSKSTAYLQ

MNSLRAEDTAVYYCARGYRSYAMDYWQQGTLVTVSS\*\*

The TNF-alpha test construct consisted of a His-tag, a spacer (Seq: GSGGSG; bold-underlined in sequence above), TEV cleavage site, a spacer (Seq: GSGGSG; bold-underlined in sequence above), and the soluble form of TNF-alpha. The Control ScFV construct consisted of a His-tag, a spacer, TEV cleavage site, a spacer, and a ScFV protein that is not anticipated to elicit a response in the NFkB signaling pathway.

Bead-Based Emulsion PCR
Protocols for bead-based emulsion PCR can be found for example in Williams et al. 2006, incorporated herein by reference. A diagram of the process and the resulting product are shown in FIG. 20.
Equipment:
Vortex Genie 2 (Fisher Scientific)
Microcentrifuge (Eppendorf)
PCR machine (Applied Biosystems)
Reagents:
Bi-functional beads with a streptavidin coating and His-tag binding capacity
DNA reverse primer plus linker with 5' dual biotin (IDT)
DNA reverse primer (IDT)
DNA forward primer (IDT)
ABIL EM 90, a surfactant (Degussa)
Mineral oil (Sigma-Aldrich)
2× GoTaq Green Master Mix (Promega)
Span™ 80, a surfactant (Fluka)
1-Butanol (Sigma)
Breaking buffer (10 mM Tris, pH 7.5; 100 mM NaCl; 1% TritonX-100)
PCR Buffer (20 mM Tris, pH 8.4; 50 mM KCl)
TNF-alpha constructs cloned into pIVEX 2.3d (DNA 2.0/5 Prime)
Procedure:
1. Preload bi-functional beads with biotinylated reverse primer
2. Prepare the oil-surfactant mixture by mixing in a 50-mL tube at 25° C.:

| | |
|---|---|
| Span 80 | 1% w/w |
| ABIL EM 90 | 4% w/w |
| Mineral oil | 95% w/w |

3. Prepare standard PCR™ reaction mix with modifications as follows:
Bring up the DNA in TE buffer to standard stock concentration
Set up PCR reaction with the DNA constructs in the pIVEX vector (100 ng/sample)
Add ~3×10$^5$ beads (see above).
Add forward and reverse primers that amplify a 1408 and 1426 base pair segment of the vector DNA sequence for Constructs 1 and 2, respectively, including the T7 promoter, RBS binding site, hexahistidine, TEV protease cleavage site, the TNF-alpha (or control) sequence, and the T7 terminator
4. Create an emulsion as follows:
Dispense 950 µl of oil-surfactant mixture into a microcentrifuge tube.
Add 50 µl of the PCR reaction mix to the tube
Flick tube a few times to disperse water in oil
Vortex the tube for 15 seconds on highest setting (8).
This process creates an emulsion with drop diameter in the range of 5-100 nm, where the majority of beads are one per drop.
5. Transfer to PCR tubes and a PCR machine and run the following protocol:
94° C. for 5 min
Cycle 40 times:
94° C. for 30 sec
57° C. for 30 sec
72° C. for 4 min
72° C. for 7 min
Cool to 4° C.
5. Pool the PCR products and centrifuge. Dispose of the upper oil phase.
6. Extract beads from emulsion with 2 sets of alternating washes of 1-Butanol and Breaking buffer.
7. Wash beads with PCR Buffer
8. Purify beads by centrifugation, wash and store in nuclease-free water.
Emulsion Expression
A wide range of protocols are available for emulsion expression, see for example Tawfik and Griffiths (1998) Nature Biotechnology, 16:652-656; Ghadessy et al. (2001) PNAS, 98:4552-4557 or Ghadessy and Hollinger (2004)

DOI: 10.1093/protein/gzho25, each of which is incorporated herein by reference. An example schematic is shown in FIG. 21.

Equipment:
Vortex Genie 2 (Fisher Scientific)

Reagents:
RTS 100 HY Cell Free Expression kit (5 Prime)
Span 80 (Sigma)
Mineral Oil (Sigma)
Abil EM90 (Degussa)
RNasin Plus (Promega)
Halt Protease Inhibitor Cocktail, EDTA free (Thermo)
Rifampicin (Sigma)
Herring Sperm DNA
DNA-loaded beads from bead-based emulsion PCR
Breaking buffer (10 mM Tris, pH 7.5; 100 mM NaCl; 1% TritonX-100)

Procedure:
1. Supplement the 5 Prime RTS 100 HY extract kit with 20 U RNasin Plus, Halt Protease inhibitor, 2 ug/mL Rifampicin, 1 ug Herring Sperm DNA with beads at 4° C.
2. Prepare oil phase by dissolving 4% Abil EM90 (v/v), 1% (v/v) Span 80 in mineral oil.
3. Create an emulsion as follows:
Dispense 950 μl of oil-surfactant mixture into a microcentrifuge tube.
Add 50 μl of supplemented expression kit to the tube
Flick tube a few times to disperse water in oil
Vortex the tube for 15 s on highest setting (8).
4. Incubate at room temperature for 3 hours.
5. Centrifuge tube and remove top oil layer.
6. Break emulsion with 3 washes of Breaking buffer.
7. Wash beads twice with PBS.
8. Resuspend beads in PBS.

Bioactivity Testing
Equipment:
Cell culture incubator (Fisher Scientific)
Microplate reader (Tecan Safire)
Black, clear bottom, 1536-well microtiter plate (Corning)

Reagents:
Jurkat cells transfected with GFP reporter construct for NF-kappa-B (System Biosciences, Inc.)
RPMI 1640+10% Fetal Bovine Serum+Penicillin/Streptomycin (Life Tech)
HaloTEV Protease (Promega)
Phosphate Buffered Saline (PBS) (Sigma)
0.1 M Dithiothreitol (Sigma)
TNF-alpha (50 ug/mL) (Millipore)
TNF-alpha on beads
Control ScFV on beads
Protein- and DNA-loaded beads from emulsion expression Procedure:
1) Dilute NF-κB-Jurkat cells to $4\times10^6$ cells/ml using the supplemented RPMI 1640 growth media.
2) Prepare the 1536 well for the following layout:

| M | M | M | M |
|---|---|---|---|
| M | A | B | M |
| M | A | B | M |
| M | A | B | M |
| M | A | B | M |
| M | A | B | M |
| M | A | B | M |
| M | A | B | M |
| M | A | B | M |
| M | A | B | M |
| M | M | M | M |

M = Media, A = TNF beads, B = Control beads

3) Add 7. μl of supplemented RMPI 1640 media to all wells labeled "M" in the plate layout above.
4) Create the following cell master mix:

| NFkB-Jurkat Cells | 40 uL |
|---|---|
| 0.1M DTT | 1 uL |
| HaloTEV | 10 uL |
| Supplemented RMPI 1640 | 49 uL |

5) Add 3 μl of the cell master mix to the wells labeled "A" and "B" so that when the test and control beads are added the final number of cells is 4,800 per well.
6) Dilute the TNF-bead and Control-beads in supplemented RPMI 1640 to 1-2 beads per 2 μl.
7) Add 2 μl of TNF-beads to the wells of the plate labeled "A" and add 2 μl of the control-beads to the wells of the plate labeled "B".
8) Incubate the plate for 18 hours at 37 C and 5% $CO_2$.
9) Measure the GFP fluorescence of each well using the Tecan Safire plate reader.

Figure 31A:
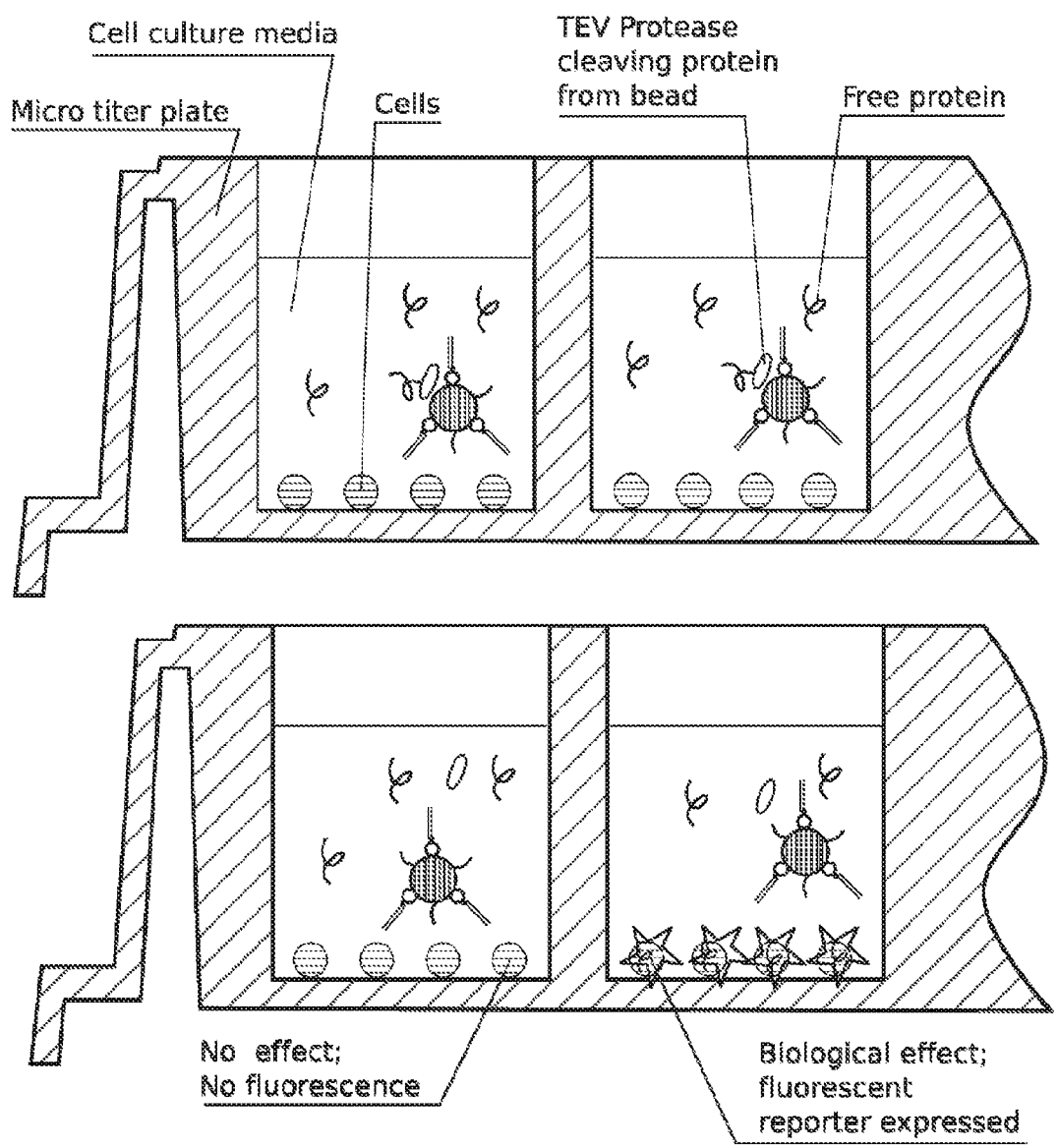
FIG. 31A-B: (A) A schematic of an example "hit" isolation protocol where isolated cell populations are tested in wells of a micro titer plate, see, e.g., Example 8. (B) Graph shows the results of a fluorescence-based screen of the embodiments in wells of a microtiter plate. Wells with 0 beads per well had a comparable GFP signal to what was measured with the control beads. Test wells with 1 and 2 beads per well were able to generate an increased signal over the baseline.
Figure 31B:
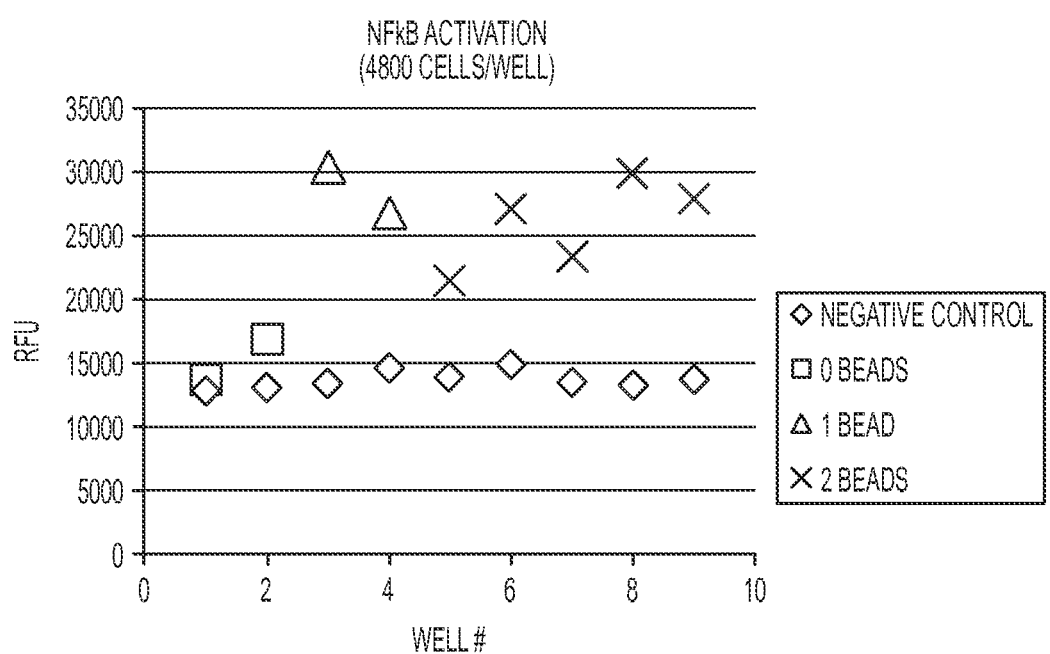

The experiment was performed to determine if a single bead could be used to screen for activity of a protein that induces a cell-reporter in a microtiter plate. A schematic showing the experimental is shown in FIG. 31A. 1536 well plates were used to decrease the volume in which the assay was performed. Control beads consisting of a scFv antibody fragment were generated using the same protocol as the tested TNF-beads. The control beads were used to establish a baseline signal for the assay. The test bead wells ranged from 0-2 beads per well. The wells with 0 beads per well had a comparable GFP signal to what was measured with the control beads (FIG. 31B). Test wells with 1 and 2 beads per well were able to generate an increased signal over the baseline.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766

U.S. Pat. No. 4,661,913
U.S. Pat. No. 4,683,195
U.S. Pat. No. 4,683,202
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,883,750
U.S. Pat. No. 4,989,977
U.S. Pat. No. 5,160,974
U.S. Pat. No. 5,478,722
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Publn. 20070077572
U.S. Publn. 20090197248
U.S. Publn. 20100022414
Ash and Ash, In: *Handbook of Industrial Surfactants*, Gower Pub. Co., 1993.
Barany, *PCR Methods Appl.*, 1:5-16, 1991.
Baret et al. *Chem. and Biol.*, 17:528-536, 2010.
Becher, In: *Emulsions: Theory and Practice*, Reinhold Pub. Corp., 189, NY, 1957.
Benita, In: *Drugs and Pharmaceutical Sciences*, Swarbrick (Ed.), NY, Marcel Dekker, 1996.
Blattner and Dahlberg, *Nature New Biol.*, 237:227-232, 1972.
Brouzes et al., *Proc. Natl. Acad. Sci. USA*, 106(34):14195-14200, 2009
Bru & Walde, *Eur. J. Biochem.*, 199(1):95-103, 1991.
Bru & Walde, *Biochem. Mol. Biol. Int.*, 31(4):685-692, 1993.
Cahill et al., *Clin. Chem.*, 37:1482-1485, 1991.
Chakrabarti et al., *J. Mol. Evol.*, 39(6), 555-559, 1994.
Chang, *Methods Enzymol.*, 136(67):67-82, 1987.
Chang, In *Droplets and Nanoparticles in Medicine and Pharmacy*, Donbrow (Ed.), 323-339, CRC Press, Fl., 1992.
Chetverin and Spirin, *Prog. Nucleic Acid Res. Mol. Biol.*, 51:225-270, 1995.
Clackson and Wells, *Trends Biotechnol.*, 12:173-184, 1994.
Creagh et al., *Enzyme Microb. Technol.* 15(5):383-392, 1993.
Dickinson, In: *Emulsions and Droplet Size Control*, Wedlock (Ed.), Butterworth-Heinemann, Oxford, 191-257, 1994.
European Appln. 320 308
European Appln. 329 822
Fahy et al., *PCR Methods Appl.*, 1:25-33, 1991.
Finch, *Spec. Publ.-R. Soc. Chem.*, 138:35, 1993.
Frohman, In: *PCR Protocols: A Guide To Methods And Applications*, Academic Press, NY, 1990.
GB Appln. 2 202 328
Ghadessy and Hollinger, DOI: 10.1093/protein/gzho25, 2004.
Ghadessy et al., *Proc. Natl. Acad. Sci. USA*, 98:4552-4557, 2001.
Haber et al., *Eur. J. Biochem.*, 217(2):567-573, 1993.
Innis et al., *Proc. Natl. Acad. Sci. USA*, 85(24):9436-9440, 1988.
Katanaev et al., *Febs Lett.*, 359:89-92, 1995.
Kumar et al., *Biochim. Biophys. Acta*, 996(1-2):1-6, 1989.
Kwoh et al., *Proc. Natl. Acad. Sci. USA*, 86:1173, 1989.
Landegren et al., *Science*, 241:1077-1080, 1988.
Lim & Sun, *Science*, 210(4472):908-910, 1980.
Lim, In: *Biomedical Applns. of Microencapsulation*, Fla., CRC Press, 1984.
Lissant, In: *Emulsions and Emulsion Technology*, Marcel Dekker, NY, 1974.
Lissant, In: *Emulsions and Emulsion Technology*, NY, Marcel Dekker, 1984.
Luisi and Steinmann-Hofmann, *Methods Enzymol.*, 136: 188-216, 1987.
Manley et al., *Methods Enzymol.*, 101:568-582, 1983.
Mao & Walde, *Biochem. Biophys. Res. Commun.*, 178(3): 1105-1112, 1991.
Mao et al., *Eur. J. Biochem.*, 208(1):165-170, 1992.
Melton et al., *Nucleic Acids, Res.*, 12:703556, 1984.
Menger & Yamada, *J. Am. Chem. Soc.*, 101:6731-6734, 1979.
Miele et al., *J. Mol. Biol.*, 171:281-295, 1983.
New, In: *Liposomes: A Practical Approach*, Richwood and Hames (Eds.), Oxford Univ. Press, Oxford, 1990.
Oberholzer et al., *Chem. Biol.*, 2:677-682, 1995a.
Oberholzer et al., *Biochem. Biophys. Res. Comm.*, 207(1): 250-257, 1995b.
Ohara et al., *Proc. Natl. Acad. Sci. USA*, 86:5673-5677, 1989.
PCT Appln. PCT/US2004/010903
PCT Appln. PCT/US87/00880
PCT Appln. PCT/US89/01025
PCT Appln. WO 88/10315
PCT Appln. WO 89/06700
PCT Appln. WO 90/07641
Perez-Gilabert et al., *Biochem. J.*, 288(Pt. 3):1011-1015, 1992.
Roberts et al., *Proc. Natl. Acad. Sci. USA*, 72:1922-1926, 1975.
Roberts, *Nature*, 224:1168-1174, 1969.
Rosenberg et al., *J. Biol. Chem.*, 250:4755-4764, 1975.
Saiki et al., *Science*, 239:487-491, 1988.
Sambrook and Russell, Molecular Cloning: A Laboratory Manual, 3rd Edition, Cold Spring Harbor Laboratory, N.Y., 1989.
Schick, In: *Nonionic Surfactants*, Marcel Dekker, NY, 1966.
Sherman, In: *Emulsion Science*, Academic Press, London, 1968.
Song et al., In: *A Microfluidic System for Controlling Reaction Networks in Time*, Angewandte Chemie, 42(7):768-772, 2003.
Sun et al., In; *Microencapsulation and Nanoparticles in Medicine and Pharmacy*, Donbrow (ed.), 315-322, CRC Press, Fl, 1992.
Tawfik and Griffiths, *Nat. Biotechnol.*, 16:652-656, 1998.
van Hal et al., In: *Microencapsulation: Methods and Industrial Applications*, Benita (Ed.), 329-347, Marcel Dekker, NY, 1996.

Walde et al., *Eur. J. Biochem.*, 173(2):401-409, 1988.
Walde et al., *Biochemistry*, 32(15), 4029-4034, 1993.
Walde et al., *J. Am. Chem. Soc.*, 116:7541-7547, 1994.
Walker et al., *Nucleic Acids Res.*, 20:1691-1696, 1992.
Weil et al., *Cell*, 18:469-484, 1979.
Whateley, In: *Microencapsulation: Methods and Industrial Applications*, Benita (Ed.), 349-375, Marcel Dekker, NY, 1996.
Wick & Luisi, *Chem. Biol.*, 3(4):277-285, 1996
Williams et al., *Nature Methods*, 3(7):545, 2006.

What is claimed is:

1. A method of providing a nucleic acid molecule encoding an active polypeptide having a desired activity, the method comprising the steps of:
    (a) obtaining a population of nucleic acid molecules comprising sequences that encode polypeptides, wherein individual members of the population encode different polypeptides and are bound to a carrier, to provide a population of carrier-bound nucleic acid molecules;
    (b) encapsulating individual carrier-bound nucleic acid molecules in microcapsules and incubating the encapsulated carrier-bound nucleic acid molecules under conditions that permit expression of polypeptides, such that the encoded polypeptide molecule becomes selectively associated on said carrier with at least one copy of the nucleic acid molecule that encodes it within its respective microcapsule;
    (c) breaking the microcapsules and dissociating individual polypeptides from their respective carriers and the nucleic acid that encodes it and testing the individual dissociated polypeptides for a response to a target molecule; and
    (d) identifying polypeptides that provide a response to the target molecules, to provide the nucleic acid molecule encoding the active polypeptide.

2. The method of claim 1, wherein the target molecule comprises a test cell.

3. The method of claim 2, wherein the target molecule is expressed in the surface of the test cell.

4. The method of claim 2, wherein (c) testing a target molecule for a response to individual member polypeptides of the population comprises testing cells for a biological response to individual member polypeptides of the population.

5. The method of claim 2, wherein the cells are bacterial cells, fungal cells, insect cells or mammalian cells.

6. The method of claim 2, wherein testing cells for a biological response comprises detecting a change in the optical or fluorescent properties of the cells.

7. The method of claim 6, wherein detecting a change in the optical or fluorescent properties of the cells comprises detecting binding of a labeled reagent to the cells.

8. The method of claim 7, wherein the labeled reagent comprises a fluorescent label.

9. The method of claim 7, wherein the labeled reagent is an antibody.

10. The method of claim 2, wherein testing the cells for a biological response to the polypeptide comprises determining whether the nucleic acid molecules are bound to the component of the test cells.

11. The method of claim 1, wherein testing a target molecule for a response to individual member polypeptides of the population comprises contacting the member polypeptides with target molecules isolated in a gel, a well of micro titer plate or a microcapsule of an emulsion.

12. The method of claim 1, wherein each polypeptide molecule is associated with at least one copy of the nucleic acid molecule that encodes it in a gel, a well of micro titer plate or a microcapsule of an emulsion.

13. The method of claim 1, wherein identifying the sequence of nucleic acid molecules associated with polypeptides comprises sequencing the nucleic acid molecules.

14. The method of claim 1, wherein the population of nucleic acid molecules comprises sequences that encode antibody polypeptides.

15. The method of claim 1, wherein the polypeptide molecules are dissociated from the at least one copy of the nucleic acid molecule that encodes it prior to said testing.

16. The method of claim 15, further comprising contacting the polypeptide molecules with a dissociation agent prior to said testing.

17. The method of claim 1, wherein the response to individual member polypeptides of the population comprises binding of the individual member polypeptides to the target molecule.

18. The method of claim 1, wherein the nucleic acid molecules are bound to a detectable tag.

19. The method of claim 1, wherein the carrier is a carrier bead.

20. The method of claim 19, wherein the nucleic acid molecules and/or carrier bead comprise a detectable label.

21. The method according to claim 1,
    wherein the polypeptides are antibody polypeptides.

* * * * *

```
                          SEQUENCE LISTING

<160> NUMBER OF SEQ ID NOS: 26

<210> SEQ ID NO 1
<211> LENGTH: 26
<212> TYPE: PRT
<213> ORGANISM: Apis mellifera

<400> SEQUENCE: 1

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic peptide

<400> SEQUENCE: 2

Gly Ile Gly Ala Val Leu Lys Val Leu Thr Thr Gly Leu Pro Thr Leu
1               5                   10                  15

Ile Ser Trp Ile Lys Ser Lys Arg Gln Lys
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic peptide

<400> SEQUENCE: 3

Gly Ile Gly Ala Leu Ile Lys Val Leu Thr Thr Gly Leu Pro Met Leu
1               5                   10                  15

Ile Ser Trp Ile Lys Arg Lys Arg Asn Lys
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic peptide

<400> SEQUENCE: 4

Gly Ile Gly Ala Trp Thr Lys Val Leu Thr Thr Gly Leu Pro Gly Leu
1               5                   10                  15

Ile Ser Trp Ile Lys Arg Lys Arg Leu Arg
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic peptide
```

```
<400> SEQUENCE: 5

Gly Ile Gly Ala Thr Val Lys Val Leu Ser Thr Gly Leu Arg Phe Leu
1               5                   10                  15

Ile Ser Trp Ile Lys Arg Lys Arg Lys Tyr
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

Gly Ile Gly Ala Ile Ala Lys Val Leu Ser Thr Gly Leu Pro Arg Leu
1               5                   10                  15

Ile Ser Trp Ile Lys Gly Lys Arg Ile Arg
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic peptide

<400> SEQUENCE: 7

Gly Ile Gly Ala Val Leu Lys Val Leu Gly Thr Gly Leu Pro Ala Leu
1               5                   10                  15

Ile Ser Trp Ile Lys Phe Lys Arg Phe Pro
            20                  25

<210> SEQ ID NO 8
<211> LENGTH: 171
<212> TYPE: PRT
<213> ORGANISM: Artificial Sequence
<220> FEATURE:
<223> OTHER INFORMATION: Synthetic peptide

<400> SEQUENCE: 8

Met His His His His His His Glu Asn Leu Tyr Phe Gln Gly Val Arg
1               5                   10                  15

Ser Ser Ser Arg Thr Pro Ser Asp Lys Pro Val Ala His Val Val Ala
            20                  25                  30

Asn Pro Gln Ala Glu Gly Gln Leu Gln Trp Leu Asn Arg Arg Ala Asn
        35                  40                  45

Ala Leu Leu Ala Asn Gly Val Glu Leu Arg Asp Asn Gln Leu Val Val
    50                  55                  60

Pro Ser Glu Gly Leu Tyr Leu Ile Tyr Ser Gln Val Leu Phe Lys Gly
65                  70                  75                  80

Gln Gly Cys Pro Ser Thr His Val Leu Leu Thr His Thr Ile Ser Arg
                85                  90                  95

Ile Ala Val Ser Tyr Gln Thr Lys Val Asn Leu Leu Ser Ala Ile Lys
            100                 105                 110

Ser Pro Cys Gln Arg Glu Thr Pro Glu Gly Ala Glu Ala Lys Pro Trp
        115                 120                 125

Tyr Glu Pro Ile Tyr Leu Gly Gly Val Phe Gln Leu Glu Lys Gly Asp
    130                 135                 140

Arg Leu Ser Ala Glu Ile Asn Arg Pro Asp Tyr Leu Asp Phe Ala Glu
145                 150                 155                 160
```

```
Ser Gly Gln Val Tyr Phe Gly Ile Ile Ala Leu
            165                 170

<210> SEQ ID NO 9
<211> LENGTH: 177
<212> TYPE: PRT
<213> ORGANISM: Artificial Sequence
<220> FEATURE:
<223> OTHER INFORMATION: Synthetic peptide

<400> SEQUENCE: 9

Met His His His His His Gly Ser Gly Gly Ser Gly Glu Asn Leu
1               5                   10                  15

Tyr Phe Gln Gly Val Arg Ser Ser Arg Thr Pro Ser Asp Lys Pro
                20                  25                  30

Val Ala His Val Val Ala Asn Pro Gln Ala Glu Gly Gln Leu Gln Trp
            35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu

<210> SEQ ID NO 10
<211> LENGTH: 177
<212> TYPE: PRT
<213> ORGANISM: Artificial Sequence
<220> FEATURE:
<223> OTHER INFORMATION: Synthetic peptide

<400> SEQUENCE: 10

Met His His His His His Gly Ser Gly Gly Ser Gly Glu Asn Leu
1               5                   10                  15

Tyr Phe Gln Gly Val Arg Ser Ser Arg Thr Pro Ser Asp Lys Pro
                20                  25                  30

Val Ala His Val Val Ala Asn Pro Gln Ala Glu Gly Gln Leu Gln Trp
            35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110
```

-continued

Leu Leu Ser Ala Ile Lys Ser Pro Cys Gln Arg Glu Thr Pro Glu Gly
            115                 120                 125

Ala Glu Ala Lys Pro Trp Tyr Glu Pro Ile Tyr Leu Gly Gly Val Phe
130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
            165                 170                 175

Leu

<210> SEQ ID NO 11
<211> LENGTH: 272
<212> TYPE: PRT
<213> ORGANISM: Artificial Sequence
<220> FEATURE:
<223> OTHER INFORMATION: Synthetic peptide

<400> SEQUENCE: 11

Met His His His His His Glu Asn Leu Tyr Phe Gln Gly Ser Ala
1               5                   10                  15

Gly Gln Ser Ser Gly Arg Ala Thr Ala Leu Thr Glu Gly Ala Lys Leu
            20                  25                  30

Phe Glu Lys Glu Ile Pro Tyr Ile Thr Glu Leu Glu Gly Asp Val Glu
        35                  40                  45

Gly Met Lys Phe Ile Ile Lys Gly Glu Gly Thr Gly Asp Ala Thr Thr
    50                  55                  60

Gly Thr Ile Lys Ala Lys Tyr Ile Cys Thr Thr Gly Asp Leu Pro Val
65                  70                  75                  80

Pro Trp Ala Thr Leu Val Ser Thr Leu Ser Tyr Gly Val Gln Cys Phe
                85                  90                  95

Ala Lys Tyr Pro Ser His Ile Lys Asp Phe Phe Lys Ser Ala Met Pro
            100                 105                 110

Glu Gly Tyr Thr Gln Glu Arg Thr Ile Ser Phe Glu Gly Asp Gly Val
        115                 120                 125

Tyr Lys Thr Arg Ala Met Val Thr Tyr Glu Arg Gly Ser Ile Tyr Asn
    130                 135                 140

Arg Val Thr Leu Thr Gly Glu Asn Phe Lys Lys Asp Gly His Ile Leu
145                 150                 155                 160

Arg Lys Asn Val Ala Phe Gln Cys Pro Pro Ser Ile Leu Tyr Ile Leu
                165                 170                 175

Pro Asp Thr Val Asn Asn Gly Ile Arg Val Glu Phe Asn Gln Ala Tyr
            180                 185                 190

Asp Ile Glu Gly Val Thr Glu Lys Leu Val Thr Lys Cys Ser Gln Met
        195                 200                 205

Asn Arg Pro Leu Ala Gly Ser Ala Ala Val His Ile Pro Arg Tyr His
    210                 215                 220

His Ile Thr Tyr His Thr Lys Leu Ser Lys Asp Arg Asp Glu Arg Arg
225                 230                 235                 240

Asp His Met Cys Leu Val Glu Val Val Lys Ala Val Asp Leu Asp Thr
                245                 250                 255

Tyr Gln Ala Gly Ala Met Ala Ser Met Thr Gly Gly Gln Gln Met Gly
            260                 265                 270

<210> SEQ ID NO 12
<211> LENGTH: 271

<212> TYPE: PRT
<213> ORGANISM: Artificial Sequence
<220> FEATURE:
<223> OTHER INFORMATION: Synthetic peptide

<400> SEQUENCE: 12

Met His His His His His Gly Ser Gly Gly Ser Gly Glu Asn Leu
1               5                   10                  15

Tyr Phe Gln Gly Gly Ser Gly Gly Ser Gly Asp Ile Gln Met Thr Gln
                20                  25                  30

Ser Pro Ser Ser Leu Ser Ala Ser Val Gly Asp Arg Val Thr Ile Thr
            35                  40                  45

Cys Lys Ala Ser Gln Asn Val Gly Thr Asn Val Ala Trp Tyr Gln Gln
50                  55                  60

Lys Pro Gly Lys Ala Pro Lys Ala Leu Ile Tyr Ser Ala Ser Phe Leu
65                  70                  75                  80

Tyr Ser Gly Val Pro Tyr Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Tyr Asn Ile Tyr Pro Leu Thr Phe Gly Gln Gly Thr
        115                 120                 125

Lys Val Glu Ile Lys Gly Gly Gly Gly Ser Gly Gly Gly Gly Ser Gly
130                 135                 140

Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
            165                 170                 175

Ala Ser Gly Tyr Val Phe Thr Asp Tyr Gly Met Asn Trp Val Arg Gln
        180                 185                 190

Ala Pro Gly Lys Gly Leu Glu Trp Met Gly Trp Ile Asn Thr Tyr Ile
    195                 200                 205

Gly Glu Pro Ile Tyr Ala Asp Ser Val Lys Gly Arg Phe Thr Phe Ser
210                 215                 220

Leu Asp Thr Ser Lys Ser Thr Ala Tyr Leu Gln Met Asn Ser Leu Arg
225                 230                 235                 240

Ala Glu Asp Thr Ala Val Tyr Tyr Cys Ala Arg Gly Tyr Arg Ser Tyr
                245                 250                 255

Ala Met Asp Tyr Trp Gln Gln Gly Thr Leu Val Thr Val Ser Ser
            260                 265                 270

<210> SEQ ID NO 13
<211> LENGTH: 40
<212> TYPE: PRT
<213> ORGANISM: Artificial Sequence
<220> FEATURE:
<223> OTHER INFORMATION: Synthetic peptide

<400> SEQUENCE: 13

Met His His His His His Gly Ser Gly Gly Ser Gly Glu Asn Leu
1               5                   10                  15

Tyr Phe Gln Gly Asp Phe Lys Cys Pro Ser Glu Trp Tyr Ala Tyr Asp
                20                  25                  30

Gln His Cys Tyr Arg Ile Ile Asn
            35                  40

<210> SEQ ID NO 14

```
<211> LENGTH: 183
<212> TYPE: PRT
<213> ORGANISM: Artificial Sequence
<220> FEATURE:
<223> OTHER INFORMATION: Synthetic peptide

<400> SEQUENCE: 14
```

Met His His His His His Gly Ser Gly Gly Ser Gly Glu Asn Leu
1               5                   10                  15

Tyr Phe Gln Gly Gly Ser Gly Ser Gly Val Arg Ser Ser Ser Arg
            20                  25                  30

Thr Pro Ser Asp Lys Pro Val Ala His Val Val Ala Asn Pro Gln Ala
        35                  40                  45

Glu Gly Gln Leu Gln Trp Leu Asn Arg Arg Ala Asn Ala Leu Leu Ala
    50                  55                  60

Asn Gly Val Glu Leu Arg Asp Asn Gln Leu Val Val Pro Ser Glu Gly
65                  70                  75                  80

Leu Tyr Leu Ile Tyr Ser Gln Val Leu Phe Lys Gly Gln Gly Cys Pro
                85                  90                  95

Ser Thr His Val Leu Leu Thr His Thr Ile Ser Arg Ile Ala Val Ser
            100                 105                 110

Tyr Gln Thr Lys Val Asn Leu Leu Ser Ala Ile Lys Ser Pro Cys Gln
        115                 120                 125

Arg Glu Thr Pro Glu Gly Ala Glu Ala Lys Pro Trp Tyr Glu Pro Ile
    130                 135                 140

Tyr Leu Gly Gly Val Phe Gln Leu Glu Lys Gly Asp Arg Leu Ser Ala
145                 150                 155                 160

Glu Ile Asn Arg Pro Asp Tyr Leu Asp Phe Ala Glu Ser Gly Gln Val
                165                 170                 175

Tyr Phe Gly Ile Ile Ala Leu
            180

```
<210> SEQ ID NO 15
<211> LENGTH: 271
<212> TYPE: PRT
<213> ORGANISM: Artificial Sequence
<220> FEATURE:
<223> OTHER INFORMATION: Synthetic peptide

<400> SEQUENCE: 15
```

Met His His His His His Gly Ser Gly Gly Ser Gly Glu Asn Leu
1               5                   10                  15

Tyr Phe Gln Gly Gly Ser Gly Ser Gly Asp Ile Gln Met Thr Gln
            20                  25                  30

Ser Pro Ser Ser Leu Ser Ala Ser Val Gly Asp Arg Val Thr Ile Thr
        35                  40                  45

Cys Lys Ala Ser Gln Asn Val Gly Thr Asn Val Ala Trp Tyr Gln Gln
    50                  55                  60

Lys Pro Gly Lys Ala Pro Lys Ala Leu Ile Tyr Ser Ala Ser Phe Leu
65                  70                  75                  80

Tyr Ser Gly Val Pro Tyr Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Tyr Asn Ile Tyr Pro Leu Thr Phe Gly Gln Gly Thr
        115                 120                 125

Lys Val Glu Ile Lys Gly Gly Gly Gly Ser Gly Gly Gly Gly Ser Gly

```
                130                 135                 140
Gly Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
            165                 170                 175

Ala Ser Gly Tyr Val Phe Thr Asp Tyr Gly Met Asn Trp Val Arg Gln
            180                 185                 190

Ala Pro Gly Lys Gly Leu Glu Trp Met Gly Trp Ile Asn Thr Tyr Ile
        195                 200                 205

Gly Glu Pro Ile Tyr Ala Asp Ser Val Lys Gly Arg Phe Thr Phe Ser
    210                 215                 220

Leu Asp Thr Ser Lys Ser Thr Ala Tyr Leu Gln Met Asn Ser Leu Arg
225                 230                 235                 240

Ala Glu Asp Thr Ala Val Tyr Tyr Cys Ala Arg Gly Tyr Arg Ser Tyr
                245                 250                 255

Ala Met Asp Tyr Trp Gln Gln Gly Thr Leu Val Thr Val Ser Ser
            260                 265                 270

<210> SEQ ID NO 16
<211> LENGTH: 20
<212> TYPE: PRT
<213> ORGANISM: Apis mellifera

<400> SEQUENCE: 16

Glu Val Lys His Met His His His His His Glu Asn Leu Tyr Phe
1               5                   10                  15

Gln Gly Gly Ile
        20

<210> SEQ ID NO 17
<211> LENGTH: 60
<212> TYPE: DNA
<213> ORGANISM: Apis mellifera

<400> SEQUENCE: 17
gaggtaaaac atatgcatca ccaccaccat cacgagaatc tgtagtttca aggcggtatc    60

<210> SEQ ID NO 18
<211> LENGTH: 20
<212> TYPE: PRT
<213> ORGANISM: Apis mellifera

<400> SEQUENCE: 18

Gly Ala Val Leu Lys Val Leu Thr Thr Gly Leu Pro Ala Leu Ile Ser
1               5                   10                  15

Trp Ile Lys Arg
        20

<210> SEQ ID NO 19
<211> LENGTH: 60
<212> TYPE: DNA
<213> ORGANISM: Apis mellifera

<400> SEQUENCE: 19
ggcgcagttc tgaaagtgct gaccacgggt ttgccggctc tgattagctg gatcaaacgt    60

<210> SEQ ID NO 20
<211> LENGTH: 6
<212> TYPE: PRT
<213> ORGANISM: Apis mellifera
```

<400> SEQUENCE: 20

Lys Arg Gln Gln Leu Glu
1               5

<210> SEQ ID NO 21
<211> LENGTH: 24
<212> TYPE: DNA
<213> ORGANISM: Apis mellifera

<400> SEQUENCE: 21
aagcgccasc agtgataact cgag                                          24

<210> SEQ ID NO 22
<211> LENGTH: 7
<212> TYPE: PRT
<213> ORGANISM: Apis mellifera

<400> SEQUENCE: 22

Val Leu Thr Pro Ala Gln Gln
1               5

<210> SEQ ID NO 23
<211> LENGTH: 24
<212> TYPE: DNA
<213> ORGANISM: Apis mellifera

<400> SEQUENCE: 23
gttctgaccc cggctcgtca gcag                                          24

<210> SEQ ID NO 24
<211> LENGTH: 26
<212> TYPE: PRT
<213> ORGANISM: Apis mellifera

<400> SEQUENCE: 24

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 25
<211> LENGTH: 26
<212> TYPE: PRT
<213> ORGANISM: Apis mellifera
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X is either Pro or Arg
<220> FEATURE:
<221> NAME/KEY: misc_feature
<222> LOCATION: (22)..(22)
<223> OTHER INFORMATION: Xaa can be any naturally occurring amino acid

<400> SEQUENCE: 25

Gly Ile Gly Ala Xaa Xaa Lys Val Leu Xaa Thr Gly Leu Cys Cys Leu
1               5                   10                  15

Ile Ser Trp Ile Lys Xaa Lys Arg Lys Lys

```
                    20                       25

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

His His His His His His
1               5
```